United States Patent [19]
Llinás et al.

[11] Patent Number: 6,114,555
[45] Date of Patent: Sep. 5, 2000

[54] FUNCTIONALIZED METALLOCENE COMPOUNDS, SYNTHESIS PROCESS AND USE THEREOF

[75] Inventors: Gerardo Hidalgo Llinás, Cartagena; Antonio Muñoz-Escalona Lafuente, Madrid, both of Spain

[73] Assignee: Repsol Quimica S.A., Madrid, Spain

[21] Appl. No.: 09/300,301

[22] Filed: Apr. 27, 1999

[30] Foreign Application Priority Data

Apr. 29, 1998 [EP] European Pat. Off. .............. 98500105

[51] Int. Cl.$^7$ .................... C07F 17/00; C07F 7/00
[52] U.S. Cl. .................... 556/11; 556/7; 556/8; 556/12; 556/28; 556/53; 502/103; 502/117; 526/160; 526/943
[58] Field of Search .............. 556/7, 8, 11, 12, 556/28, 53; 502/103, 117; 526/160, 943

[56] References Cited

U.S. PATENT DOCUMENTS

| | | | |
|---|---|---|---|
| 5,753,769 | 5/1998 | Ueda et al. .............. | 525/323 |
| 6,018,064 | 1/2000 | Llatas et al. .............. | 556/11 |

FOREIGN PATENT DOCUMENTS

| | | |
|---|---|---|
| 0 206 794 | 12/1986 | European Pat. Off. . |
| 0 293 815 | 12/1988 | European Pat. Off. . |
| 0 295 312 | 12/1988 | European Pat. Off. . |
| 0 372 414 | 6/1990 | European Pat. Off. . |
| 0 757 053 | 2/1997 | European Pat. Off. . |
| 0 757 992 | 2/1997 | European Pat. Off. . |
| 0 802 203 | 10/1997 | European Pat. Off. . |
| 0 839 836 | 5/1998 | European Pat. Off. . |

OTHER PUBLICATIONS

Plenio et al., Journal of Organometallic Chemistry, vol. 544, pp. 133–137, 1997.

Yasuda et al., "Rare earth metal initiated polymerizations of polar and nonpolar monomers to give high molecular weight polymers with extremely narrow molecular weight distribution," *Macromol. Chem. Phys.*, 196, pp. 2417–2441 (1995).

Plenio et al., "n$^5$–Complexes of cyclopentadienylsilylethers ($C_5H_4OSiR_3$) and hydroxycyclopentadiene ($C_5H_4OH$) with titanium and zirconium chlorides," *Journal of Organometallic Chemistry*, 544, pp. 133–137 (1997).

Wilkinson et al., "Bis–Cyclopentadienyl derivatives of some transition elements," *J. Am. Chem. Soc.*, vol. 75, p. 1011–1012 (1953).

Nugent et al., "Zirconium–Mediated Ring Construction from Dienes: Remarkable Effect of Ligands on Stereochemistry," *J. Am. Chem. Soc.*, vol. 111, pp. 6435–6437 (1989).

Kesti et al., "Homogeneous Ziegler–Natta Polymerization of Functionalized Monomers Catalyzed by Cationic Group IV Metallocenes," *J. Am. Chem. Soc.*, vol. 114, pp. 9679–9680 (1992).

*Primary Examiner*—Porfirio Nazario-Gonzalez
*Attorney, Agent, or Firm*—Ladas & Parry

[57] ABSTRACT

The present invention relates to nietallocene compounds characterized by the following formulas:

$$(LR_k)_z[LR_{k-j}(R'OH)_j]_xMX_y \qquad \text{I}$$

$$
\begin{array}{c}
(R)_d \diagdown \quad \diagup L(R^1OH)_a(R)_{k-a-1} \\
Q_m \qquad M \\
(HOR^1)_c \diagup \quad \diagdown L(R^1OH)_b(R)_{k-b-1} \\
\end{array}
\quad X \atop X
\qquad \text{II}
$$

$$
\begin{array}{c}
(R)_d \diagdown \quad \diagup L(R^1OH)_a(R)_{k-a-1} \\
Q_m \qquad M \\
(HOR^1)_c \diagup \quad \diagdown L' \\
(R)_e \quad (R^1OH)_g
\end{array}
\quad X \atop X
\qquad \text{III}
$$

wherein:

L, equal to or different from each other, is selected from the group comprising: cyclopentadienyl, indenyl, tetrahydroindenyl, fluorenyl, octahydrofluorenyl or benzoindenyl; each R is independently selected from hydrogen, $C_1$–$C_{20}$ alkyl, $C_3$–$C_{20}$ cycloalkyl, $C_6$–$C_{20}$ aryl, $C_3$–$C_{20}$ alkenyl $C_7$–$C_{20}$ arylalkyl, $C_7$–$C_{20}$ alkylaryl, $C_8$–$C_{20}$ arylalkenyl, linear or branched, optionally substituted by 1 to 10 halogen atoms, or a group $SiR''_3$; each $R'$ equal to or different from each other, is a group $SiR''_2$, or a divalent aliphatic or aromatic hydrocarbon group containing from 1 to 20 carbon atoms, optionally containing from 1 to 5 heteroatoms of groups 14 to 16 of the periodic table of the elements and boron; each Q is independently selected from B, C, Si, Ge, Sn; M is a metal of group 3, 4 or 10 of the Periodic Table, Laitlanide or Actinide; each X is independently selected from: hydrogen, chlorine, bromine, $OR''$, $NR''_2$, $C_1$–$C_{20}$ alkyl or $C_6$–$C_{20}$ aryl; each $R''$ is independently selected from $C_1$–$C_{20}$ alkyl, $C_3$–$C_{20}$ cycloalkyl, $C_6$–$C_{20}$ aryl, $C_3$–$C_{20}$ alkenyl, $C_7$–$C_{20}$ arylalkyl, $C_7$–$C_{20}$ arylalkenyl or alkylaryl, linear or branched; $R''$ is methyl, ethyl, isopropyl; L' is N or O.

26 Claims, No Drawings

FUNCTIONALIZED METALLOCENE COMPOUNDS, SYNTHESIS PROCESS AND USE THEREOF

The present invention relates to new metallocene compounds and to the process for their preparation.

STATE OF THE ART

The metallocene compounds field has experimented a big development since the first syntheses of these compounds in the fifties (G. Wilkinson et al., *J. Am. Chem. Soc.,* 1953, 75, 1011). This development is basically due to the large increase in the number of applications wherein these compounds are used. So, they can be used as catalysts of hydrogenation, epoxidation, double bond isomerization, ketons reduction, aldolic reaction, synthesis of different substituted olefins, etc., but their largest use is as catalyst components for olefin polymerization, as they can be activated for this use by alumoxanes or other non-coordinative anion precursors (for example boron compounds). In this field metallocenes of group 4 (Ti, Zr, Hf) in particular have been developed, but also metallocenes of groups 3, 5 and 6. Metallocenes were prepared for working in very different conditions (solution, suspension, mass, gas phase, high pressure and temperature processes, etc.). They were used for polymerizing and copolymerizing simple alpha-olefins, basically ethylene and propylene, but also more complex olefins, cycloolefins, diolefins and also olefins with polar groups; for example W. A. Nugent et al., *J. Am. Chem. Soc.* 1989, 111, 6435; M. R. Resti G. W. Coates, R. M. Waymouth et al., *J. Am. Chem. Soc.* 1992, 114, 9679; H Yasuda et al., *Macromol.Chem.Phys,* 1995, 196, 2417).

For adapting to the different needs of each application very different metallocenes were synthesized, basically differing for the different substitution around the cyclopentadienyl rings that form it, as it is possible to influence in this way, both sterically and electronically, the reactivity of their active centers.

A development in the field of metallocenes has been the preparation of functionalized metallocenes, i.e. metallocenes containing a functional group that allows the preparation of more complex structures.

EP 372414 discloses metallocenes having a hydrocarbon group containing a double bond linked to the $\eta^5$ ligand.

In Journal of Organometallic Chemistry (vol. 544, 1997, 133–137), (hydroxy-cyclopentadienyl) (cyclopentadienyl) titanium dichloride is obtained as a by product of a reaction for synthesizing (triethylsilyloxy-cyclopentadienyl) (cyclopentadienyl) titanium dichioride. However, all the attempts to produce single crystals of hydroxy-complex as well as all the attempts to hydrolyze in controlled conditions triethylsilyloxy complex have been unsuccessful since this compounds are not very stable in solution.

Furthermore the obtained hydroxy-compound is not very reactive since the OH group is directly bond to the aromatic ring.

It has been surprisingly found that it is possible to prepare metallocene compounds having an hydroxyl group connected to the $\eta^5$ ligand through a chain. These compounds are very useful since they can be used as a starting material for preparing more complex compounds comprising one or more transition metal atoms.

An object of the present invention is to provide metallocene compounds having an hydroxyl group connected to the $\eta^5$ ligand through a chain.

A further object of the present invention is to provide a process for obtaining these metallocene compounds.

DETAILED DESCRIPTION OF THE INVENTION

The present invention relates to metallocene compounds defined by the following formulas:

(I)

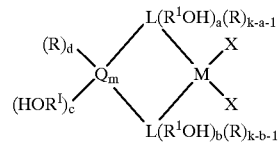
(II)

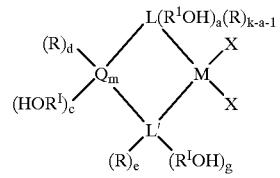
(III)

wherein:

L, equal to or different from each other, is selected from the group comprising: cyclopentadienyl, indenyl, tetrahydroindenyl, fluorenyl, octahydrofluorenyl and benzoindenyl;

each R is independently selected from hydrogen, $C_1$–$C_{20}$ alkyl, $C_3$–$C_{20}$ cycloalkyl, $C_6$–$C_{20}$ aryl, $C_3$–$C_{20}$ alkenyl, $C_7$–$C_{20}$ arylalkyl, $C_7$–$C_{20}$ alkylaryl, $C_8$–$C_{20}$ arylalkenyl, linear or branched, optionally substituted by 1 to 10 halogen atoms, or a group $SiR''_3$; each $R^I$ is independently a group $SiR''_2$ or a divalent aliphatic or aromatic hydrocarbon group containing from 1 to 20 carbon atoms, optionally containing from 1 to 5 heteroatoms of groups 14 to 16 of the periodic table of the elements and boron; preferably it is: $C_1$–$C_{20}$ alkylene, $C_3$–$C_{20}$ cycloalkylene, $C_6$–$C_{20}$ arylene, $C_7$–$C_{20}$ alkenyl, $C_7$–$C_{20}$ arylalkylene, or alkylarylene, linear or branched, or a group $SiR''_2$;

each Q is independently selected from B, C, Si, Ge, Sn;

M is a metal of group 3, 4 or 10 of the Periodic Table, Lanthanide or Actinide; preferably it is titanium, zirconium or hafnium;

each X is independently selected from: hydrogen, chlorine, bromine, $OR''$, $NR''_2$, $C_1$–$C_{20}$ alkyl or $C_6$–$C_{20}$ aryl;

each $R''$ is independently selected from $C_1$–$C_{20}$ alkyl, $C_3$–$C_{20}$ cycloalkyl, $C_6$–$C_{20}$ aryl, $C_3$–$C_{20}$ alkenyl, $C_7$–$C_{20}$ arylalkyl, $C_7$–$C_{20}$ arylalkenyl or $C_7$–$C_{20}$ alkylaryl, linear or branched; preferably $R''$ is methyl, ethyl, isopropyl;

$L'$ is N or O;

k depends on the type of L; more specifically when L is cyclopentadienyl k is equal to 5, when L is indenyl k is equal to 7, when L is fluorenyl or benzoindenyl k is equal to 9, when L is tetrahydroindenyl k is equal to 11 and when L is octahydrofluorenyl, k is equal to 17;

z is equal to 0, 1 or 2;

x is equal to 1, 2 or 3;

y is equal to 1, 2 or 3;

x+y+z is equal to the valence of M;

m is an integer which can assume the values 1, 2, 3 or 4;

a and b are integers whose value ranges from 0 to k-1;

f is an integer whose value ranges from 1 to k; preferably f is 1;

g is an integer whose value is 0 or 1;

c and e are equal to 0 or 1;

a+b+c is at least 1; preferably a+b+c is 1 or 2;

a+g+c is at least 1; preferably a+g+c is 1 or 2;

d is equal to 0, 1 or 2;

when Q is B, then c+d=1;

when Q is C, Si, Ge or Sn, then c+d=2;

when L' is N, then g+e=1;

when L' is O, then g=0 and e=0.

Non limiting examples of $R^I OH$ are:

$CH_2$—$CH_2$—OH; $CH_2$—$CH_2$—$CH_2$—OH; O—$CH_2$—$CH_2$—OH; $SiMe_2$—$CH_2$—$CH_2$—OH; $CH_2$—$C_5H_5$—$CH_2$—OH; $CH(C_2H_5)$—$CH_2$—OH; $C(CH_3)_2$—$(CH_3)_2$—OH; $CH(CH_3)$—$CH(CH_3)$—OH, $SiMe_2$—$CH_2$—$CH_2$—$CH_2$—OH.

Preferably $R^I$—OH is selected from $CH_2$—$CH_2$—OH, $CH_2$—$CH_2$—$CH_2$—OH, O—$CH_2$—$CH_2$—OH, $SiMe_2$—$CH_2$—$CH_2$—OH,. $SiMe_2$—$CH_2$—$CH_2$—$CH_2$—OH.

Preferred structures of compounds of formula I, II and III are the following:

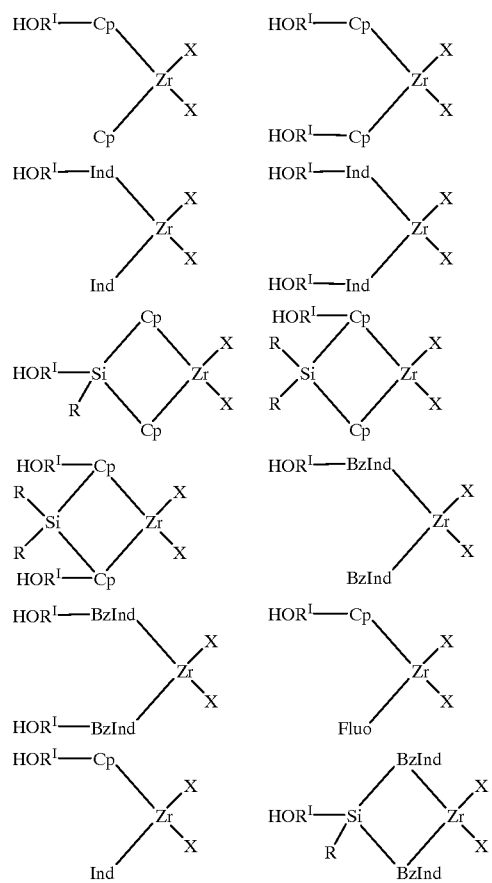

-continued

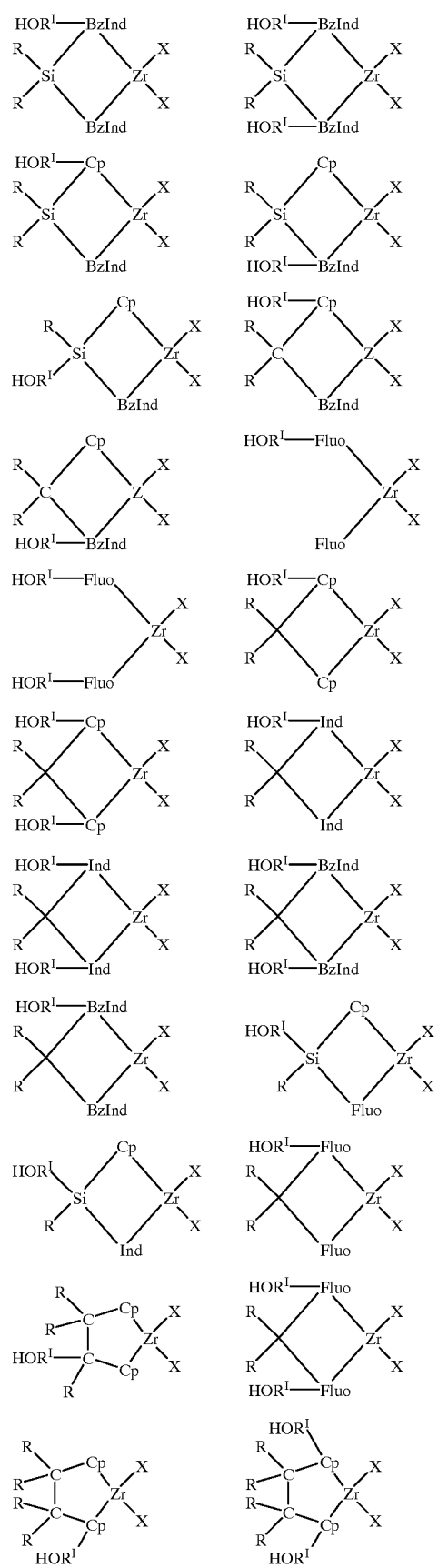

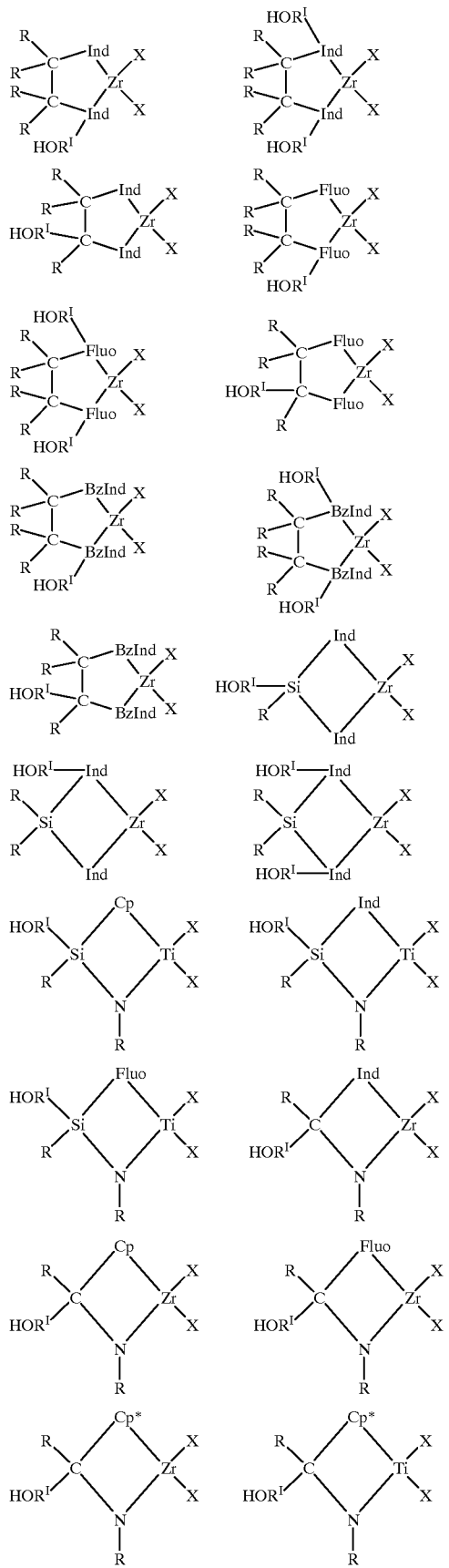
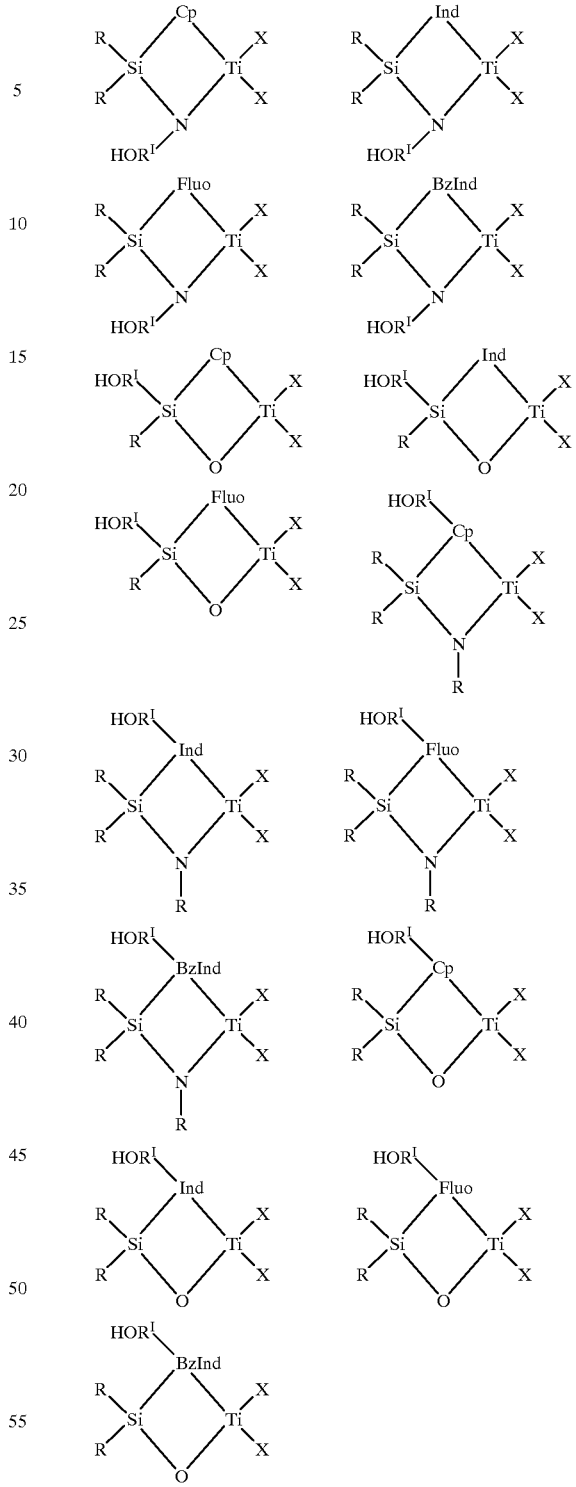

Cp, Ind, BzInd and Fluo indicate respectively a cyclopentadienyl, indenyl, benzoindenyl and fluorenyl ring optionally substituted by $C_1$–$C_{20}$ alkyl, $C_3$–$C_{20}$ cycloalkyl, $C_6$–$C_{20}$ aryl, $C_3$–$C_{20}$ alkenyl, $C_7$–$C_{20}$ arylalkyl, $C_8$–$C_{20}$ arylalkenyl or $C_7$–$C_{20}$ alkylaryl; the maximum number of substituents depends on the amount of hydrogen which can be substituted; R, $R^I$ and X have the above indicated meaning.

Preferred compounds for use in the present invention are the following:

bis(2-hydroxyethyl-cyclopentadienyl) zirconium dichloride;
(2-hydroxyethyl-cyclopentadienyl)(cyclopentadienyl) zirconium dichloride;
(2-hydroxyethyl-cyclopentadienyl)(indenyl) zirconium dichloride ;
(2-hydroxyethyl-cyclopentadienyl)(2-methyl-indenyl ) zirconium dichloride;
(2-hydroxyethyl-cyclopentadienyl)(fluorenyl) zirconium dichloride;
(2-hydroxyethyl-cyclopentadienyl)(9-methyl-fluorenyl) zirconium dichloride;
(2-hydroxyethyl-cyclopentadienyl) (pentamethylcyclopentadienyl) zirconium dichloride;
bis(3-hydroxypropyl-cyclopentadienyl) zirconium dichloride;
(3-hydroxypropyl-cyclopentadienyl)(cyclopentadienyl) zirconium dichloride;
(3-hydroxypropyl-cyclopentadienyl)(indenyl) zirconium dichloride;
(3-hydroxypropyl-cyclopentadienyl)(2-methyl-indenyl) zirconium dichloride;
(3-hydroxypropyl-cyclopentadienyl)(fluorenyl) zirconium dichloride;
(3-hydroxypropyl-cyclopentadienyl)(9-methyl-fluorenyl) zirconium dichloride;
(3-hydroxypropyl-cyclopentadienyl) (pentamethylcyclopentadienyl) zirconium dichloride;
bis(2-hydroxy - ethoxy-cyclopentadienyl) zirconium dichloride;
(2-hydroxy-ethoxy-cyclopentadienyl)(cyclopentadienyl) zirconium dichloride
(2-hydroxy-ethoxy-cyclopentadienyl)(1-indenyl) zirconium dichloride;
(2-hydroxy-ethoxy-cyclopentadienyl)(2-methyl-indenyl) zirconium dichloride;
(2-hydroxy-ethoxy-cyclopentadienyl)(fluorenyl) zirconium dichloride;
(2-hydroxy-ethoxy-cyclopentadienyl)(9-methyl-fluorenyl) zirconium dichloride;
(2-hydroxy-ethoxy-cyclopentadienyl) (pentamethylcyclopentadienyl) zirconium dichloride;
bis(2-hydroxy-ethyl-(dimethyl)silyl-cyclopentadienyl) zirconium dichloride;
(2-hydroxy-ethyl-(dimethyl)silyl-cyclopentadienyl) (cyclopentadienyl) zirconium dichloride;
(2-hydroxy-ethyl-(dimethyl)silyl-cyclopentadienyl) (indenyl) zirconium dichloride;
(2-hydroxy-ethyl-(dimethyl)silyl-cyclopentadienyl)(2-methyl-indenyl) zirconium dichloride;
(2-hydroxy-ethyl-(dimethyl)silyl-cyclopentadienyl) (fluorenyl) zirconium dichloride;
(2-hydroxy-ethyl-(dimethyl)silyl-cyclopentadienyl)(9-methyl-fluorenyl) zirconium dichloride;
(2-hydroxy-ethyl-(dimethyl)silyl-cyclopentadienyl) (pentamethylcyclopentadienyl) zirconium dichloride;
(3-hydroxy-propyl-(dimethyl)silyl-cyclopentadienyl) (cyclopentadienyl) zirconium dichloride;
(3-hydroxy-propyl-ethyl-(dimethyl)silyl-cyclopentadienyl) (indenyl) zirconium dichloride;
(3-hydroxy-propyl-ethyl-(di methyl)silyl-cyclopentadienyl) (2-methyl-indenyl) zirconium dichloride;
(3-hydroxy-propyl-ethyl-(dimethyl)silyl-cyclopentadienyl) (fluorenyl) zirconium dichloride;
(3-hydroxy-propyl-ethyl-(dimethyl)silyl-cyclopentadienyl) (9-methyl-fluorenyl) zirconium dichloride;
(3-hydroxy-propyl-ethyl-(dimethyl)silyl-cyclopentadienyl) (pentamethylcyclopentadienyl) zirconium dichloride;
bis(2-hydroxy-(dimethyl)silyl-cyclopentadienyl) zirconium dichloride;
(2-hydroxy-(dimethyl)silyl-cyclopentadienyl) (cyclopentadienyl) zirconium dichloride;
dimethylsilandiylbis(2-(2-hydroxyethyl)-cyclopentadienyl) zirconium dichloride;
dimethylsilandiylbis(3-(2-hydroxyethyl)-cyclopentadienyl) zirconium dichloride;
dimethylsilandiyl(3-(2-hydroxyethyl)-cyclopentadienyl) (cyclopentadienyl)zirconium dichloride;
dimethylsilandiyl(2-(2-hydroxyethyl)-cyclopentadienyl)(1-indenyl) zirconium dichloride;
dimethylsilandiyl(3-(2-hydroxyethyl)-cyclopentadienyl)(1-indenyl) zirconium dichloride;
dimethylsilandiyl(2-(2-hydroxyethyl)-cyclopentadienyl)(1-(2-methyl-indenyl)) zirconium dichloride;
dimethylsilandiyl(3-(2-hydroxyethyl)-cyclopentadienyl)(1-(2-methyl-indenyl)) zirconium dichloride;
dimethylsilandiyl(2-(2-hydroxyethyl)-cyclopentadienyl)(9-fluorenyl) zirconium dichloride;
dimethylsilandiyl(3-(2-hydroxyethyl)-cyclopentadienyl)(9-fluorenyl) zirconium dichloride;
dimethylsilandiyl(2-(2-hydroxyethyl)-cyclopentadienyl)(9-(2-methyl-fluorenyl)) zirconium dichloride;
dimethylsilandiyl(3-(2-hydroxyethyl)-cyclopentadienyl)(9-(2-methyl-fluorenyl)) zirconium dichloride;
dimethylsilandiyl(3-(2-hydroxyethyl)-cyclopentadienyl)(1-(2methylbenzoindenyl)) zirconium dichloride;
dimethylsilandiylbis(2-(3-hydroxypropyl)-cyclopentadienyl) zirconium dichloride;
dimethylsilandiylbis(3-(3-hydroxyropyl)-cyclopentadienyl) zirconium dichloride;
dimethylsilandiyl(3-(3-hydroxyropyl)-cyclopentadienyl) (cyclopentadienyl) zirconium dichloride;
dimethylsilandiyl(2-(3-hydroxypropyl)-cyclopentadienyl) (1-indenyl) zirconium dichloride;
dimethylsilandiyl(3-(3-hydroxyropyl)-cyclopentadienyl)(1-indenyl) zirconium dichloride;
dimethylsilandiyl(2-(3-hydroxypropyl)-cyclopentadienyl) (1-(2-methyl-indenyl)) zirconium dichloride;
dimethylsilandiyl(3-(3-hydroxyropyl)-cyclopentadienyl)(1-(2-methyl-indenyl)) zirconium dichloride;
dimethylsilandiyl(2-(3-hydroxypropyl)-cyclopentadienyl) (9-fluorenyl) zirconium dichloride;
dimethylsilandiyl(3-(3-hydroxyropyl)-cyclopentadienyl)(9-fluorenyl) zirconium dichloride;
dimethylsilandiyl(2-(3-hydroxypropyl)-cyclopentadienyl) (9-(2-methyl-fluorenyl)) zirconium dichloride;
dimethylsilandiyl(3-(3-hydroxyropyl)-cyclopentadienyl)(9-(2-methyl-fluorenyl)) zirconium dichloride;
dimethylsilandiyl(3-(3-hydroxyropyl)-cyclopentadienyl)(1-(2methylbenzoindenyl)) zirconium dichloride;
dimethylsilandiylbis(2-(2-hydroxy)-ethoxy-cyclopentadienyl) zirconium dichloride;
dimethylsilandiylbis(3-(2-hydroxy)-ethoxy-cyclopentadienyl) zirconium dichloride;
dimethylsilandiyl(2-(2-hydroxy)-ethoxy-cyclopentadienyl) (1-indenyl) zirconium dichloride;
dimethylsilandiyl(3-(2-hydroxy)-ethoxy-cyclopentadienyl) (1-indenyl) zirconium dichloride;
dimethylsilandiyl(2-(2-hydroxy)-ethoxy-cyclopentadienyl) (1-(2-methyl-indenyl)) zirconium dichloride;
dimethylsilandiyl(3-(2-hydroxy)-ethoxy-cyclopentadienyl) (1-(2-methyl-indenyl)) zirconium dichloride;
dimethylsilandiyl(2-(2-hydroxy)-ethoxy-cyclopentadienyl) (9-fluorenyl) zirconium dichloride;

dimethylsilandiyl(3-(2-hydroxy)-ethoxy-cyclopentadienyl)
(9-fluorenyl) zirconium dichloride;
dimethylsilandiyl(2-(2-hydroxy)-ethoxy-cyclopentadienyl)
(9-(2-methyl-fluorenyl)) zirconium dichloride;
dimethylsilandiyl(3-(2-hydroxy)-ethoxy-cyclopentadienyl)
(9-(2-methyl-fluorenyl)) zirconium dichloride;
dimethylsilandiylbis(2-(2-hydroxy-ethyl-(dimethyl)silyl)-
cyclopentadienyl) zirconium dichloride;
dimethylsilandiylbis(3-(2-hydroxy-ethyl-(dimethyl)silyl)-
cyclopentadienyl) zirconium dichloride;
dimethylsilandiyl(2-(2-hydroxy-ethyl-(dimethyl)silyl)-
cyclopentadienyl) (1-indenyl) zirconium dichloride;
dimethylsilandiyl(3-(2-hydroxy-ethyl-(dimethyl)silyl)-
cyclopentadienyl)(1-indenyl) zirconium dichloride;
dimethylsilandiyl(2-(2-hydroxy-ethyl-(dimethyl)silyl)-
cyclopentadienyl)(1-(2-methyl-indenyl)) zirconium
dichloride;
dimethylsilandiyl(3-(2-hydroxy-ethyl-(dimethyl)silyl)-
cyclopentadienyl)(1-(2-methyl-indenyl)) zirconium
dichloride;
dimethylsilandiyl(2-(2-hydroxy-ethyl-(dimethyl)silyl)-
cyclopentadienyl)(9-fluorenyl) zirconium dichloride;
dimethylsilandiyl(3-(2-hydroxy-ethyl-(dimethyl)silyl)-
cyclopentadienyl)(9-fluorenyl) zirconium dichloride;
dimethylsilandiyl(2-(2-hydroxy-ethyl-(dimethyl)silyl)-
cyclopentadienyl)(9-(2-methyl-fluorenyl)) zirconium
dichloride;
dimethylsilandiyl(3-(2-hydroxy-ethyl-(dimethyl)silyl)-
cyclopentadienyl)(9-(2-methyl-fluorenyl)) zirconium
dichloride;
dimethylsilandiyl(3-(2-hydroxy-(dimethyl)silyl)-
cyclopentadienyl)(1-indenyl) zirconium dichloride;
dimethylsilandiyl(3-(2-hydroxy-(dimethyl)silyl)-
cyclopentadienyl)( -(2-methylbenzoindenyl)) zirconium
dichloride;
dimethylsilandiylbis(3-(2-hydroxy-(dimethyl)silyl--
1indenyl) zirconium dichloride;
dimethylsilandiyl(3-(2-hydroxy-(dimethyl)silyl-1-indenyl)
(1-indenyl)zirconium dichloride;
isopropylidenebis(2-(2-hydroxyethyl)-cyclopentadienyl)
zirconium dichloride;
isopropylidenebis(3-(2-hydroxyethyl)-cyclopentadienyl)
zirconium dichloride;
isopropylidene(2-(2-hydroxyethyl)-cyclopentadienyl)(1-
indenyl) zirconium dichloride;
isopropylidene(3-(2-hydroxyethyl)-cyclopentadienyl)(1-
indenyl) zirconium dichloride;
isopropylidene(2-(2-hydroxyethyl)-cyclopentadienyl)(1-(2-
methyl-indenyl)) zirconium dichloride;
isopropylidene(3-(2-hydroxyethyl)-cyclopentadienyl)(1-(2-
methyl-indenyl)) zirconium dichloride;
isopropylidene(2-(2-hydroxyethyl)-cyclopentadienyl)(9-
fluorenyl) zirconium dichloride;
isopropylidene(3-(2-hydroxyethyl)-cyclopentadienyl)(9-
fluorenyl) zirconium dichloride;
isopropylidene(2-(2-hydroxyethyl)-cyclopentadienyl)(9-(2-
methyl-fluorenyl) ) zirconium dichloride;
isopropyidene(3-(2-hydroxyethyl)-cyclopentadienyl)(9-(2-
methyl-fluorenyl)) zirconium dichloride;
isopropylidene(3-(2-hydroxyethyl)-cyclopentadienyl)(1-
(2methylbenzoindenyl)) zirconium dichloride;
isopropylidenebis(2-(3-hydroxypropyl)-cyclopentadienyl)
zirconium dichloride;
isopropylidenebis(3-(3-hydroxyropyl)-cyclopentadienyl)
zirconium dichloride;
isopropylidene(2-(3-hydroxypropyl)-cyclopentadienyl)(1-
indenyl) zirconium dichloride;

isopropylidene(3-(3-hydroxyropyl)-cyclopentadienyl)(1-
indenyl) zirconium dichloride;
isopropylidene(2-(3-hydroxypropyl)-cyclopentadienyl)(1-
(2-methyl-indenyl)) zirconium dichloride;
isopropylidene(3-(3-hydroxyropyl)-cyclopentadienyl)(1-(2-
methyl-indenyl)) zirconium dichloride;
isopropylidene(2-(3-hydroxypropyl)-cyclopentadienyl)(9-
fluorenyl) zirconium dichloride;
isopropylidene(3-(3-hydroxyropyl)-cyclopentadienyl)(9-
fluorenyl) zirconium dichloride;
isopropylidene(2-(3-hydroxypropyl)-cyclopentadienyl)(9-
(2-methyl-fluorenyl)) zirconium dichloride;
isopropylidene(3-(3-hydroxyropyl)-cyclopentadienyl)(9-(2-
methyl-fluorenyl)) zirconium dichloride;
isopropylidene(3-(3-hydroxyropyl)-cyclopentadienyl)(1-
(2methylbenzoindenyl)) zirconium dichloride;
isopropylidenebis(2-(2-hydroxy-ethoxy)-cyclopentadienyl)
zirconium dichloride;
isopropylidenebis(3-(2-hydroxy-ethoxy)-cyclopentadienyl)
zirconium dichloride;
isopropylidene(2-(2-hydroxy-ethoxy)-cyclopentadienyl)(1-
indenyl) zirconium dichloride;
isopropylidene(3-(2-hydroxy-ethoxy)-cyclopentadienyl)(1-
indenyl) zirconium dichloride;
isopropylidene(2-(2-hydroxy-ethoxy)-cyclopentadienyl)(1-
(2-methyl-indenyl)) zirconium dichloride;
isopropylidene(3-(2-hydroxy-ethoxy)-cyclopentadienyl)(1-
(2-methyl-indenyl)) zirconium dichloride;
isopropylidene(2-(2-hydroxy-ethoxy)-cyclopentadienyl)(9-
fluorenyl) zirconium dichloride;
isopropylidene(3-(2-hydroxy-ethoxy)-cyclopentadienyl)(9-
fluorenyl) zirconium dichloride;
isopropylidene(2-(2-hydroxy-ethoxy)-cyclopentadienyl)(9-
(2-methyl-fluorenyl)) zirconium dichloride;
isopropylidene(3-(2-hydroxy-ethoxy)-cyclopentadienyl)(9-
(2-methyl-fluorenyl)) zirconium dichloride;
isopropylidenebis(2-(2-hydroxy-ethyl-(dimethyl)silyl)-
cyclopentadienyl) zirconium dichloride;
isopropylidenebis(3-(2-hydroxy-ethyl-(dimethyl)silyl)-
cyclopentadienyl) zirconium dichloride;
isopropylidene(2-(2-hydroxy-ethyl-(dimethyl)silyl)-
cyclopentadienyl)(1-indenyl) zirconium dichloride;
isopropylidene(3-(2-hydroxy-ethyl-(dimethyl)silyl)-
cyclopentadienyl)(1-indenyl) zirconium dichloride;
isopropylidene(2-(2-hydroxy-ethyl-(dimethyl)silyl)-
cyclopentadienyl)(1-(2-methyl-indenyl)) zirconium
dichloride;
isopropylidene(3-(2-hydroxy-ethyl-(dimethyl)silyl)-
cyclopentadienyl)(1-(2-methyl-indenyl)) zirconium
dichloride;
isopropylidene(2-(2-hydroxy-ethyl-(dimethyl)silyl)-
cyclopentadienyl)(9-fluorenyl) zirconium dichloride;
isopropylidene(3-(2-hydroxy-ethyl-(dimethyl)silyl)-
cyclopentadienyl)(9-fluorenyl) zirconium dichloride;
isopropylidene(2-(2-hydroxy-ethyl-(dimethyl)silyl)-
cyclopentadienyl)(9-(2-methyl-fluorenyl)) zirconium
dichloride;
isopropylidene(3-(2-hydroxy-ethyl-(dimethyl)silyl)-
cyclopentadienyl)(9-(2-methyl-fluorenyl)) zirconium
dichloride;
isopropylidene(2-(2-hydroxy-(dimethyl)silyl)-
cyclopentadienyl)(1-indenyl) zirconium dichloride;
isopropylidene(2-(2-hydroxy-(dimethyl)silyl)-
cyclopentadienyl)(1-(2-methylbenzoindenyl)) zirconium
dichloride;
ethylidenebis(2-(2-hydroxyethyl)-cyclopentadienyl) zirco-
nium dichloride;

ethylidenebis(3-(2-hydroxyethyl)-cyclopentadienyl) zirconium dichloride;
ethylidene(3-(2-hydroxyethyl)-cyclopentadienyl)(cyclopentadienyl) zirconium dichloride;
ethylidene(2-(2-hydroxyethyl)-cyclopentadienyl)(1-indenyl) zirconium dichloride;
ethylidene(3-(2-hydroxyethyl)-cyclopentadienyl)(1-indenyl) zirconium dichloride;
ethylidene(2-(2-hydroxyethyl)-cyclopentadienyl)(1-(2-methyl-indenyl)) zirconium dichloride;
ethylidene(3-(2-hydroxyethyl)-cyclopentadienyl)(1-(2-methyl-indenyl)) zirconium dichloride;
ethylidene(2-(2-hydroxyethyl)-cyclopentadienyl)(9-fluorenyl) zirconium dichloride;
ethylidene(3-(2-hydroxyethyl)-cyclopentadienyl)(9-fluorenyl) zirconium dichloride;
ethylidene(2-(2-hydroxyethyl)-cyclopentadienyl)(9-(2-methyl-fluorenyl)) zirconium dichloride;
ethylidene(3-(2-hydroxyethyl)-cyclopentadienyl)(9-(2-methyl-fluorenyl)) zirconium dichloride;
ethylidenebis(2-(3-hydroxypropyl)-cyclopentadienyl) zirconium dichloride;
ethylidenebis(3-(3-hydroxyropyl)-cyclopentadienyl) zirconium dichloride;
ethylidene(3-(3-hydroxyropyl)-cyclopentadienyl)(cyclopentadienyl) zirconium dichioride;
ethylidene(2-(3-hydroxypropyl)-cyclopentadienyl)(1-indenyl) zirconium dichloride;
ethylidene(3-(3-hydroxyropyl)-cyclopentadienyl)(1-indenyl) zirconium dichloride;
ethylidene(2-(3-hydroxypropyl)-cyclopentadienyl)(1-(2-methyl-indenyl)) zirconium dichloride;
ethylidene(3-(3-hydroxyropyl)-cyclopentadienyl)(1-(2-methyl-indenyl)) zirconium dichloride;
ethylidene(2-(3-hydroxypropyl)-cyclopentadienyl)(9-fluorenyl) zirconium dichloride;
ethylidene(3-(3-hydroxyropyl)-cyclopentadienyl)(9-fluorenyl) zirconium dichloride;
ethylidene(2-(3-hydroxypropyl)-cyclopentadienyl)(9-(2-methyl-fluorenyl)) zirconium dichloride;
ethylidene(3-(3-hydroxyropyl)-cyclopentadienyl)(9-(2-methyl-fluorenyl)) zirconium dichloride;
ethylidenebis(2-(2-hydroxy-ethoxy)-cyclopentadienyl) zirconium dichloride;
ethylidenebis(3-(2-hydroxy-ethoxy)-cyclopentadienyl) zirconium dichloride;
ethylidene(2-(2-hydroxy-ethoxy)-cyclopentadienyl)(1-indenyl) zirconium dichloride;
ethylidene(3-(2-hydroxy-ethoxy)-cyclopentadienyl)(1-indenyl) zirconium dichloride;
ethylidene(2-(2-hydroxy-ethoxy)-cyclopentadienyl)(1-(2-methyl-indenyl)) zirconium dichloride;
ethylidene(3-(2-hydroxy-ethoxy)-cyclopentadienyl)(1-(2-methyl-indenyl)) zirconium dichloride;
ethylidene(2-(2-hydroxy-ethoxy)-cyclopentadienyl)(9-fluorenyl) zirconium dichloride;
ethylidene(3-(2-hydroxy-ethoxy)-cyclopentadienyl)(9-fluorenyl) zirconium dichloride;
ethylidene(2-(2-hydroxy-ethoxy)-cyclopentadienyl)(9-(2-methyl-fluorenyl)) zirconium dichloride;
ethylidene(3-(2-hydroxy-ethoxy)-cyclopentadienyl)(9-(2-methyl-fluorenyl)) zirconium dichloride;
ethylidenebis(2-(2-hydroxy-ethyl-(dimethyl)silyl)-cyclopentadienyl) zirconium dichloride;
ethylidenebis(3-(2-hydroxy-ethyl-(dimethyl)silyl)-cyclopentadienyl) zirconium dichloride;
ethylidene(2-(2-hydroxy-ethyl-(dimethyl)silyl)-cyclopentadienyl)(1-indenyl) zirconium dichloride;
ethylidene(3-(2-hydroxy-ethyl-(dimethyl)silyl)-cyclopentadienyl)(1-indenyl) zirconium dichloride;
ethylidene(2-(2-hydroxy-ethyl-(dimethyl)silyl)-cyclopentadienyl)(1-(2-methyl-indenyl)) zirconium dichloride;
ethylidene(3-(2-hydroxy-ethyl-(dimethyl)silyl)-cyclopentadienyl)(1-(2-methyl-indenyl)) zirconium dichloride;
ethylidene(2-(2-hydroxy-ethyl-(dimethyl)silyl)-cyclopentadienyl)(9-fluorenyl) zirconium dichloride;
ethylidene(3-(2-hydroxy-ethyl-(dimethyl)silyl)-cyclopentadienyl)(9-fluorenyl) zirconium dichloride;
ethylidene(2-(2-hydroxy-ethyl-(dimethyl)silyl)-cyclopentadienyl)(9-(2-methyl-fluorenyl)) zirconium dichloride;
ethylidene(3-(2-hydroxy-ethyl-(dimethyl)silyl)-cyclopentadienyl)(9-(2-methyl-fluorenyl)) zirconium dichloride;
dimethylsilandiylbis(1-(2-(2-hydroxyethyl)-indenyl)) zirconium dichloride;
dimethylsilandiylbis(1-(3-(2-hydroxyethyl)-indenyl)) zirconium dichloride;
dimethylsilandiyl(1-(2-(2-hydroxyethyl)-indenyl))(1-indenyl) zirconium dichloride;
dimethylsilandiyl(1-(3-(2-hydroxyethyl)-indenyl))(1-indenyl) zirconium dichloride;
dimethylsilandiyl(1-(2-(2-hydroxyethyl)-indenyl))(1-(2-methyl-indenyl)) zirconium dichloride;
dimethylsilandiyl(1-(3-(2-hydroxyethyl)-indenyl))(1-(2-methyl-indenyl)) zirconium dichloride;
dimethylsilandiyl(1-(2-(2-hydroxyethyl)-indenyl))(9-fluorenyl) zirconium dichloride;
dimethylsilandiyl(1-(3-(2-hydroxyethyl)-indenyl))(9-fluorenyl) zirconium dichloride;
dimethylsilandiyl(1-(2-(2-hydroxyethyl)-indenyl))(9-(2-methyl-fluorenyl)) zirconium dichloride;
dimethylsilandiyl(1-(3-(2-hydroxyethyl)-indenyl))(9-(2-methyl-fluorenyl)) zirconium dichloride;
dimethylsilandiylbis(1-(2-(3-hydroxypropyl)-indenyl)) zirconium dichloride;
dimethylsilandiylbis(1-(3-(3-hydroxyropyl)-indenyl)) zirconium dichloride;
dimethylsilandiyl(1-(2-(3-hydroxypropyl)-indenyl))(1-indenyl) zirconium dichloride;
dimethylsilandiyl(1-(3-(3-hydroxyropyl)-indenyl))(1-indenyl) zirconium dichloride;
dimethylsilandiyl(1-(2-(3-hydroxypropyl)-indenyl))(1-(2-methyl-indenyl)) zirconium dichloride;
dimethylsilandiyl(1-(3-(3-hydroxyropyl)-indenyl))(1-(2-methyl-indenyl)) zirconium dichloride;
dimethylsilandiyl(1-(2-(3-hydroxypropyl)-indenyl))(9-fluorenyl) zirconium dichloride;
dimethylsilandiyl(1-(3-(3-hydroxyropyl)-indenyl))(9-fluorenyl) zirconium dichloride;
dimethylsilandiyl(1-(2-(3-hydroxypropyl)-indenyl))(9-(2-methyl-fluorenyl)) zirconium dichloride;
dimethylsilandiyl(1-(3-(3-hydroxyropyl)-indenyl))(9-(2-methyl-fluorenyl)) zirconium dichloride;
dimethylsilandiylbis(1-(2-(2-hydroxy-ethoxy-indenyl)) zirconium dichloride;
dimethylsilandiylbis(1-(3-(2-hydroxy-ethoxy-indenyl)) zirconium dichloride;
dimethylsilandiyl(1-(2-(2-hydroxy-ethoxy-indenyl))(1-indenyl) zirconium dichloride;
dimethylsilandiyl(1-(3-(2-hydroxy-ethoxy-indenyl))(1-indenyl) zirconium dichloride;
dimethylsilandiyl(1-(2-(2-hydroxy-ethoxy-indenyl))(1-(2-methyl-indenyl)) zirconium dichloride;

dimethylsilandiyl(1-(3-(2-hydroxy-ethoxy-indenyl))(1-(2-methyl-indenyl)) zirconium dichloride;

dimethylsilandiyl(1-(2-(2-hydroxy-ethoxy-indenyl))(9-fluorenyl) zirconium dichloride;

dimethylsilandiyl(1-(3-(2-hydroxy-ethoxy-indenyl))(9-fluorenyl) zirconium dichloride;

dimethylsilandiyl(1-(2-(2-hydroxy-ethoxy-indenyl))(9-(2-methyl-fluorenyl)) zirconium dichloride;

dimethylsilandiyl(1-(3-(2-hydroxy-ethoxy-indenyl))(9-(2-methyl-fluorenyl)) zirconium dichloride;

dimethylsilandiylbis(1-(2-(2-hydroxy-ethyl-(dimethyl)silyl-indenyl)) zirconium dichloride;

dimethylsilandiylbis(1-(3-(2-hydroxy-ethyl-(dimethyl)silyl-indenyl)) zirconium dichloride;

dimethylsilandiyl(1-(2-(2-hydroxy-ethyl-(dimethyl)silyl-indenyl))(1-indenyl) zirconium dichloride;

dimethylsilandiyl(1-(3-(2-hydroxy-ethyl-(dimethyl)silyl-indenyl))(1-indenyl) zirconium dichloride;

dimethylsilandiyl(1-(2-(2-hydroxy-ethyl-(dimethyl)silyl-indenyl))(1-(2-methyl-indenyl)) zirconium dichloride;

dimethylsilandiyl(1-(3-(2-hydroxy-ethyl-(dimethyl)silyl-indenyl))(1-(2-methyl-indenyl)) zirconium dichloride;

dimethylsilandiyl(1-(2-(2-hydroxy-ethyl-(dimethyl)silyl-indenyl))(9-fluorenyl) zirconium dichloride;

dimethylsilandiyl(1-(3-(2-hydroxy-ethyl-(dimethyl)silyl-indenyl))(9-fluorenyl) zirconium dichloride;

dimethylsilandiyl(1-(2-(2-hydroxy-ethyl-(dimethyl)silyl-indenyl))(9-(2-methyl-fluorenyl)) zirconium dichloride;

dimethylsilandiyl(1-(3-(2-hydroxy-ethyl-(dimethyl)silyl-indenyl))(9-(2-methyl-fluorenyl)) zirconium dichloride;

isopropylidenebis(1-(2-(2-hydroxyethyl)-indenyl)) zirconium dichloride;

isopropylidenebis(1-(3-(2-hydroxyethyl)-indenyl)) zirconium dichioride;

isopropylidene(1-(2-(2-hydroxyethyl)-indenyl))(1-indenyl) zirconium dichloride;

isopropylidene(1-(3-(2-hydroxyethyl)-indenyl))(1-indenyl) zirconium dichloride;

isopropylidene(1-(2-(2-hydroxyethyl)-indenyl))(1-(2-methyl-indenyl)) zirconium dichloride;

isopropylidene(1-(3-(2-hydroxyethyl)-indenyl))(1-(2-methyl-indenyl)) zirconium dichloride;

isopropylidene(1-(2-(2-hydroxyethyl)-indenyl))(9-fluorenyl) zirconium dichloride;

isopropylidene(1-(3-(2-hydroxyethyl)-indenyl))(9-fluorenyl) zirconium dichloride;

isopropylidene(1-(2-(2-hydroxyethyl)-indenyl))(9-(2-methyl-fluorenyl)) zirconium dichloride;

isopropylidene(1-(3-(2-hydroxyethyl)-indenyl))(9-(2-methyl-fluorenyl)) zirconium dichloride;

isopropylidenebis(1-(2-(3-hydroxypropyl)-indenyl)) zirconium dichloride;

isopropylidenebis(1-(3-3-hydroxyropyl-indenyl)) zirconium dichloride;

isopropylidene(1-(2-(3-hydroxypropyl)-indenyl))(1-indenyl) zirconium dichloride;

isopropylidene(1-(3-3-hydroxyropyl-indenyl))(1-indenyl) zirconium dichloride;

isopropylidene(1-(2-(3-hydroxypropyl)-indenyl))(1-(2-methyl-indenyl)) zirconium dichloride;

isopropylidene(1-(3-3-hydroxyropyl-indenyl))(1-(2-methyl-indenyl)) zirconium dichloride;

isopropylidene(1-(2-(3-hydroxypropyl)-indenyl))(9-fluorenyl) zirconium dichloride;

isopropylidene(1-(3-3-hydroxyropyl-indenyl))(9-fluorenyl) zirconium dichloride;

isopropylidene(1-(2-(3-hydroxypropyl)-indenyl))(9-(2-methyl-fluorenyl)) zirconium dichloride;

isopropylidene(1-(3-3-hydroxyropyl-indenyl))(9-(2-methyl-fluorenyl)) zirconium dichloride;

isopropylidenebis(1-(2-(2-hydroxy-ethoxy-indenyl)) zirconium dichloride;

isopropylidenebis(1-(3-(2-hydroxy-ethoxy-indenyl)) zirconium dichloride;

isopropylidene(1-(2-(2-hydroxy-ethoxy-indenyl))(1-indenyl) zirconium dichloride;

isopropylidene(1-(3-(2-hydroxy-ethoxy-indenyl))(1-indenyl) zirconium dichloride;

isopropylidene(1-(2-(2-hydroxy-ethoxy-indenyl))(1-(2-methyl-indenyl)) zirconium dichloride;

isopropylidene(1-(3-(2-hydroxy-ethoxy-indenyl))(1-(2-methyl-indenyl)) zirconium dichloride;

isopropylidene(1-(2-(2-hydroxy-ethoxy-indenyl))(9-fluorenyl) zirconium dichloride;

isopropylidene(1-(3-(2-hydroxy-ethoxy-indenyl))(9-fluorenyl) zirconium dichloride;

isopropylidene(1-(2-(2-hydroxy-ethoxy-indenyl))(9-(2-methyl-fluorenyl)) zirconium dichloride;

isopropylidene(1-(3-(2-hydroxy-ethoxy-indenyl))(9-(2-methyl-fluorenyl)) zirconium dichloride;

isopropylidenebis(1-(2-(2-hydroxy-ethyl-(dimethyl)silyl-indenyl)) zirconium dichioride;

isopropylidenebis(1-(3-(2-hydroxy-ethyl-(dimethyl)silyl-indenyl)) zirconium dichloride;

isopropylidene(1-(2-(2-hydroxy-ethyl-(dimethyl)silyl-indenyl))(1-indenyl) zirconium dichloride;

isopropylidene(1-(3-(2-hydroxy-ethyl-(dimethyl)silyl-indenyl))(1-indenyl) zirconium dichloride;

isopropylidene(1-(2-(2-hydroxy-ethyl-(dimethyl)silyl-indenyl))(1-(2-methyl-indenyl)) zirconium dichloride;

isopropylidene(1-(3-(2-hydroxy-ethyl-(dimethyl)silyl-indenyl))(1-(2-methyl-indenyl)) zirconium dichloride;

isopropylidene(1-(2-(2-hydroxy-ethyl-(dimethyl)silyl-indenyl))(9-fluorenyl) zirconium dichloride;

isopropylidene(1-(3-(2-hydroxy-ethyl-(dimethyl)silyl-indenyl))(9-fluorenyl) zirconium dichloride;

isopropylidene(1-(2-(2-hydroxy-ethyl-(dimethyl)silyl-indenyl))(9-(2-methyl-fluorenyl)) zirconium dichloride;

isopropylidene(1-(3-(2-hydroxy-ethyl-(dimethyl)silyl-indenyl))(9-(2-methyl-fluorenyl)) zirconium dichloride;

ethylidenebis(1-(2-(2-hydroxyethyl)-indenyl)) zirconium dichloride;

ethylidenebis(1-(3-(2-hydroxyethyl)-indenyl)) zirconium dichloride;

ethylidene(1-(2-(2-hydroxyethyl)-indenyl))(1-indenyl) zirconium dichloride;

ethylidene(1-(3-(2-hydroxyethyl)-indenyl))(1-indenyl) zirconium dichloride;

ethylidene(1-(2-(2-hydroxyethyl)-indenyl))(1-(2-methyl-indenyl)) zirconium dichloride;

ethylidene(1-(3-(2-hydroxyethyl)-indenyl))(1-(2-methyl-indenyl)) zirconium dichloride;

ethylidene(1-(2-(2-hydroxyethyl)-indenyl))(9-fluorenyl) zirconium dichloride;

ethylidene(1-(3-(2-hydroxyethyl)-indenyl))(9-fluorenyl) zirconium dichloride;

ethylidene(1-(2-(2-hydroxyethyl)-indenyl))(9-(2-methyl-fluorenyl)) zirconium dichloride;

ethylidene(1-(3-(2-hydroxyethyl)-indenyl))(9-(2-methyl-fluorenyl)) zirconium dichloride;

ethylidenebis(1-(2-(3-hydroxypropyl)-indenyl)) zirconium dichloride;

ethylidenebis(1-(3-3-hydroxyropyl-indenyl)) zirconium dichloride;

ethylidene(1-(2-(3-hydroxypropyl)-indenyl))(1-indenyl) zirconium dichloride;

ethylidene(1-(3-3-hydroxyropyl-indenyl))(1-indenyl) zirconium dichloride;
ethylidene(1-(2-(3-hydroxypropyl)-indenyl))(1-(2-methyl-indenyl)) zirconium dichloride;
ethylidene(1-(3-3-hydroxyropyl-indenyl))(1-(2-methyl-indenyl)) zirconium dichloride;
ethylidene(1-(2-(3-hydroxypropyl)-indenyl))(9-fluorenyl) zirconium dichloride;
ethylidene(1-(3-3-hydroxyropyl-indenyl))(9-fluorenyl) zirconium dichloride; dichloride;
ethylidenebis(1-(2-(2-hydroxy-ethoxy-indenyl)) zirconium dichloride;
ethylidenebis(1-(3-(2-hydroxy-ethoxy-indenyl)) zirconium dichloride;
ethylidene(1-(2-(2-hydroxy-ethoxy-indenyl))(1-indenyl) zirconium dichloride;
ethylidene(1-(3-(2-hydroxy-ethoxy-indenyl))(1-indenyl) zirconium dichloride;
ethylidene(1-(2-(2-hydroxy-ethoxy-indenyl))(1-(2-methyl-indenyl)) zirconium dichloride;
ethylidene(1-(3-(2-hydroxy-ethoxy-indenyl))(1-(2-methyl-indenyl)) zirconium dichloride;
ethylidene(1-(2-(2-hydroxy-ethoxy-indenyl))(9-fluorenyl) zirconium dichloride;
ethylidene(1-(3-(2-hydroxy-ethoxy-indenyl))(9-fluorenyl) zirconium dichloride;
ethylidene(1-(2-(2-hydroxy-ethoxy-indenyl))(9-(2-methyl-fluorenyl)) zirconium dichloride;
ethylidene(1-(3-(2-hydroxy-ethoxy-indenyl))(9-(2-methyl-fluorenyl)) zirconium dichloride;
ethylidenebis(1-(2-(2-hydroxy-ethyl-(dimethyl)silyl-indenyl)) zirconium dichloride;
ethylidenebis(1-(3-(2-hydroxy-ethyl-(dimethyl)silyl-indenyl)) zirconium dichloride;
ethylidene(1-(2-(2-hydroxy-ethyl-(dimethyl)silyl-indenyl))(1-indenyl) zirconium dichloride;
ethylidene(1-(3-(2-hydroxy-ethyl-(dimethyl)silyl-indenyl))(1-indenyl) zirconium dichloride;
ethylidene(1-(2-(2-hydroxy-ethyl-(dimethyl)silyl-indenyl))(1-(2-methyl-indenyl)) zirconium dichloride;
ethylidene(1-(3-(2-hydroxy-ethyl-(dimethyl)silyl-indenyl))(1-(2-methyl-indenyl)) zirconium dichloride;
ethylidene(1-(2-(2-hydroxy-ethyl-(dimethyl)silyl-indenyl))(9-fluorenyl) zirconium dichloride;
ethylidene(1-(3-(2-hydroxy-ethyl-(dimethyl)silyl-indenyl))(9-fluorenyl) zirconium dichloride;
ethylidene(1-(2-(2-hydroxy-ethyl-(dimethyl)silyl-indenyl))(9-(2-methyl-fluorenyl)) zirconium dichloride;
ethylidene(1-(3-(2-hydroxy-ethyl-(dimethyl)silyl-indenyl))(9-(2-methyl-fluorenyl)) zirconium dichloride;
dimethylsilylenebis(9-(1-(2-hydroxyethyl)-fluorenyl)) zirconium dichloride;
dimethylsilylene(9-(1-(2-hydroxyethyl)-fluorenyl))(cyclopentadienyl) zirconium dichloride;
dimethylsilylene(9-(1-(2-hydroxyethyl)-fluorenyl))(1-(2-methyl-indenyl)) zirconium dichloride;
dimethylsilylene(9-(1-(2-hydroxyethyl)-fluorenyl))(1-indenyl) zirconium dichloride;
dimethylsilylene(9-(1-(2-hydroxyethyl)-fluorenyl))(9-(2-methyl-fluorenyl)) zirconium dichloride;
dimethylsilylenebis(9-(1-(3-hydroxyropyl)- fluorenyl)) zirconium dichloride;
dimethylsilylene(9-(1-(3-hydroxyropyl)-fluorenyl))(9-fluorenyl) zirconium dichloride;
dimethylsilylene(9-(1-(3-hydroxyropyl)-fluorenyl))(1-(2-methyl-indenyl)) zirconium dichloride;
dimethylsilylene(9-(1-(3-hydroxyropyl)-fluorenyl))(1-indenyl) zirconium dichloride;
dimethylsilylene(9-(1-(3-hydroxyropyl)-fluorenyl))(9-(2-methyl-fluorenyl)) zirconium dichloride;
dimethylsilylenebis(9-(1-(2-hydroxy-ethoxy)-fluorenyl)) zirconium dichloride;
dimethylsilylene(9-(1-(2-hydroxy-ethoxy)-fluorenyl))(9-fluorenyl) zirconium dichloride;
dimethylsilylene(9-(1-(2-hydroxy-ethoxy)-fluorenyl))(1-(2-methyl-indenyl)) zirconium dichloride;
dimethylsilylene(9-(1-(2-hydroxy-ethoxy)-fluorenyl))(1-indenyl) zirconium dichloride;
dimethylsilylene(9-(1-(2-hydroxy-ethoxy)-fluorenyl))(9-(2-methyl-fluorenyl)) zirconium dichloride;
dimethylsilylenebis(9-(1-(2-hydroxy-ethyl-(dimethyl)silyl-fluorenyl)) zirconium dichloride;
dimethylsilylene(9-(1-(2-hydroxy-ethyl-(dimethyl)silyl-fluorenyl))(9-fluorenyl) zirconium dichloride;
dimethylsilylene(9-(1-(2-hydroxy-ethyl-(dimethyl)silyl-fluorenyl))(1-(2-methyl-indenyl)) zirconium dichloride;
dimethylsilylene(9-(1-(2-hydroxy-ethyl-(dimethyl)silyl-fluorenyl))(1-indenyl) zirconium dichloride;
dimethylsilylene(9-(1-(2-hydroxy-ethyl-(dimethyl)silyl-fluorenyl))(9-(2-methyl-fluorenyl)) zirconium dichloride;
isopropylidenebis(9-(1-(2-hydroxyethyl)-fluorenyl)) zirconium dichloride;
isopropylidene(9-(1-(2-hydroxyethyl)-fluorenyl))(9-fluorenyl) zirconium dichloride;
isopropylidene(9-(1-(2-hydroxyethyl)-fluorenyl))(1-(2-methyl-indenyl)) zirconium dichloride;
isopropylidene(9-(1-(2-hydroxyethyl)-fluorenyl))(1-indenyl) zirconium dichloride;
isopropylidene(9-(1-(2-hydroxyethyl)-fluorenyl))(9-(2-methyl-fluorenyl)) zirconium dichloride;
isopropylidenebis(9-(1-(3-hydroxyropyl)-fluorenyl)) zirconium dichloride;
isopropylidene(9-(1-(3-hydroxyropyl)-fluorenyl))(9-fluorenyl) zirconium dichloride;
isopropylidene(9-(1-(3-hydroxyropyl)-fluorenyl))(1-(2-methyl-indenyl)) zirconium dichloride;
isopropylidene(9-(1-(3-hydroxyropyl)-fluorenyl))(1-indenyl) zirconium dichloride;
isopropylidene(9-(1-(3-hydroxyropyl)-fluorenyl))(9-(2-methyl-fluorenyl)) zirconium dichloride;
isopropylidenebis(9-(1-(2-hydroxy-ethoxy)-fluorenyl)) zirconium dichloride;
isopropylidene(9-(1-(2-hydroxy-ethoxy)-fluorenyl))(9-fluorenyl) zirconium dichloride;
isopropylidene(9-(1-(2-hydroxy-ethoxy)-fluorenyl))(1-(2-methyl-indenyl)) zirconium dichloride;
isopropylidene(9-(1-(2-hydroxy-ethoxy)-fluorenyl))(1-indenyl) zirconium dichloride;
isopropylidene(9-(1-(2-hydroxy-ethoxy)-fluorenyl))(9-(2-methyl-fluorenyl)) zirconium dichloride;
isopropylidenebis(9-(1-(2-hydroxy-ethyl-(dimethyl)silyl-fluorenyl)) zirconium dichloride;
isopropylidene(9-(1-(2-hydroxy-ethyl-(dimethyl)silyl-fluorenyl))(9-fluorenyl) zirconium dichloride;
isopropylidene(9-(1-(2-hydroxy-ethyl-(dimethyl)silyl-fluorenyl))(1-(2-methyl-indenyl)) zirconium dichloride;
isopropylidene(9-(1-2-hydroxy-ethyl-(dimethyl)silyl-fluorenyl))(1-indenyl) zirconium dichloride;
isopropylidene(9-(1-2-hydroxy-ethyl-(dimethyl)silyl-fluorenyl))(9-(2-methyl-fluorenyl)) zirconium dichloride;
ethylidenebis(9-(1-(2-hydroxyethyl-fluorenyl)) zirconium dichloride;
ethylidene(9-(1-(2-hydroxyethyl-fluorenyl))(9-fluorenyl) zirconium dichloride;
ethylidene(9-(1-(2-hydroxyethyl-fluorenyl))(1-(2-methyl-indenyl)) zirconium dichloride;

ethylidene(9-(1-(2-hydroxyethyl-fluorenyl))(1-indenyl) zirconium dichloride;
ethylidene(9-(1-(2-hydroxyethyl-fluorenyl))(9-(2-methyl-fluorenyl)) zirconium dichloride;
ethylidenebis(9-(1-(3-hydroxyropyl-fluorenyl)) zirconium dichloride;
ethylidene(9-(1-(3-hydroxyropyl-fluorenyl))(9-fluorenyl) zirconium dichloride;
ethylidene(9-(1-(3-hydroxyropyl-fluorenyl))(1-(2-methyl-indenyl)) zirconium dichloride;
ethylidene(9-(1-(3-hydroxyropyl-fluorenyl))(1-indenyl) zirconium dichloride;
ethylidene(9-(1-(3-hydroxyropyl-fluorenyl))(9-(2-methyl-fluorenyl)) zirconium dichloride;
ethylidenebis(9-(1-(2-hydroxy-ethoxy-fluorenyl)) zirconium dichloride;
ethylidene(9-(1-(2-hydroxy-ethoxy-fluorenyl))(9-fluorenyl) zirconium dichloride;
ethylidene(9-(1-(2-hydroxy-ethoxy-fluorenyl))(1-(2-methyl-indenyl)) zirconium dichloride;
ethylidene(9-(1-(2-hydroxy-ethoxy-fluorenyl))(1-indenyl) zirconium dichloride;
ethylidene(9-(1-(2-hydroxy-ethoxy-fluorenyl))(9-(2-methyl-fluorenyl)) zirconium dichloride;
ethylidenebis(9-(1-(2-hydroxy-ethyl-(dimethyl)silyl-fluorenyl)) zirconium dichloride;
ethylidene(9-(1-(2-hydroxy-ethyl-(dimethyl)silyl-fluorenyl))(9-fluorenyl) zirconium dichloride;
ethylidene(9-(1-(2-hydroxy-ethyl-(dimethyl)silyl-fluorenyl))(1-(2-methyl-indenyl)) zirconium dichloride;
ethylidene(9-(1-(2-hydroxy-ethyl-(dimethyl)silyl-fluorenyl))(1-indenyl) zirconium dichloride;
ethylidene(9-(1-(2-hydroxy-ethyl-(dimethyl)silyl-fluorenyl))(9-(2-methyl-fluorenyl)) zirconium dichloride;
2-hydroxyethyl(methyl)silandiylbis(cyclopentadienyl) zirconium dichloride;
2-hydroxyethyl(methyl)silandiylbis(9-fluorenyl) zirconium dichloride;
2-hydroxyethyl(methyl)silandiyl(cyclopentadienyl)(1-indenyl) zirconium dichloride;
2-hydroxyethyl(methyl)silandiyl(cyclopentadienyl)(1-(2-methyl-indenyl)) zirconium dichloride;
2-hydroxyethyl(methyl)silandiyl(cyclopentadienyl)(9-fluorenyl) zirconium dichloride;
2-hydroxyethyl(methyl)silndiyl(cyclopentadienyl)(9-(2-methyl-fluorenyl)) zirconium dichloride;
2-hydroxyethyl(methyl)silandiylbis(1-indenyl) zirconium dichloride;
2-hydroxyethyl(methyl)silandiyl(cyclopentadienyl)(1-(2-methylbenzoindenyl)) zirconium dichloride;
2-hydroxyethyl(methyl)silandiylbis(1-(2-methylbenzoindenyl)) zirconium dichloride;
3-hydroxyropyl(methyl)silandiylbis(cyclopentadienyl) zirconium dichloride;
3-hydroxyropyl(methyl)silandiylbis(9-fluorenyl) zirconium dichloride;
3-hydroxyropyl(methyl)silandiyl(cyclopentadienyl)(1-indenyl) zirconium dichloride;
3-hydroxyropyl(methyl)silandiyl(cyclopentadienyl)(1-(2-methyl-indenyl)) zirconium dichloride;
3-hydroxyropyl(methyl)silandiyl(cyclopentadienyl)(9-fluorenyl) zirconium dichloride;
3-hydroxyropyl(methyl)silandiyl(cyclopentadienyl)(9-(2-methyl-fluorenyl)) zirconium dichloride;
3-hydroxyropyl(methyl)silandiylbis(1-indenyl) zirconium dichloride;
3-hydroxyropyl(methyl)silandiyl(cyclopentadienyl)(1-(2-methylbenzoindenyl)) zirconium dichloride;
2-hydroxy-ethoxy(methyl)silandiylbis(cyclopentadienyl) zirconium dichloride;
2-hydroxy-ethoxy(methyl)silandiyl(cyclopentadienyl)(1-indenyl) zirconium dichloride;
2-hydroxy-ethoxy(methyl)silandiyl(cyclopentadienyl)(1-(2-methyl-indenyl)) zirconium dichloride;
2-hydroxy-ethoxy(methyl)silandiyl(cyclopentadienyl)(9-fluorenyl) zirconium dichloride;
2-hydroxy-ethoxy(methyl)silandiyl(cyclopentadienyl)(9-(2-methyl-fluorenyl)) zirconium dichloride;
2-hydroxy-ethyl-(dimethyl)silyl-(methyl)silandiylbis(cyclopentadienyl) zirconium dichloride;
2-hydroxy-ethyl-(dimethyl)silyl-(methyl)silandiyl(cyclopentadienyl)(1-indenyl) zirconium dichloride;
2-hydroxy-ethyl-(dimethyl)silyl-(methyl)silandiyl(cyclopentadienyl)(1-(2-methyl-indenyl)) zirconium dichloride;
2-hydroxy-ethyl-(dimethyl)silyl-(methyl)silandiyl(cyclopentadienyl)(9-fluorenyl) zirconium dichloride;
2-hydroxy-ethyl-(dimethyl)silyl-(methyl)silandiyl(cyclopentadienyl)(9-(2-methyl-fluorenyl)) zirconium dichloride;
2-hydroxy-ethoxy-(methyl)methylidenebis(cyclopentadienyl) zirconium dichloride;
2-hydroxy-ethoxy-(methyl)methylidene(cyclopentadienyl)(1-indenyl) zirconium dichloride;
2-hydroxy-ethoxy-(methyl)methylidene(cyclopentadienyl)(1-(2-methyl-indenyl)) zirconium dichloride;
2-hydroxy-ethoxy-(methy)methylidene(cyclopentadienyl)(9-fluorenyl) zirconium dichloride;
2-hydroxy-ethoxy-(methyl)methylidene(cyclopentadienyl)(9-(2-methyl-fluorenyl)) zirconium dichloride;
2-hydroxy-ethyl-(dimethyl)silyl-(methyl)methylidenebis(cyclopentadienyl) zirconium dichloride;
2-hydroxy-ethyl-(dimethyl)silyl-(methyl)methylidene(cyclopentadienyl)(1-indenyl) zirconium dichloride;
2-hydroxy-ethyl-(dimethyl)silyl-(methyl)methylidene(cyclopentadienyl)(1-(2-methylindenyl)) zirconium dichloride;
2-hydroxy-ethyl-(dimethyl)silyl-(methyl)methylidene(cyclopentadienyl)(9-fluorenyl) zirconium dichloride;
2-hydroxy-ethyl-(dimethyl)silyl-(methyl)methylidene(cyclopentadienyl)(9-(2-methylfluorenyl)) zirconium dichloride;
2-hydroxy-ethyl-(dimethyl)silyl-(methyl)methylidenebis(1-indenyl) zirconium dichloride;
1-(2-hydroxyethyl)-ethylidenebis(cyclopentadienyl) zirconium dichloride;
1-(2-hydroxyethyl)-ethylidene-1-(cyclopentadienyl)-2-(1-indenyl) zirconium dichloride;
1-(2-hydroxyethyl)-ethylidene-1-(cyclopentadienyl)-2-(1-(2-methyl-indenyl)) zirconium dichloride;
1-(2-hydroxyethyl)-ethylidene-1-(cyclopentadienyl)-2-(9-fluorenyl) zirconium dichloride;
1-(2-hydroxyethyl)-ethylidene-1-(cyclopentadienyl)-2-(9-(2-methyl-fluorenyl)) zirconium dichloride;
1-(2-hydroxyethyl)-ethylidenebis(1-indenyl) zirconium dichloride;
1-(3-hydroxypropyl)-ethylidenebis(cyclopentadienyl) zirconium dichloride;
1-(3-hydroxypropyl)-ethylidene-1-(cyclopentadienyl)-2-(1-indenyl) zirconium dichloride;
1-(3-hydroxypropyl)-ethylidene-1-(cyclopentadienyl)-2-(1-(2-methyl-indenyl)) zirconium dichloride;
1-(3-hydroxypropyl)-ethylidene-1-(cyclopentadienyl)-2-(9-fluorenyl) zirconium dichloride;
1-(3-hydroxypropyl)-ethylidene-1-(cyclopentadienyl)-2-(9-(2-methyl-fluorenyl)) zirconium dichloride;

1-(3-hydroxypropyl)-ethylidenebis(1-indenyl) zirconium dichloride;
1-(2-hydroxyethoxy)-ethylidenebis(cyclopentadienyl) zirconium dichloride;
1-(2-hydroxyethoxy)-ethylidene-1-(cyclopentadienyl)-2-(1-indenyl) zirconium dichloride;
1-(2-hydroxyethoxy)-ethylidene-1-(cyclopentadienyl)-2-(1-(2-methyl-indenyl)) zirconium dichloride;
1-(2-hydroxyethoxy)-ethylidene-1-(cyclopentadienyl)-2-(9-fluorenyl) zirconium dichloride;
1-(2-hydroxyethoxy)-ethylidene-1-(cyclopentadienyl)-2-(9-(2-methyl-fluorenyl)) zirconium dichloride;
1-(2-hydroxyethyl)-(dimethyl)silyl ethylidenebis(cyclopentadienyl) zirconium dichloride;
1-(2-hydroxyethyl)-(dimethyl)silyl ethylidene-1-(cyclopentadienyl)-2-(1-indenyl) zirconium dichloride;
1-(2-hydroxyethyl)-(dimethyl)silyl ethylidene-1-(cyclopentadienyl)-2-(1-(2-methyl-indenyl)) zirconium dichloride
1-(2-hydroxyethyl)-(dimethyl)silyl ethylidene-1-(cyclopentadienyl)-2-(9-fluorenyl) zirconium dichloride;
1-(2-hydroxyethyl)-(dimethyl)silyl ethylidene-1-(cyclopentadienyl)-2-(9-(2-methylfluorenyl)) zirconium dichloride;
(2-hydroxyethyl)(methyl)silandiyl-(tertbutylamido)(cylopentadienyl) titanium dichloride;
(2-hydroxyethyl)(methyl)silandiyl-(tertbutylamido)(tetramethylcylopentadienyl) titanium dichloride;
(2-hydroxyethyl)(methyl)silandiyl-(tertbutylamido)(1-indenyl) titanium dichloride;
(2-hydroxyethyl)(methyl)silandiyl-(tertbutylamido)(1-(2-methyl-indenyl)) titanium dichloride;
(2-hydroxyethyl)(methyl)silandiyl-(tertbutylamido)(9-fluorenyl) titanium dichloride;
(2-hydroxyethyl)(methyl)silandiyl-(tertbutylamido)(9-(2-methyl-fluorenyl)) titanium dichloride;
(2-hydroxyethyl)(methyl)silandiyl-(tertbutylamido)(1 -(2-metthylbenzoindenyl) titanium dichloride;
(dimethyl)silandiyl-(tertbutylamido)(3-((2-hydroxyethyl)cylopentadienyl) titanium dichloride;
(dimethyl)silandiyl-(tertbutylamido)(1-(3-(2-hydroxyethyl)indenyl) titanium dichloride;
(dimethyl)silandiyl-(2-(2-hydroxyethyl)amido)(cylopentadienyl) titanium dichloride;
(dimethyl)silandiyl-(2-(2-hydroxyethyl)amido)(tetramethylcylopentadienyl) titanium dichloride;
(dimethyl)silandiyl-(2-(2-hydroxyethyl)amido)(1-indenyl) titanium dichloride;
(dimethyl)silandiyl-(2-(2-hydroxyethyl)amido)(9-fluorenyl) titanium dichloride;
(dimethyl)silandiyl-(2-(2-hydroxyethyl)amido)(1-(2-methylbenzoindenyl) titanium dichloride;
(3-hydroxypropyl)(methyl)silandiyl(tertbutylamido)-(cyclopentadienyl) titanium dichloride;
(3-hydroxypropyl)(methyl)silandiyl-(tertbutylamido)(tetramethylcyclopentadienyl) titanium dichloride;
(3-hydroxypropyl)(methyl)silandiyl-(tertbutylamido)(1-indenyl) titanium dichloride;
(3-hydroxypropyl)(methyl)silandiyl-(tertbutylamido)(1-(2-methyl-indenyl)) titanium dichloride;
(3-hydroxypropyl)(methyl)silandiyl-(tertbutylamido)(9-fluorenyl) titanium dichloride;
(3-hydroxypropyl)(methyl)silandiyl-(tertbutylamido)(9-(2-methyl-fluorenyl)) titanium dichloride;
(3-hydroxypropyl)(methyl)silandiyl(tertbutylamido)-(1-(2-methylbenzoindenyl) titanium dichloride;
(dimethyl)silandiyl-(tertbutylamido)(3-((3-hydroxypropyl)cylopentadienyl) titanium dichloride;
(dimethyl)silandiyl-(tertbutylamido)(1-(3-(3-hydroxypropyl)indenyl) titanium dichloride;
(dimethyl)silandiyl-(3-(3-hydroxypropyl)amido)(cylopentadienyl) titanium dichloride;
(dimethyl)silandiyl-(3-(3-hydroxypropyl)amido)(tetramethylcylopentadienyl) titanium dichloride;
(dimethyl)silandiyl-(3-(3-hydroxypropyl)amido)(1-indenyl) titanium dichloride;
(dimethyl)silandiyl-(3-(3-hydroxypropyl)amido)(9-fluorenyl) titanium dichloride;
(dimethyl)silandiyl-(3-(3-hydroxypropyl)amido)(1 -(2-methylbenzoindenyl) titanium dichloride;
2-hydroxyethyl-methoxy (methyl)silandiyl-(tertbutylamido)(cylopentadienyl) titanium dichloride;
2-hydroxyethyl-methoxy(methyl)silandiyl-(tertbutylamido)(tetramethylcyclopentadienyl) titanium dichloride;
2-hydroxyethyl-methoxy(methyl)silandiyl-(tertbutylamido)(1-indenyl) titanium dichloride;
2-hydroxyethyl-methoxy(methyl)silandiyl-(tertbutylamido)(1-(2-methyl-indenyl)) titanium dichloride;
2-hydroxyethyl-methoxy(methyl)silandiyl-(tertbutylamido)(9-fluorenyl) titanium dichloride;
2-hydroxyethyl-methoxy(methyl)silandiyl-(tertbutylamido)(9-(2-methyl-fluorenyl)) titanium dichloride;
(2-hydroxyethoxy)(methyl)silandiyl-(tertbutylamido)(cylopentadienyl) titanium dichloride;
(2-hydroxyethoxy)(methyl)silandiyl-(tertbutylamido)(tetramethylcyclopentadienyl) titanium dichloride;
(2-hydroxyethoxy)(methyl)silandiyl-(tertbutylamido)(1-indenyl) titanium dichloride;
(2-hydroxyethoxy)(methyl)silandiyl-(tertbutylamido)(1-(2-methyl-indenyl)) titanium dichloride;
(2-hydroxyethoxy)(methyl)silandiyl-(tertbutylamido)(9-fluorenyl) titanium dichloride;
(2-hydroxyethoxy)(methyl)silandiyl-(tertbutylamido)(9-(2-methyl-fluorenyl)) titanium dichloride;
(2-hydroxyethyl)-(dimethyl)silyl-(methyl)silandiyl(tertbutylamido)-(cylopentadienyl) titanium dichloride;
(2-hydroxyethyl)-(dimethyl)silyl-(methyl) silandiyl(tertbutylamido)(tetramethylcyclopentadienyl) titanium dichloride;
(2-hydroxyethyl)-(dimethyl)silyl-(methyl)silandiyl-(tertbutylamido)(1-indenyl) titanium dichloride;
(2-hydroxyethyl)-(dimethyl)silyl-(methyl)silandiyl-(tertbutylamido)(1-(2-methyl-indenyl)) titanium dichloride;
(2-hydroxyethyl)-(dimethyl)silyl-(methyl)silandiyl-(tertbutylamido)(9-fluorenyl) titanium dichloride;
(2-hydroxyethyl)-(dimethyl)silyl-(methyl)silandiyl-(tertbutylamido)(9-(2-methyl-fluorenyl)) titanium dichloride;
(2-hydroxyethyl)-(methyl)methylene(tertbutylamido)(cylopentadienyl) titanium dichloride;
(2-hydroxyethyl)-(methyl)methylene(tertbutylamido)(tetramethylcyclopentadienyl) titanium dichloride;
(2-hydroxyethyl)-(methyl)methylene(tertbutylamido)(1-indenyl) titanium dichloride;
(2-hydroxyethyl)-(methyl)methylene(tertbutylamido)(1-(2-methyl-indenyl)) titanium dichloride;
(2-hydroxyethyl)-(methyl)methylene(tertbutylamido)(9-fluorenyl) titanium dichloride;
(2-hydroxyethyl)-(methyl)methylene(tertbutylamido)(9-(2-methyl-fluorenyl)) titanium dichloride;
(3-hydroxypropyl)-(methyl)methylene(tertbutylamido)(cylopentadienyl) titanium dichloride;
(3-hydroxypropyl)-(methyl)methylene(tertbutylamido)(tetramethylcyclopentadienyl) titanium dichloride;

(3-hydroxypropyl)-(methyl)methylene(tertbutylamido)(indenyl) titanium dichloride;
(3-hydroxypropyl)-(methyl)methylene(tertbutylamido)(2-methyl-indenyl) titanium dichloride;
(3-hydroxypropyl)-(methyl)methylene(tertbutylamido)(9-fluorenyl) titanium dichloride;
(3-hydroxypropyl)-(methyl)methylene(tertbutylamido)(2-methyl-fluorenyl) titanium dichloride;
2-hydroxyethyl-methoxy(methyl)methylene(tertbutylamido)(cylopentadienyl) titanium dichloride;
2-hydroxyethylmethoxy(methyl)methylene(tertbutylamido)(tetramethylcyclopentadienyl) titanium dichloride;
2-hydroxyethyl-methoxy(methyl)methylen(tertbutylamido)(1-indenyl) titanium dichloride;
2-hydroxyethyl-methoxy(methyl)methylen(-tertbutylamido)(1-(2-methyl-indenyl)) titanium dichloride;
2-hydroxyethyl-methoxy(methyl)methylen(-tertbutylamido)(9-fluorenyl) titanium dichloride;
2-hydroxyethyl-methoxy(methyl)methylen(-tertbutylamido)(9-(2-methyl-fluorenyl)) titanium dichloride;
(2-hydroxyethoxy)-(methyl)methylene(tertbutylamido)(cylopentadienyl) titanium dichloride;
(2-hydroxyethoxy)-(methyl)methylene(tertbutylamido)(tetramethylcyclopentadienyl) titanium dichloride;
(2-hydroxyethoxy)-(methyl)methylen(tertbutylamido)(1-indenyl) titanium dichloride;
(2-hydroxyethoxy)-(methyl)methylen(tertbutylamido)(1-(2-methyl-indenyl)) titanium dichloride;
(2-hydroxyethoxy)-(methyl)methylen(tertbutylamido)(9-fluorenyl) titanium dichloride;
(2-hydroxyethoxy)-(methyl)methylen(tertbutylamido)(9-(2-methyl-fluorenyl)) titanium dichloride;
(2-hydroxyethyl)-(dimethyl)silyl-(methyl)methylene(tertbutylamido)(cylopentadienyl) titanium dichloride;
(2-hydroxyethyl)-(dimethyl)silyl-(methyl)methylene(tertbutylamido) (tetramethylcyclopentadienyl) titanium dichloride;
(2-hydroxyethyl)-(dimethyl)silyl-(methyl)methylene(tertbutylamido)(1-indenyl) titanium dichloride;
(2-hydroxyethyl)-(dimethyl)silyl-(methyl)methylene(tertbutylamido)(1-(2-methyl-indenyl)) titanium dichloride;
(2-hydroxyethyl)-(dimethyl)silyl-(methyl)methylene(tertbutylamido)(9-fluorenyl) titanium dichloride;
(2-hydroxyethyl)-(dimethyl)silyl-(methyl)methylene(tertbutylamido)(9-(2-methyl-fluorenyl)) titanium dichloride;
(2-hydroxyethyl)(methyl) silandiyl-oxo(cylopentadienyl) titanium dichloride;
(2-hydroxyethyl)(methyl) silandiyl-oxo-(tetramethylcyclopentadienyl) titanium dichloride;
(2-hydroxyethyl)(methyl) silandiyl-oxo(1-indenyl) titanium dichloride;
(2-hydroxyethyl)(methyl) silandiyl-oxo(1-(2-methyl-indenyl)) titanium dichloride;
(2-hydroxyethyl)(methyl) silandiyl-oxo(9-fluorenyl) titanium dichloride;
(2-hydroxyethyl)(methyl) silandiyl-oxo(9-(2-methyl-fluorenyl)) titanium dichloride;
(3-hydroxypropyl)(methyl) silandiyl-oxo(cylopentadienyl) titanium dichloride;
(3-hydroxypropyl)(methyl) silandiyl-oxo(tetramethylcyclopentadienyl) titanium dichloride;
(3-hydroxypropyl)(methyl) silandiyl-oxo(1-indenyl) titanium dichloride;
(3-hydroxypropyl)(methyl) silandiyl-oxo(1-(2-methyl-indenyl)) titanium dichloride;
(3-hydroxypropyl)(methyl) silandiyl-oxo(9-fluorenyl) titanium dichloride;
(3-hydroxypropyl)(methyl) silandiyl-oxo(9-(2-methyl-fluorenyl)) titanium dichloride;
2-hydroxyethyl-methoxy(methyl) silandiyl- oxo (cylopentadienyl) titanium dichloride;
2-hydroxyethyl-methoxy(methyl) silandiyl-oxo (tetramethylcyclopentadienyl) titanium dichloride;
2-hydroxyethyl-methoxy(methyl) silandiyl-oxo(1-indenyl) titanium dichloride;
2-hydroxyethyl-methoxy(methyl) silandiyl-oxo(1-(2-methyl-indenyl)) titanium dichloride;
2-hydroxyethyl-methoxy(methyl) silandiyl-oxo(9-fluorenyl) titanium dichloride;
2-hydroxyethyl-methoxy(methyl) silandiyl-oxo(9-(2-methyl-fluorenyl)) titanium dichloride;
(2-hydroxyethoxy)(methyl) silandiyl-oxo(cylopentadienyl) titanium dichloride;
(2-hydroxyethoxy)(methyl) silandiyl-oxo (tetramethylcyclopentadienyl) titanium dichloride;
(2-hydroxyethoxy)(methyl) silandiyl-oxo(1-indenyl) titanium dichloride;
(2-hydroxyethoxy)(methyl) silandiyl-oxo(1-(2-methyl-indenyl)) titanium dichloride;
(2-hydroxyethoxy)(methyl) silandiyl-oxo(9-fluorenyl) titanium dichloride;
(2-hydroxyethoxy)(methyl) silandiyl-oxo(9-(2-methyl-fluorenyl)) titanium dichloride;
(2-hydroxyethyl)-(dimethyl)silyl-(methyl) silandiyl-oxo (cylopentadienyl) titanium dichloride;
(2-hydroxyethyl)-(dimethyl)silyl-(methyl) silandiyl-oxo (tetramethylcyclopentadienyl) titanium dichloride;
(2-hydroxyethyl)-(dimethyl)silyl-(methyl) silandiyl-oxo(1-indenyl) titanium dichloride;
(2-hydroxyethyl)-(dimethyl)silyl-(methyl) silandiyl-oxo(1-(2-methyl-indenyl)) titanium dichloride;
(2-hydroxyethyl)-(dimethyl)silyl-(methyl) silandiyl-oxo (fluorenyl) titanium dichloride;
(2-hydroxyethyl)-(dimethyl)silyl-(methyl) silandiyl-oxo(9-methylfluorenyl) titanium dichloride
(2-hydroxyethyl)(methyl)silandiyl-(tertbutylamido)(cylopentadienyl) zirconium dichloride;
(2-hydroxyethyl)(methyl)silandiyl-(tertbutylamido)(tetramethylcylopentadienyl) zirconium dichloride;
(2-hydroxyethyl)(methyl)silandiyl-(tertbutylamido)(1-indenyl) zirconium dichloride;
(2-hydroxyethyl)(methyl)silandiyl-(tertbutylamido)(1-(2-methyl-indenyl)) zirconium dichloride;
(2-hydroxyethyl)(methyl)silandiyl-(tertbutylamido)(9-fluorenyl) zirconium dichloride;
(2-hydroxyethyl)(methyl)silandiyl-(tertbutylamido)(9-(2-methyl-fluorenyl)) zirconium dichloride;
(2-hydroxyethyl)(methyl)silandiyl-(tertbutylamido)(1-(2-metthylbenzoindenyl) zirconium dichloride;
(dimethyl)silandiyl-(tertbutylamido)(3-((2-hydroxyethyl)cyclopentadienyl) zirconium dichloride;
(dimethyl)silandiyl-(tertbutylamido)(1-(3-(2-hydroxyethyl)indenyl) zirconium dichloride;
(dimethyl)silandiyl-(2-(2-hydroxyethyl)amido)(cylopentadienyl) zirconium dichloride;
(dimethyl)silandiyl-(2-(2-hydroxyethyl)amido)(tetramethylcylopentadienyl) zirconium dichloride;
(dimethyl)silandiyl-(2-(2-hydroxyethyl)amido)(1-indenyl) zirconium dichloride;
(dimethyl)silandiyl-(2-(2-hydroxyethyl)amido)(9-fluorenyl) zirconium dichloride;

(dimethyl)silandiyl-(2-(2-hydroxyethyl)amido)(1-(2-methylbenzoindenyl) zirconium dichloride;
(3-hydroxypropyl)(methyl)silandiyl(tertbutylamido)-(cylopentadienyl) zirconium dichloride;
(3-hydroxypropyl)(methyl)silandiyl-(tertbutylamido) (tetramethylcyclopentadienyl) zirconium dichloride;
(3-hydroxypropyl)(methyl)silandiyl-(tertbutylamido)(1-indenyl) zirconium dichloride;
(3-hydroxypropyl)(methyl)silandiyl-(tertbutylamido)(1-(2-methyl-indenyl)) zirconium dichloride;
(3-hydroxypropyl)(methyl)silandiyl-(tertbutylamido)(9-fluorenyl) zirconium dichloride;
(3-hydroxypropyl)(methyl)silandiyl-(tertbutylamido)(9-(2-methyl-fluorenyl)) zirconium dichloride;
(3-hydroxypropyl)(methyl)silandiyl(tertbutylamido)-(1-(2-methylbenzoindenyl) zirconium dichloride;
(dimethyl)silandiyl-(tertbutylamido)(3-((3-hydroxypropyl) cylopentadienyl) zirconium dichloride;
(dimethyl)silandiyl-(tertbutylamido)(1-(3-(3-hydroxypropyl)indenyl) zirconium dichloride;
(dimethyl)silandiyl-(3-(3-hydroxypropyl)amido) (cylopentadienyl) zirconium dichloride;
(dimethyl)silandiyl-(3-(3-hydroxypropyl)amido) (tetramethylcyclopentadienyl) zirconium dichloride;
(dimethyl)silandiyl-(3-(3-hydroxypropyl)amido)(1-indenyl) zirconium dichloride;
(dimethyl)silandiyl-(3-(3-hydroxypropyl)amido)(9-fluorenyl) zirconium dichloride;
(dimethyl)silandiyl-(3-(3-hydroxypropyl)amido)(1-(2-methylbenzoindenyl) zirconium dichloride;
2-hydroxyethyl-methoxy (methyl)silandiyl-(tertbutylamido) (cylopentadienyl) zirconium dichloride;
2-hydroxyethyl-methoxy(methyl)silandiyl-(tertbutylamido) (tetramethylcyclopentadienyl) zirconium dichloride;
2-hydroxyethyl-methoxy(methyl)silandiyl-(tertbutylamido) (1-indenyl) zirconium dichloride;
2-hydroxyethyl-methoxy(methyl)silandiyl-(tertbutylamido) (1-(2-methyl-indenyl)) zirconium dichloride;
2-hydroxyethyl-methoxy(methyl)silandiyl-(tertbutylamido) (9-fluorenyl) zirconium dichloride;
2-hydroxyethyl-methoxy(methyl)silandiyl-(tertbutylamido) (9-(2-methyl-fluorenyl)) zirconium dichloride;
(2-hydroxyethoxy)(methyl)silandiyl-(tertbutylamido) (cylopentadienyl) zirconium dichloride;
(2-hydroxyethoxy)(methyl)silandiyl-(tertbutylamido) (tetramethylcyclopentadienyl) zirconium dichloride;
(2-hydroxyethoxy)(methyl)silandiyl-(tertbutylamido)(1-indenyl) zirconium dichloride;
(2-hydroxyethoxy)(methyl)silandiyl-(tertbutylamido)(1-(2-methyl-indenyl)) zirconium dichloride;
(2-hydroxyethoxy)(methyl)silandiyl-(tertbutylamido)(9-fluorenyl) zirconium dichloride;
(2-hydroxyethoxy)(methyl)silandiyl-(tertbutylamido)(9-(2-methyl-fluorenyl)) zirconium dichloride;
(2-hydroxyethyl)-(dimethyl)silyl-(methyl)silandiyl (tertbutylamido)-(cylopentadienyl) zirconium dichloride;
(2-hydroxyethyl)-(dimethyl)silyl-(methyl) silandiyl (tertbutylamido)(tetramethylcyclopentadienyl) zirconium dichloride;
(2-hydroxyethyl)-(dimethyl)silyl-(methyl)silandiyl-(tertbutylamido)(1-indenyl) zirconium dichloride;
(2-hydroxyethyl)-(dimethyl)silyl-(methyl)silandiyl-(tertbutylamido)(-(2-methyl-indenyl)) zirconium dichloride;
(2-hydroxyethyl)-(dimethyl)silyl-(methyl)silandiyl-(tertbutylamido)(9-fluorenyl) zirconium dichloride;
(2-hydroxyethyl)-(dimethyl)silyl-(methyl)silandiyl-(tertbutylamido)(9-(2-methyl-fluorenyl)) zirconium dichloride;

(2-hydroxyethyl)-(methyl)methylene(tertbutylamido) (cylopentadienyl) zirconium dichloride;
(2-hydroxyethyl)-(methyl)methylene(tertbutylamido) (tetramethylcyclopentadienyl) zirconium dichloride;
(2-hydroxyethyl)-(methyl)methylene(tertbutylamido)(1-indenyl) zirconium dichloride;
(2-hydroxyethyl)-(methyl)methylene(tertbutylamido)(1-(2-methyl-indenyl)) zirconium dichloride;
(2-hydroxyethyl)-(methyl)methylene(tertbutylamido)(9-fluorenyl) zirconium dichloride;
(2-hydroxyethyl)-(methyl)methylene(tertbutylamido)(9-(2-methyl-fluorenyl)) zirconium dichloride;
(3-hydroxypropyl)-(methyl)methylene(tertbutylamido) (cylopentadienyl) zirconium dichloride;
(3-hydroxypropyl)-(methyl)methylene(tertbutylamido) (tetramethylcyclopentadienyl) zirconium dichloride;
(3-hydroxypropyl)-(methyl)methylene(tertbutylamido) (indenyl) zirconium dichloride;
(3-hydroxypropyl)-(methyl)methylene(tertbutylamido)(2-methyl-indenyl) zirconium dichloride;
(3-hydroxypropyl)-(methyl)methylene(tertbutylamido)(9-fluorenyl) zirconium dichloride;
(3-hydroxypropyl)-(methyl)methylene(tertbutylamido)(2-methylfluorenyl) zirconium dichloride;
2-hydroxyethyl-(methyl)methylene(tertbutylamido) (cylopentadienyl) zirconium dichloride;
2-hydroxyethyl-methoxy(methyl)methylene (tertbutylamido)(tetramethylcyclopentadienyl) zirconium dichloride;
2-hydroxyethyl-methoxy(methyl)methylen(tertbutylamido) (1-indenyl) zirconium dichloride;
2-hydroxyethyl-methoxy(methyl)methylen(-tertbutylamido)(1-(2-methyl-indenyl)) zirconium dichloride;
2-hydroxyethyl-methoxy(methyl)methylen(-tertbutylamido)(9-fluorenyl) zirconium dichloride;
2-hydroxyethyl-methoxy(methyl)methylen(-tertbutylamido)(9-(2-methyl-fluorenyl)) zirconium dichloride;
(2-hydroxyethoxy)-(methyl)methylene(tertbutylamido) (cylopentadienyl) zirconium dichloride;
(2-hydroxyethoxy)-(methyl)methylene(tertbutylamido) (tetramethylcyclopentadienyl) zirconium dichloride;
(2-hydroxyethoxy)-(methyl)methylen(tertbutylamido)(1-indenyl) zirconium dichloride;
(2-hydroxyethoxy)-(methyl)methylen(tertbutylamido)(1-(2-methyl-indenyl)) zirconium dichloride;
(2-hydroxyethoxy)-(methyl)methylen(tertbutylamido)(9-fluorenyl) zirconium dichloride;
(2-hydroxyethoxy)-(methyl)methylen(tertbutylamido)(9-(2-methyl-fluorenyl)) zirconium dichloride;
(2-hydroxyethyl)-(dimethyl)silyl-(methyl)methylene (tertbutylamido)(cylopentadienyl) zirconium dichloride;
(2-hydroxyethyl)-(dimethyl)silyl(methyl)methylene (tertbutylamido) (tetramethylcyclopentadienyl) zirconium dichloride;
(2-hydroxyethyl)-(dimethyl)silyl-(methyl)methylene (tertbutylamido)(1-indenyl) zirconium dichloride;
(2-hydroxyethyl)-(dimethyl)silyl-(methyl)methylene (tertbutylamido)(1-(2-methyl-indenyl)) zirconium dichloride;
(2-hydroxyethyl)-(dimethyl)silyl-(methyl)methylene (tertbutylamido)(9-fluorenyl) zirconium dichloride;
(2-hydroxyethyl)-(dimethyl)silyl-(methyl)methylene (tertbutylamido) (9-(2-methyl-fluorenyl)) zirconium dichloride;
(2-hydroxyethyl)(methyl) silandiyl-oxo(cylopentadienyl) zirconium dichloride;

(2-hydroxyethyl)(methyl) silandiyl-oxo-(tetramethylcyclopentadienyl) zirconium dichloride;
(2-hydroxyethyl)(methyl) silandiyl-oxo(1-indenyl) zirconium dichloride;
(2-hydroxyethyl)(methyl) silandiyl-oxo(1-(2-methyl-indenyl)) zirconium dichloride;
(2-hydroxyethyl)(methyl) silandiyl-oxo(9-fluorenyl) zirconium dichloride;
(2-hydroxyethyl)(methyl) silandiyl-oxo(9-(2-methyl-fluorenyl)) zirconium dichloride;
(3-hydroxypropyl)(methyl) silandiyl-oxo(cylopentadienyl) zirconium dichloride;
(3-hydroxypropyl)(methyl) silandiyl-oxo(tetramethylcyclopentadienyl) zirconium dichloride;
(3-hydroxypropyl)(methyl) silandiyl-oxo(1-indenyl) zirconium dichloride;
(3-hydroxypropyl)(methyl) silandiyl-oxo(1-(2-methyl-indenyl)) zirconium dichloride;
(3-hydroxypropyl)(methyl) silandiyl-oxo(9-fluorenyl) zirconium dichloride;
(3-hydroxypropyl)(methyl) silandiyl-oxo(9-(2-methyl-fluorenyl)) zirconium dichloride;
2-hydroxyethyl-methoxy(methyl) silandiyl-oxo (cylopentadienyl) zirconium dichloride;
2-hydroxyethyl-methoxy(methyl) silandiyl-oxo (tetramethylcyclopentadienyl) zirconium dichloride;
2-hydroxyethyl-methoxy(methyl) silandiyl-oxo(1-indenyl) zirconium dichloride;
2-hydroxyethyl-methoxy(methyl) silandiyl-oxo(1-(2-methyl-indenyl)) zirconium dichloride;
2-hydroxyethyl-methoxy(methyl) silandiyl-oxo(9-fluorenyl) zirconium dichloride;
2-hydroxyethyl-methoxy(methyl) silandiyl-oxo(9-(2-methyl-fluorenyl)) zirconium dichloride;
(2-hydroxyethoxy)(methyl) silandiyl-oxo(cylopentadienyl) zirconium dichloride;
(2-hydroxyethoxy)(methyl) silandiyl-oxo(tetramethylcyclopentadienyl) zirconium dichloride;
(2-hydroxyethoxy)(methyl) silandiyl-oxo(1-indenyl) zirconium dichloride;
(2-hydroxyethoxy)(methyl) silandiyl-oxo(1-(2-methyl-indenyl)) zirconium dichloride;
(2-hydroxyethoxy)(methyl) silandiyl-oxo(9-fluorenyl) zirconium dichloride;
(2-hydroxyethoxy)(methyl) silandiyl-oxo(9-(2-methyl-fluorenyl)) zirconium dichloride;
(2-hydroxyethyl)-(dimethyl)silyl-(methyl) silandiyl-oxo (cylopentadienyl) zirconium dichloride;
(2-hydroxyethyl)-(dimethyl)silyl-(methyl) silandiyl-oxo (tetramethylcyclopentadienyl) zirconium dichloride;
(2-hydroxyethyl)-(dimethyl)silyl-(methyl) silandiyl-oxo(1-indenyl) zirconium dichloride;
(2-hydroxyethyl)-(dimethyl)silyl-(methyl) silandiyl-oxo(1-(2-methyl-indenyl)) zirconium dichloride;
(2-hydroxyethyl)-(dimethyl)silyl-(methyl) silandiyl-oxo (fluorenyl) zirconium dichloride;
(2-hydroxyethyl)-(dimethyl)silyl-(methyl) silandiyl-oxo(9-methylfluorenyl) zirconium dichloride
ethylidene(1-(3-(3-hydroxypropyl)-indenyl)) (cyclopentadienyl) zirconium dichloride;
ethylidene(1-(3-(2-hydroxyethyl)-indenyl)) (cyclopentadienyl) zirconium dichloride;
dimethylsilandiyl(1-(3-(2-hydroxyethyl)-indenyl)) (cyclopentadienyl) zirconium dichloride;
dimethylsilandiyl(1-(3-(3-hydroxypropyl)-indenyl)) (cyclopentadienil) zirconium dichloride;
isopropylidene(1-(3-(2-hydroxyethyl)-indenyl)) (cyclopentadienyl) zirconium dichloride;
isopropylidene(1-(3-(3-hydroxypropyl)-indenyl (cyclopentadienyl) zirconium dichloride;

The metallocene complexes belonging to the general formula I can be prepared through reaction of a compound of general formula $[(LR_{k-j}(R^IOJ)_j)]M'$, wherein M' is an alkali metal, preferably Li, Na or K and J is a protective group that masks the OH group, with a transition metal compound of general formula $(LR_k)_zMX_n(E)_q$, wherein E is a linear or cyclic ether, q is a number ranging from 0 to 4 and n is an integer number ranging from 2 to 4 and L, R, k, z and X have been already defined.

The metallocene complexes belonging to the general formulas II and III can be prepared through reaction of a transition metal compound of general formula $MX_n(E)_q$, wherein E is a linear or cyclic ether, q is a number between 0 and 4 and n is 3 or 4, with a compound of general formula

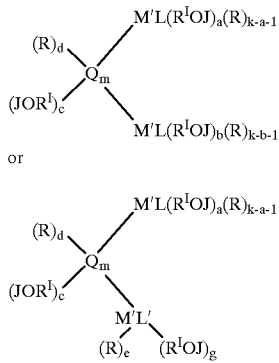

or wherein M' is an alkali metal, preferably Li, Na or K and J is a protective group that masks the OH group, for example it is a $SiR''_3$ or another protective group known in the art. Preferred transition metal compounds of formula $MX_n(E)_q$ are $TiCl_4$, $ZrCl_4$, $HfCl_4$, $TiCl_3$, $TiCl_3.2THF$.

The reaction between the transition metal compound and the alkali metal derivative is preferably realized in a dry nitrogen atmosphere, by using anhydrous solvents such as linear or cyclic ethers (for example diethylether, tetrahydrofurane or dioxane), or aromatic hydrocarbons such as toluene.

The group O—J is then cleaved by a fit reaction. For example, when the protective group J is $SiR''_3$, the de-protection reaction can be an hydrolysis reaction carried out in acidic medium; preferably the hydrolysis reaction is made with silica.

Metallocenes containing a $O—SiR''_3$ group can be prepared according to the method disclosed in EP 97500068.8.

Metallocene compounds of the present invention can be used as catalysts of hydrogenation, epoxidation, double bond isomerization, ketons reduction, aldolic reaction, synthesis of different substituted olefins and as catalyst components for olefin polymerization.

The following examples are described in order to better understand the invention. The materials, the chemical compounds and the conditions used in these examples are illustrative and do not limit the scope of the invention.

EXAMPLES

Example 1

Synthesis of (cyclopentadienyl)((2-hydroxy-ethyl)-cyclopentadienyl) zirconium dichloride a) Preparation of 1-trimethylsiloxy 2-bromo-ethane To 125 g (888 mmol) of 2-bromo-ethanol, 95 ml (1450 mmol) of hexamethyldisilazane are slowly added at 0° C. Ammonia evolution is immediately observed. The reaction is maintained under stirring for 12 hours and a colorless oil is obtained. (168.8 g 856 mmol. Yield:96%) $^1$H-NMR (CDCl3): 3.66 (t,2H), 3.40 (t,2H), 0.14 (s,9H).

b) Preparation of (2-trimethylsiloxy-ethyl)-cyclopentadiene 150 ml of a 2.3 M sodium cyclopentadienylide solution in tetrahydrofurane (346 mmol) is slowly added to a solution of 68.2 g (346 mmol) 2-trimethylsiloxy-1-bromo-ethane in tetrahydrofurane. The immediate formation of a pinkish solid is observed. The reaction is maintained under stirring for 12 hours. Then, an ammonium chloride aqueous solution is added. The organic phase is extracted, dried with magnesium sulphate and the volatile part is distilled under vacuum, obtaining an orange oil. This oil is distilled in order to obtain a colorless oil. (Tb.: 63–65° C., 0.02 bar (15 mmHg.)). (40.3 g, 221 mmol. Yield:64%). $^1$H-NMR (CDCl3): 6.50–6.00 (m,3H), 3.75 (m,2H), 2.95 (m,2H), 2.65 (m,2H), 0.15 (s,9H).

c) Preparation of potassium (2-trimethylsiloxy-ethyl)-cyclopentadienylide

To a suspension of 0.5 g (12.4 mmol) of potassium hydride in tetrahydrofurane, 2.25 g (12.4 mmol) of (2-trimethylsiloxy-ethyl)-cyclopentadiene in tetrahydrofurane is added. The reaction is maintained under stirring for 2 hours and then the volatile compounds are eliminated, leaving an oily solid which is washed with hexane in order to obtain a brown solid. (2.2 g Yield: 81%)

d) Preparation of (cyclopentadienyl) ((2-trimethylsiloxy-ethyl)-cyclopentadienyl) zirconium dichloride To a suspension of 3.52 g (10 mmol) of an adduct of cyclopentadienyl zirconium trichloride with dimethoxyethane in toluene, a suspension of 2.2 g (10 mmol) of potassium (2-trimethylsiloxy-ethyl)-cyclopentadienylide in toluene is added. The addition is realized at −78° C. An orange-brown suspension is immediately formed; it is maintained under stirring for 12 hours; then it is left settling and it is filtered. The obtained orange solution is concentrated up to 5 ml and hexane is added, so that a brown solid is obtained. (1.1 g, 2.7 mmol. Yield: 27%). $^1$H-NMR: 6.00 (t,2H), 5.87 (s,5H), 5.67 (t,2H), 3.66 (t,2H), 2.92 (t,2H), 0.11 (s,9H). Mass spectrum. $M^+$−65: (343): 33%.

e) Preparation of (cyclopentadienyl)((2-hydroxy-ethyl)-cyclopentadienyl) zirconium dichloride 2.16 g (5.69 mmol) of the organocomplex (cyclopentadienyl)(trimethylsiloxyethylcyclopentadienyl) zirconium dichloride was added to a suspension of 2.9 g of Silica XPO 2407 in 75 ml of dry toluene at room temperature; the suspension immediately acquired a greenish-yellow color. The sample was maintained under continuous stirring at room temperature for 48 hours. The yellow solution was separated from the solid by filtration. The solution was brought to dryness and, after washing with three fractions of 15 ml of hexane, a dusty white solid was obtained. (0.57 g Yield: 30%) $^1$H-NMR: (Cl$_3$CD): 1.65 (m,1H), 2.95 (t,2H), 4.05 (m,2H), 6.32 (m,2H), 6.35 (m,2H), 6.5 (s,5H).

Example 2

Synthesis of (cyclopentadienyl)((3-hydroxy-propyl)-cyclopentadienyl) zirconium dichloride a) Preparation of 1-trimethylsiloxy-3-bromo-propane To 12.2 g (76 mmol) of hexamethyldisilazane, 21 g (151 mmol) of 3-bromo-1-propanol is added. Ammonia evolution is immediately observed. The reaction is maintained under stirring for 2 hours and 24.5 g (148 mmol) of the desired compound is finally obtained. Yield: 98%. $^1$H-NMR (CDCl$_3$): 3.74 (t,2H), 3.55 (t,2H), 2.09 (m,2H), 0.14 (s,9H).

b) Preparation of (3-trimethylsiloxy-propyl)-cyclopentadiene

To 50 ml of a 2.3 M solution of sodium cyclopentadienylide (115 mmol), a solution of 24.3 g (115 mmol) of 3-trimethylsiloxy-1-bromo-propane in tetrahydrofurane is added. The quick formation of a pinkish solid is observed. The reaction is maintained under stirring for 12 hours and then it is neutralized with an ammonium chloride solution; the organic phase is extracted and concentrated to dryness in order to give an orange oil. (9.8 g, 50 mmol. Yield: 43%). $^1$H-NMR (CDCl3): 6.47–6.00 (m,3H), 3.62 (m,2H), 2.95 (m,1H), 2.87 (m,1H), 2.43 (m,2H), 1.80 (m,2H), 0.17 (s,9H).

c) Preparation of potassium (3-trimethylsiloxy-propyl)-cyclopentadienylide

To a suspension of 0.4 g (10 mmol) of potassium hydride in tetrahydrofurane, 1.96 g (10 mmol) of a (3-trimethylsiloxy-propyl)-cyclopentadiene in tetrahydrofurane is added. The reaction is maintained under stirring for 2 hours. Subsequently, the resulting suspension is concentrated to dryness, leaving an oily solid that, when it is washed with hexane, gives a cream-colored solid. (1.6 g, 7 mmol. Yield: 70%).

d) Preparation of (cyclopentadienyl)((3-trimethylsiloxy)-propyl-cyclopentadienyl) zirconium dichloride To a suspension of 2.46 g (7 mmol) of cyclopentadienyl zirconium trichloride in toluene, a suspension of 1.6 g (7 mmol) of potassium (3-trimethylsiloxy)-propyl-cyclopentadienylide in toluene is added. A yellow-brown-colored suspension immediately precipitates. The reaction is maintained for 12 hours. Subsequently, the solution is filtered and concentrated and a crystalline white solid is formed (0.8 g, 2 mmol, 28%). $^1$H-NMR (C6D6): 5.87 (t,2H), 5.65 (t,2H), 3.46 (m,2H), 2.74 (m,2H), 1.73 (m,2H), 0.14 (s,9H). 13C-NMR (C6D6): 116.9, 115.0, 114.7, 112.2, 61.8, 33.6, 26.8, -0.393. Mass spectrum: $M^+$−65(356): 30%.

e) Preparation of (cyclopentadienyl)((3-hydroxy-propyl)-cyclopentadienyl) zirconium dichloride 0.5 g (1.18 mmol) of (cyclopentadienyl) (trimethylsiloxypropyl-cyclopentadienyl) zirconium dichloride was added to a suspension of 1.1 g of Silica XPO 2407 in 75 ml of dry toluene at room temperature; the suspension immediately acquired a greenish-yellow color. The sample was maintained under continuous magnetic stirring at room temperature for two days. Then it was filtered, separating the solution from the insoluble product. The resulting colorless solution was brought to dryness. In this way it was possible to isolate a dusty white solid product. (0.16 g Yield: 39%) $^1$H-NMR: (Cl$_3$CD): 1.45 (m,1 H), 1.87 (t,2H), 2.72 (t,2H), 3.80 (t,2H), 6.10 (m,2H), 6.28 (m,2H), 6.28 (m,2H), 6.45 (s,5H). Mass spectrum: $M^+$−36.45 (312):55%.

What is claimed is:

1. A metallocene compound having a formula I, II, or III:

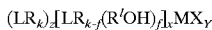

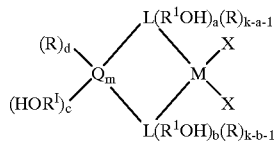

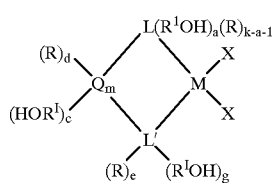

wherein:
  each L is independently cyclopentadienyl, indenyl, tetrahydroindenyl, fluorenyl, octahydrofluorenyl or benzoindenyl;
  each R is independently hydrogen, $C_1$–$C_{20}$ alkyl, $C_3$–$C_{20}$ cycloalkyl, $C_6$–$C_{20}$ aryl, $C_3$–$C_{20}$ alkenyl, $C_7$–$C_{20}$ arylalkyl, $C_7$–$C_{20}$ alkylaryl, $C_8$–$C_{20}$ arylalkenyl, or a group $SiR''_3$; wherein Cl–$C_{20}$ alkyl, $C_3$–$C_{20}$ cycloalkyl, $C_6C_{20}$ aryl, $C_3$–$C_{20}$ alkenyl, $C_7$–$C_{20}$ arylalkyl, $C_7$–$C20$ alkylaryl, and $C_8$–$C_{20}$ arylalkenyl are linear or branched and optionally substituted with 1 to 10 halogen atoms;
  each $R^I$ is independently a group $SiR''_2$ or a divalent aliphatic or aromatic hydrocarbon group containing from 1 to 20 carbon atoms, optionally containing from 1 to 5 heteroatoms of groups 14 to 16 of the Periodic Table of the elements and boron;
  each Q is independently selected from the group consisting of B, C, Si, Ge, and Sn;
  M is a metal of group 3 or 4 of the Periodic Table, Lanthanide or Actinide;
  each X is independently hydrogen, chlorine, bromine, $OR''$, $NR''_2$, $C_1$–$C_{20}$ alkyl or $C_6$–$C_{20}$ aryl;
  each $R''$ is independently linear or branched $C_1$–$C_{20}$ alkyl, linear or branched $C_3$–$C_{20}$ cycloalkyl, linear or branched $C_6$–$C_{20}$ aryl, linear or branched $C_3$–$C_{20}$ alkenyl, linear or branched $C_7$–$C_{20}$ arylalkyl, linear or branched $C_7$–$C_{20}$ arylalkenyl, or linear or branched $C_7$–$C_{20}$ alkylaryl;
  L' is N or O;
  when L is cyclopentadienyl k is equal to 5; when L is indenyl k is equal to 7; when L is fluorenyl or benzoindenyl k is equal to 9; when L is tetrahydroindenyl k is equal to 11; and when L is octahydrofluorenyl, k is equal to 17;
  z is equal to 0, 1 or 2;
  x is equal to 1, 2 or 3;
  y is equal to 1, 2 or 3;
  M has a valence, and x+y+z is equal to the valence of M;
  m is an integer and is 1, 2, 3 or 4;
  is an integer whose value ranges from 0 to k-1;
  b is an integer whose value ranges from 0 to k-1;
  f is an integer whose value ranges from 1 to k;
  g is 0 or 1;
  c is equal to 0 or 1;
  e is equal to 0 or 1;
  a+b+c is at least 1;
  a+g+c is at least 1;
  d is equal to 0, 1 or 2;
  when Q is B then c+d=1;
  when Q is C, Si, Ge or Sn, then c+d=2;
  when L' is N, then g+e=1; and
  when L' is O, then g=0 and e=0.

2. A metallocene compound according to claim 1, wherein $R^I$ is: linear or branched $C_1$–$C_{20}$ alkylene, linear or branched $C_3$–$C_{20}$ cycloalkylene, linear or branched $C_6$–$C_20$ arylene, linear or branched $C_7$–$C_{20}$ alkenyl, linear or branched $C_7$–$C_{20}$ arylalkylene, or linear or branched alkylarylene, or a group $SiR''_2$.

3. A metallocene compound according to claim 1 wherein $R^IOH$ is $CH_2$—$CH_2$—OH, $CH_2$—$CH_2$—$CH_2$—OH, O—$CH_2$—$CH_2$—OH, $SiMe_2$—$CH_2$—$CH_2$—OH or $SiMe_2$—$CH_2$—$CH_2$—OH.

4. A metallocene compound according to claim 1 wherein M is titanium, zirconium or hafnium.

5. A metallocene compound according to claim 1 wherein at least one L is a fluorenyl or an octahydrofluorenyl ring.

6. A process for obtaining a metallocene compound of formula I according to claim 1, the process comprising reacting a compound of general formula $[(LR_{k-f}(R^IOJ)f)_f)]$ M', wherein M' is an alkali metal, and J is a protective group that masks the OH group, with a transition metal compound of general formula $(LR_k)_z MX_n(E)_q$, wherein E is a linear or cyclic ether, q is a number ranging from 0 to 4, and n is an integer ranging from 2 to 4, followed by a cleavage of the group O—J.

7. A process for obtaining a metallocene compound of formula II or III according to claim 1, the Process comprising reacting a transition metal compound of general formula $MX_n(E)_q$, wherein E is a linear or cyclic ether, q is a number between 0 and 4 and n is 3 or 4, with another compound of general formula

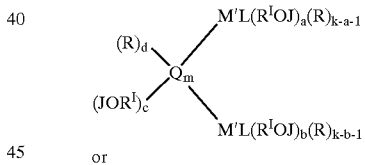

or

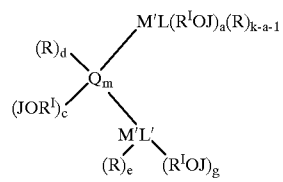

wherein M' is an alkali metal, and J is a protective group that masks the OH group, followed by a cleavage of the group O—J.

8. A process according to claim 6, wherein the compound of formula $MX_n(E)_q$ is selected from the group consisting of $TiCl_4$, $ZrCl_4$, $HfCl_4$, $TiCl_3$, and $TiCl_3 \cdot 2THF$.

9. A process according to claim 6, wherein J is $SiR''_3$ and the group O—$SiR''_3$ is cleaved by controlled hydrolysis reactions.

10. A metallocene compound as claimed in claim 1, wherein $R''$ is methyl, ethyl, or isopropyl.

11. A process as claimed in claim 6, wherein M' is Li, Na or K.

12. A process as claimed in claim 7, wherein M' is Li, Na or K.

13. A metallocene compound as claimed in claim 2, wherein M is titanium, zirconium, or hafnium.

14. A metallocene compound as claimed in claim 3, wherein M is titanium, zirconium, or hafnium.

15. A metallocene compound as claimed in claim 2, wherein M is titanium, zirconium, or hafnium; and wherein at least one L is a fluorenyl or an octahydrofluorenyl ring.

16. A metallocene compound as claimed in claim 3, wherein M is titanium, zirconium, or hafnium; and wherein at least one L is a fluorenyl or an octahydrofluorenyl ring.

17. A process according to claim 7, wherein J is $SiR''_3$ and the group $O-SiR''_3$ is cleaved by a controlled hydrolysis reaction.

18. A process according to claim 8, wherein J is $SiR''3$ and the group $O-SiR''_3$ is cleaved by a controlled hydrolysis reaction.

19. A metallocene compound having a formula selected from the group consisting of:

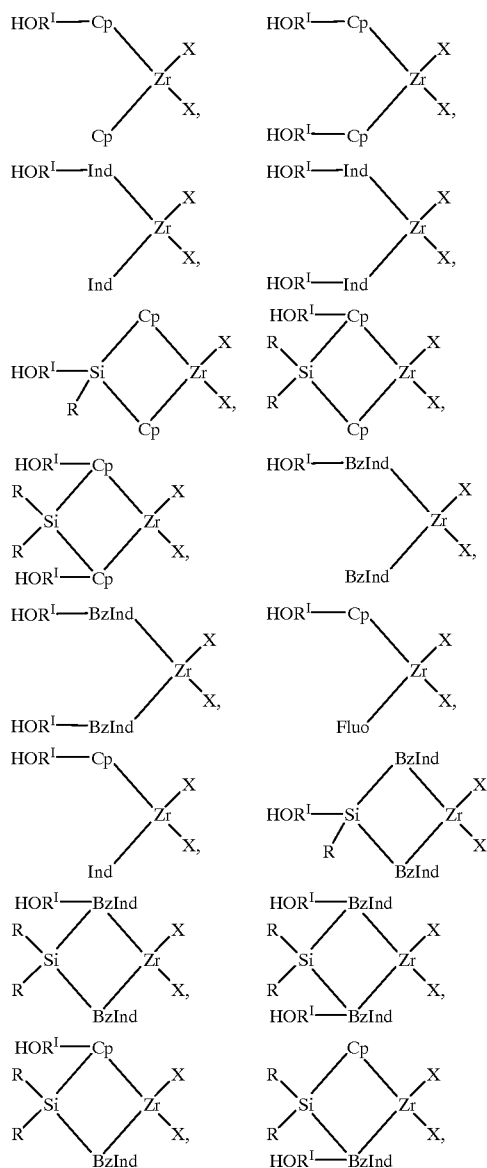

-continued

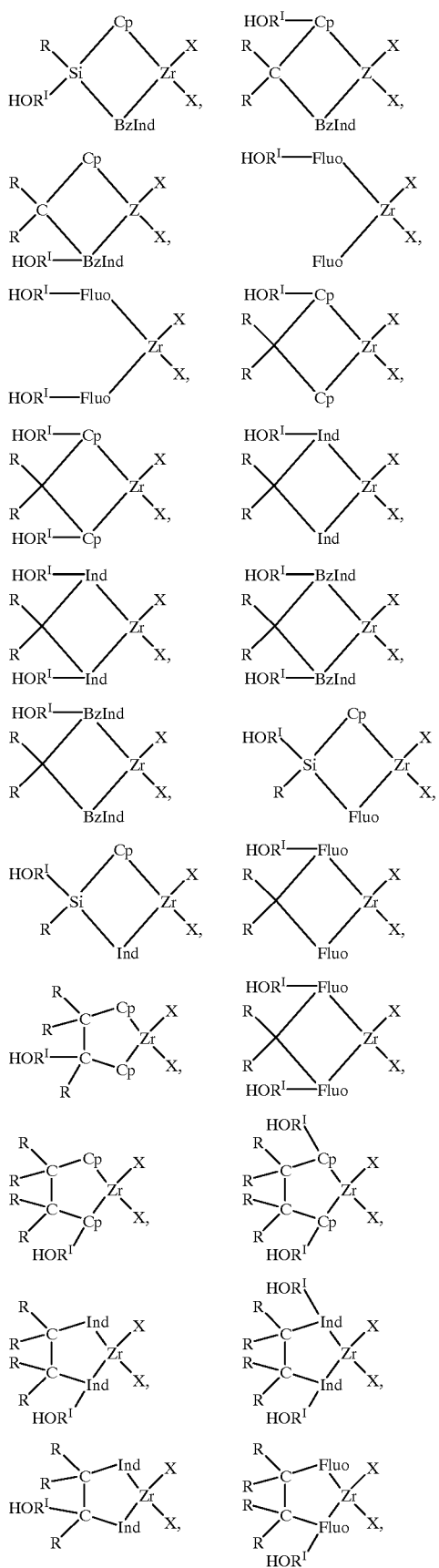

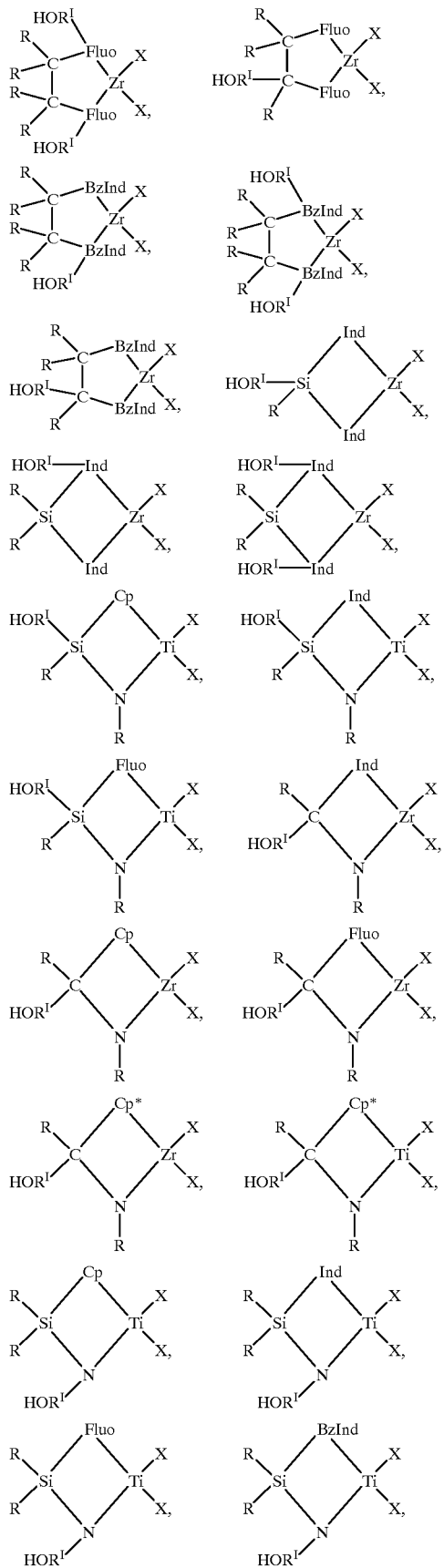
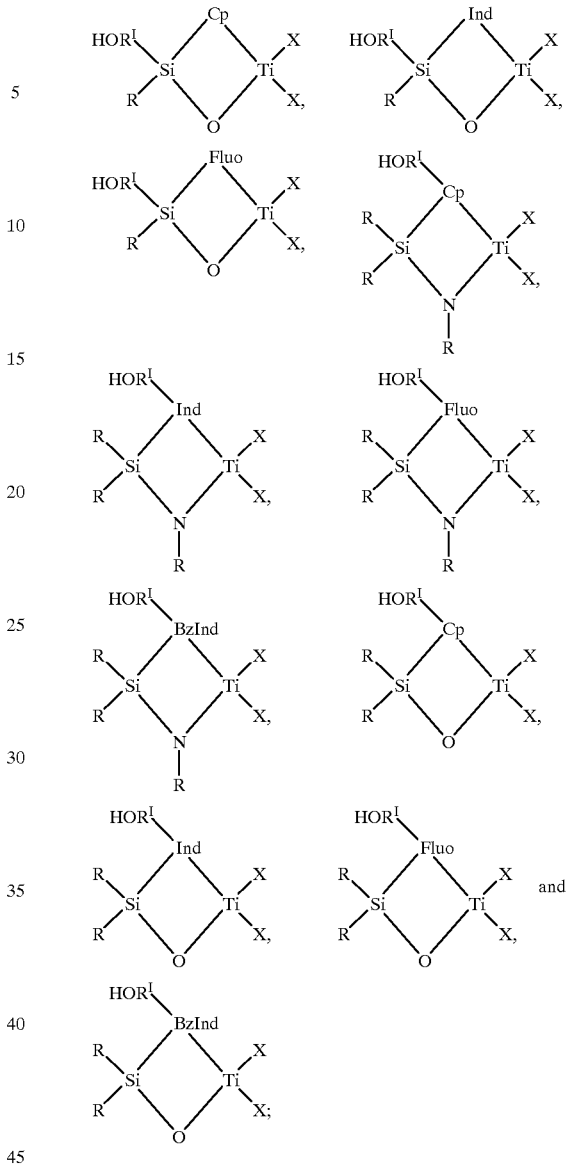

wherein Cp is a cyclopentadienyl ring; wherein Ind is an indenyl ring; wherein BzInd is a benzoindenyl ring; wherein Fluo is a fluorenyl ring; wherein the cyclopentadienyl ring, the indenyl ring, the benzoindenyl ring, and the fluorenyl ring are optionally substituted by $C_1$–$C_{20}$ alkyl, $C_3$–$C_{20}$ cycloalkyl, $C_6$–$C_{20}$ aryl, $C_3$–$C_{20}$ alkenyl, $C_7$–$C_{20}$ arylalkyl, $C_8$–$C_{20}$ arylalkenyl, or $C_7$–$C_{20}$ alkylaryl; and wherein:

each R is independently hydrogen, $C_1$–$C_{20}$ alkyl, $C_3$–$C_{20}$ cycloalkyl, $C_6$–$C_{20}$ aryl, $C_3$–$C_{20}$ alkenyl, $C_7$–$C_{20}$ arylalkyl, $C_7$–$C_{20}$ alkylaryl, $C_8$–$C_{20}$ arylalkenyl, or a group $SiR^{II}_3$; wherein $C_1$–$C_{20}$ alkyl, $C_3$–$C_{20}$ cycloalkyl, $C_6$–$C_{20}$ aryl, $C_3$–$C_{20}$ alkenyl, $C_7$–$C_{20}$ arylalkyl, $C_7$–$C_{20}$ alkylaryl, and $C_8$–$C_{20}$ arylalkenyl are linear or branched and optionally substituted with 1 to 10 halogen atoms;

each $R^I$ is independently a group $SiR^{II}_2$ or a divalent aliphatic or aromatic hydrocarbon group containing from 1 to 20 carbon atoms, optionally containing from 1 to 5 heteroatoms of groups 14 to 16 of the Periodic Table of the elements and boron;

each X is independently hydrogen, chlorine, bromine, $OR^{II}$, $NR^{II}_2$, $C_1$–$C_{20}$ alkyl or $C_6$–$C_{20}$ aryl;

each $R''$ is independently linear or branched $C_1$–$C_{20}$ alkyl, linear or branched $C_3$–$C_{20}$ cycloalkyl, linear or branched $C_6$–$C_{20}$ aryl, linear or branched $C_3$–$C_{20}$ alkenyl, linear or branched $C_7$–$C_{20}$ arylalkyl, linear or branched $C_7$–$C_{20}$ arylalkenyl, or linear or branched $C_7$–$C_{20}$ alkylaryl.

20. A metallocene compound according to claim 19, wherein $R^I$ is:

linear or branched $C_1$–$C_{20}$ alkylene, linear or branched $C_3$–$C_{20}$cycloalkylene, linear or branched $C_6$–$C_{20}$ arylene, linear or branched $C_7$–$C_{20}$ alkenyl, linear or branched $C_7$–$C_{20}$ arylalkylene, or linear or branched alkylarylene, or a group $SiR''_2$.

21. A metallocene compound according to claim 19 wherein $R^I$OH is CH$_2$—CH$_2$—OH, CH$_2$—CH$_2$—CH$_2$—OH, O—CH$_2$—CH$_2$—OH, SiMe$_2$—CH$_2$—CH$_2$—OH or SiMe$_2$—CH$_2$—CH$_2$—CH$_2$—OH.

22. A compound as claimed in claim 19, wherein $R''$ is methyl, ethyl, or isopropyl.

23. A compound as claimed in claim 20, wherein $R''$ is methyl, ethyl, or isopropyl.

24. A compound as claimed in claim 21, wherein $R''$ is methyl, ethyl, or isopropyl.

25. A metallocene compound selected from the group consisting of:

bis(2-hydroxyethyl-cyclopentadienyl) zirconium dichloride;
(2-hydroxyethyl-cyclopentadienyl)(cyclopentadienyl) zirconium dichloride;
(2-hydroxyethyl-cyclopentadienyl)(indenyl) zirconium dichloride;
(2-hydroxyethyl-cyclopentadienyl)(2-methyl-indenyl) zirconium dichloride;
(2-hydroxyethyl-cyclopentadienyl)(fluorenyl) zirconium dichloride;
(2-hydroxyethyl-cyclopentadienyl)(9-methyl-fluorenyl) zirconium dichloride;
(2-hydroxyethyl-cyclopentadienyl)(pentamethylcyclopentadienyl) zirconium dichloride;
bis(3-hydroxyropyl-cyclopentadienyl) zirconium dichloride;
(3-hydroxyropyl-cyclopentadienyl)(cyclopentadienyl) zirconium dichloride;
(3-hydroxyropyl-cyclopentadienyl)(indenyl) zirconium dichloride;
(3-hydroxyropyl-cyclopentadienyl)(2-methyl-indenyl) zirconium dichloride;
(3-hydroxyropyl-cyclopentadienyl)(fluorenyl) zirconium dichloride;
(3-hydroxyropyl-cyclopentadienyl)(9-methyl-fluorenyl) zirconium dichloride;
(3-hydroxyropyl-cyclopentadienyl)(pentamethylcyclopentadienyl) zirconium dichloride:
bis(2-hydroxy-ethoxy-cyclopentadienyl) zirconium dichloride;
(2-hydroxy-ethoxy-cyclopentadienyl)(cyclopentadienyl) zirconium dichloride;
(2-hydroxy-ethoxy-cyclopentadienyl)(1-indenyl) zirconium dichloride;
(2-hydroxy-ethoxy-cyclopentadienyl)(2-methyl-indenyl) zirconium dichloride;
(2-hydroxy-ethoxy-cyclopentadienyl)(fluorenyl) zirconium dichloride;
(2-hydroxy-ethoxy-cyclopentadienyl)(9-methyl-fluorenyl) zirconium dichloride;
(2-hydroxy-ethoxy-cyclopentadienyl)(pentamethylcyclopentadienyl) zirconium dichloride;
bis(2-hydroxy-ethyl-(dimethyl)silyl-cyclopentadienyl) zirconium dichloride;
(2-hydroxy-ethyl-(dimethyl)silyl-cyclopentadienyl)(cyclopentadienyl) zirconium dichloride;
(2-hydroxy-ethyl-(dimethyl)silyl-cyclopentadienyl)(indenyl) zirconium dichloride;
(2-hydroxy-ethyl-(dimethyl)silyl-cyclopentadienyl)(2-methyl-indenyl) zirconium dichloride;
(2-hydroxy-ethyl-(dimethyl)silyl-cyclopentadienyl)(fluorenyl) zirconium dichloride;
(2-hydroxy-ethyl-(dimethyl)silyl-cyclopentadienyl)(9-methyl-fluorenyl) zirconium dichloride;
(2-hydroxy-ethyl-(dimethyl)silyl-cyclopentadienyl)(pentamethylcyclopentadienyl) zirconium dichloride;
bis(2-hydroxy-(dimethyl)silyl-cyclopentadienyl) zirconium dichloride;
(2-hydroxy-(dimethyl)silyl-cyclopentadienyl)(cyclopentadienyl) zirconium dichloride;
dimethylsilandiylbis(2-(2-hydroxyethyl)-cyclopentadienyl) zirconium dichloride;
dimethylsilandiylbis(3-(2-hydroxyethyl)-cyclopentadienyl) zirconium dichloride;
dimethylsilandiyl(3-(2-hydroxyethyl)-cyclopentadienyl)(cyclopentadienyl)zirconium dichloride;
dimethylsilandiyl(2-(2-hydroxyethyl)-cyclopentadienyl)(1-indenyl) zirconium dichloride;
dimethylsilandiyl(3-(2-hydroxyethyl)-cyclopentadienyl)(1-indenyl) zirconium dichloride;
dimethylsilandiyl(2-(2-hydroxyethyl)-cyclopentadienyl)(1-(2-methyl-indenyl)) zirconium dichloride;
dimethylsilandiyl(3-(2-hydroxyethyl)-cyclopentadienyl)(1-(2-methyl-indenyl)) zirconium dichloride;
dimethylsilandiyl(2-(2-hydroxyethyl)-cyclopentadienyl)(9-fluorenyl) zirconium dichloride;
dimethylsilandiyl(3-(2-hydroxyethyl)-cyclopentadienyl)(9-fluorenyl) zirconium dichloride;
dimethylsilandiyl(2-(2-hydroxyethyl)-cyclopentadienyl)(9-(2-methyl-fluorenyl)) zirconium dichloride;
dimethylsilandiyl(3-(2-hydroxyethyl)-cyclopentadienyl)(9-(2-methyl-fluorenyl)) zirconium dichloride;
dimethylsilandiyl(3-(2-hydroxyethyl)-cyclopentadienyl)(1-(2methylbenzoindenyl)) zirconium dichloride;
dimethylsilandiylbis(2-(3-hydroxypropyl)-cyclopentadienyl) zirconium dichloride;
dimethylsilandiylbis(3-3-hydroxyropyl-cyclopentadienyl) zirconium dichloride;
dimethylsilandiyl(3-3-hydroxyropyl-cyclopentadienyl)(cyclopentadienyl) zirconium dichloride;
dimethylsilandiyl(2-(3-hydroxypropyl)-cyclopentadienyl)(l-indenyl) zirconium dichloride;
dimethylsilandiyl(3-3-hydroxyropyl-cyclopentadienyl)(1-indenyl) zirconium dichloride;
dimethylsilandiyl(2-(3-hydroxypropyl)-cyclopentadienyl)(1-(2-methyl-indenyl)) zirconium dichloride;
dimethylsilandiyl(3-3-hydroxyropyl-cyclopentadienyl)(I-(2-methyl-indenyl)) zirconium dichloride;
dimethylsilandiyl(2-(3-hydroxypropyl)-cyclopentadienyl)(9-fluorenyl) zirconium dichloride;
dimethylsilandiyl(3-3-hydroxyropyl-cyclopentadienyl)(9-fluorenyl) zirconium dichloride;
dimethylsilandiyl(2-(3-hydroxypropyl)-cyclopentadienyl)(9-(2-methyl-fluorenyl)) zirconium dichloride;
dimethylsilandiyl(3-3-hydroxyropyl-cyclopentadienyl)(9-(2-methyl-fluorenyl)) zirconium dichloride;
dimethylsilandiyl(3-3-hydroxyropyl-cyclopentadienyl)(1-(2methylbenzoindenyl)) zirconium dichloride;
dimethylsilandiylbis(2-(2-hydroxy)-ethoxy-cyclopentadienyl) zirconium dichloride;
dimethylsilandiylbis(3-(2-hydroxy)-ethoxy-cyclopentadienyl) zirconium dichloride;

dimethylsilandiyl(2-(2-hydroxy)-ethoxy-cyclopentadienyl)(1-indenyl) zirconium dichloride;
dimethylsilandiyl(3-(2-hydroxy)-ethoxy-cyclopentadienyl)(1-indenyl) zirconium dichloride;
dimethylsilandiyl(2-(2-hydroxy)-ethoxy-cyclopentadienyl)(1-(2-methyl-indenyl)) zirconium dichloride;
dimethylsilandiyl(3-(2-hydroxy)-ethoxy-cyclopentadienyl)(1-(2-methyl-indenyl)) zirconium dichloride;
dimethylsilandiyl(2-(2-hydroxy)-ethoxy-cyclopentadienyl)(9-fluorenyl) zirconium dichloride;
dimethylsilandiyl(3-(2-hydroxy)-ethoxy-cyclopentadienyl)(9-fluorenyl) zirconium dichloride;
dimethylsilandiyl(2-(2-hydroxy)-ethoxy-cyclopentadienyl)(9-(2-methyl-fluorenyl)) zirconium dichloride;
dimethylsilandiyl(3-(2-hydroxy)-ethoxy-cyclopentadienyl)(9-(2-methyl-fluorenyl)) zirconium dichloride;
dimethylsilandiylbis(2-(2-hydroxy-ethyl-(dimethyl)silyl)-cyclopentadienyl) zirconium dichloride;
dimethylsilandiylbis(3-(2-hydroxy-ethyl-(dimethyl)silyl)-cyclopentadienyl) zirconium dichloride;
dimethylsilandiyl(2-(2-hydroxy-ethyl-(dimethyl)silyl)-cyclopentadienyl)(1-indenyl) zirconium dichloride;
dimethylsilandiyl(3-(2-hydroxy-ethyl-(dimethyl)silyl)-cyclopentadienyl)(1-indenyl) zirconium dichloride;
dimethylsilandiyl(2-(2-hydroxy-ethyl-(dimethyl)silyl)-cyclopentadienyl)(1-(2-methyl-indenyl)) zirconium dichloride;
dimethylsilandiyl(3-(2-hydroxy-ethyl-(dimethyl)silyl)-cyclopentadienyl)(1-(2-methyl-indenyl)) zirconium dichloride;
dimethylsilandiyl(2-(2-hydroxy-ethyl-(dimethyl)silyl)-cyclopentadienyl)(9-fluorenyl) zirconium dichloride;
dimethylsilandiyl(3-(2-hydroxy-ethyl-(dimethyl)silyl)-cyclopentadienyl)(9-fluorenyl) zirconium dichloride;
dimethylsilandiyl(2-(2-hydroxy-ethyl-(dimethyl)silyl)-cyclopentadienyl)(9-(2-methyl-fluorenyl)) zirconium dichloride
dimethylsilandiyl(3-(2-hydroxy-ethyl-(dimethyl)silyl)-cyclopentadienyl)(9-(2-methyl-fluorenyl)) zirconium dichloride
dimethylsilandiyl(3-(2-hydroxy-(dimethyl)silyl)-cyclopentadienyl)(1-indenyl) zirconium dichloride;
dimethylsilandiyl(3-(2-hydroxy-(dimethyl)silyl)-cyclopentadienyl)(1-(2-methylbenzoindenyl)) zirconium dichloride;
dimethylsilandiylbis(3-(2-hydroxy-(dimethyl)silyl-1-indenyl) zirconium dichloride;
dimethylsilandiyl(3-(2-hydroxy-(dimethyl)silyl-1 -indenyl)(1 -indenyl)zirconium dichloride;
isopropylidenebis(2-(2-hydroxyethyl)-cyclopentadienyl) zirconium dichloride;
isopropylidenebis(3-(2-hydroxyethyl)-cyclopentadienyl) zirconium dichloride;
isopropylidene(2-(2-hydroxyethyl)-cyclopentadienyl)(1-indenyl) zirconium dichloride;
isopropylidene(3-(2-hydroxyethyl)-cyclopentadienyl)(1-indenyl) zirconium dichloride;
isopropylidene(2-(2-hydroxyethyl)-cyclopentadienyl)(1-(2-methyl-indenyl)) zirconium dichloride;
isopropylidene(3-(2-hydroxyethyl)-cyclopentadienyl)(1-(2-methyl-indenyl)) zirconium dichloride;
isopropylidene(2-(2-hydroxyethyl)-cyclopentadienyl)(9-fluorenyl) zirconium dichloride;
isopropylidene(3-(2-hydroxyethyl)-cyclopentadienyl)(9-fluorenyl) zirconium dichloride;
isopropylidene(2-(2-hydroxyethyl)-cyclopentadienyl)(9-(2-methyl-fluorenyl)) zirconium dichloride;
isopropylidene(3-(2-hydroxyethyl)-cyclopentadienyl)(9-(2-methyl-fluorenyl)) zirconium dichloride;
isopropylidene(3-(2-hydroxyethyl)-cyclopentadienyl)(1-(2methylbenzoindenyl)) zirconium dichloride;
isopropylidenebis(2-(3-hydroxypropyl)-cyclopentadienyl) zirconium dichloride;
isopropylidenebis(3-(3-hydroxyropyl-cyclopentadienyl) zirconium dichloride;
isopropylidene(2-(3-hydroxypropyl)-cyclopentadienyl)(1-indenyl) zirconium dichloride;
isopropylidene(3-(3-hydroxyropyl-cyclopentadienyl)(1-indenyl) zirconium dichloride;
isopropylidene(2-(3-hydroxypropyl)-cyclopentadienyl)(1-(2-methyl-indenyl)) zirconium dichloride;
isopropylidene(3-3-hydroxyropyl-cyclopentadienyl)(1-(2-methyl-indenyl)) zirconium dichloride;
isopropylidene(2-(3-hydroxypropyl)-cyclopentadienyl)(9-fluorenyl) zirconium dichloride;
isopropylidene(3-3-hydroxyropyl-cyclopentadienyl)(9-fluorenyl) zirconium dichloride;
isopropylidene(2-(3-hydroxypropyl)-cyclopentadienyl)(9-(2-methyl-fluorenyl)) zirconium dichloride;
isopropylidene(3-3-hydroxyropyl-cyclopentadienyl)(9-(2-methyl-fluorenyl)) zirconium dichloride;
isopropylidene(3-3-hydroxyropyl-cyclopentadienyl)(1-(2methylbenzoindenyl)) zirconium dichloride;
isopropylidenebis(2-(2-hydroxy-ethoxy)-cyclopentadienyl) zirconium dichloride;
isopropylidenebis(3-(2-hydroxy-ethoxy)-cyclopentadienyl) zirconium dichloride;
isopropylidene(2-(2-hydroxy-ethoxy)-cyclopentadienyl)(1-indenyl) zirconium dichloride;
isopropylidene(3-(2-hydroxy-ethoxy)-cyclopentadienyl)(1-indenyl ) zirconium dichloride;
isopropylidene(2-(2-hydroxy-ethoxy)-cyclopentadienyl)(1-(2-methyl-indenyl)) zirconium dichloride;
isopropylidene(3-(2-hydroxy-ethoxy)-cyclopentadienyl)(1-(2-methyl-indenyl)) zirconium dichloride;
isopropylidene(2-(2-hydroxy-ethoxy)-cyclopentadienyl)(9-fluorenyl) zirconium dichloride;
isopropylidene(3-(2-hydroxy-ethoxy)-cyclopentadienyl)(9-fluorenyl) zirconium dichloride;
isopropylidene(2-(2-hydroxy-ethoxy)-cyclopentadienyl)(9-(2-methyl-fluorenyl)) zirconium dichloride;
isopropylidene(3-(2-hydroxy-ethoxy)-cyclopentadienyl)(9-(2-methyl-fluorenyl)) zirconium dichloride ;
isopropylidenebis(2-(2-hydroxy-ethyl-(dimethyl)silyl)-cyclopentadienyl) zirconium dichloride;
isopropylidenebis(3-(2-hydroxy-ethyl-(dimethyl)silyl)-cyclopentadienyl) zirconium dichloride;
isopropylidene(2-(2-hydroxy-ethyl-(dimethyl)silyl)-cyclopentadienyl)(1-indenyl) zirconium dichloride;
isopropylidene(3-(2-hydroxy-ethyl-(dimethyl)silyl)-cyclopentadienyl)(1-indenyl) zirconium dichloride;
isopropylidene(2-(2-hydroxy-ethyl-(dimethyl)silyl)-cyclopentadienyl)(1-(2-methyl-indenyl)) zirconium dichloride;
isopropylidene(3-(2-hydroxy-ethyl-(dimethyl)silyl)-cyclopentadienyl)(1-(2-methyl-indenyl)) zirconium dichloride;
isopropylidene(2-(2-hydroxy-ethyl-(dimethyl)silyl)-cyclopentadienyl)(9-fluorenyl) zirconium dichloride;
isopropylidene(3-(2-hydroxy-ethyl-(dimethyl)silyl)-cyclopentadienyl)(9-fluorenyl) zirconium dichloride;
isopropylidene(2-(2-hydroxy-ethyl-(dimethyl)silyl)-cyclopentadienyl)(9-(2-methyl-fluorenyl)) zirconium dichloride;

isopropylidene(3-(2-hydroxy-ethyl-(dimethyl)silyl)-cyclopentadienyl)(9-(2-methyl-fluorenyl)) zirconium dichloride
isopropylidene(2-(2-hydroxy-(dimethyl)silyl)-cyclopentadienyl)(1-indenyl) zirconium dichloride;
isopropylidene(2-(2-hydroxy-(dimethyl)silyl)-cyclopentadienyl)(1-(2-methylbenzoindenyl)) zirconium dichloride;
ethylidenebis(2-(2-hydroxyethyl)-cyclopentadienyl) zirconium dichloride;
ethylidenebis(3-(2-hydroxyethyl)-cyclopentadienyl) zirconium dichloride;
ethylidene(3-(2-hydroxyethyl)-cyclopentadienyl)(cyclopentadienyl) zirconium dichloride;
ethylidene(2-(2-hydroxyethyl)-cyclopentadienyl)(1-indenyl) zirconium dichloride;
ethylidene(3-(2-hydroxyethyl)-cyclopentadienyl)(1-indenyl) zirconium dichloride;
ethylidene(2-(2-hydroxyethyl)-cyclopentadienyl)(1-(2-methyl-indenyl)) zirconium dichloride;
ethylidene(3-(2-hydroxyethyl)-cyclopentadienyl)(1-(2-methyl-indenyl)) zirconium dichloride;
ethylidene(2-(2-hydroxyethyl)-cyclopentadienyl)(9-fluorenyl) zirconium dichloride;
ethylidene(3-(2-hydroxyethyl)-cyclopentadienyl)(9-fluorenyl) zirconium dichloride;
ethylidene(2-(2-hydroxyethyl)-cyclopentadienyl)(9-(2-methyl-fluorenyl)) zirconium dichloride;
ethylidene(3-(2-hydroxyethyl)-cyclopentadienyl)(9-(2-methyl-fluorenyl)) zirconium dichloride;
ethylidenebis(2-(3-hydroxypropyl)-cyclopentadienyl) zirconium dichloride;
ethylidenebis(3-(3-hydroxyropyl)-cyclopentadienyl) zirconium dichloride;
ethylidene(3-(3-hydroxyropyl)-cyclopentadienyl)(cyclopentadienyl) zirconium dichloride;
ethylidene(2-(3-hydroxypropyl)-cyclopentadienyl)(1-indenyl) zirconium dichloride;
ethylidene(3-3-hydroxyropyl-cyclopentadienyl)(1-indenyl) zirconium dichloride;
ethylidene(2-(3-hydroxypropyl)-cyclopentadienyl)(1-(2-methyl-indenyl)) zirconium dichloride;
ethylidene(3-(3-hydroxyropyl)-cyclopentadienyl)(1-(2-methyl-indenyl)) zirconium dichloride;
ethylidene(2-(3-hydroxypropyl)-cyclopentadienyl)(9-fluorenyl) zirconium dichloride;
ethylidene(3-3-hydroxyropyl-cyclopentadienyl)(9-fluorenyl) zirconium dichloride;
ethylidene(2-(3-hydroxypropyl)-cyclopentadienyl)(9-(2-methyl-fluorenyl)) zirconium dichloride;
ethylidene(3-3-hydroxyropyl-cyclopentadienyl)(9-(2-methyl-fluorenyl)) zirconium dichloride;
ethylidenebis(2-(2-hydroxy-ethoxy)-cyclopentadienyl) zirconium dichloride;
ethylidenebis(3-(2-hydroxy-ethoxy)-cyclopentadienyl) zirconium dichloride;
ethylidene(2-(2-hydroxy-ethoxy)-cyclopentadienyl)(1-indenyl) zirconium dichloride;
ethylidene(3-(2-hydroxy-ethoxy)-cyclopentadienyl)(1-indenyl) zirconium dichloride;
ethylidene(2-(2-hydroxy-ethoxy)-cyclopentadienyl)(1-(2-methyl-indenyl)) zirconium dichloride;
ethylidene(3-(2-hydroxy-ethoxy)-cyclopentadienyl)(1-(2-methyl-indenyl)) zirconium dichloride;
ethylidene(2-(2-hydroxy-ethoxy)-cyclopentadienyl)(9-fluorenyl) zirconium dichloride;
ethylidene(3-(2-hydroxy-ethoxy)-cyclopentadienyl)(9-fluorenyl) zirconium dichloride;
ethylidene(2-(2-hydroxy-ethoxy)-cyclopentadienyl)(9-(2-methyl-fluorenyl)) zirconium dichloride;
ethylidene(3-(2-hydroxy-ethoxy)-cyclopentadienyl)(9-(2-methyl-fluorenyl)) zirconium dichloride;
ethylidenebis(2-(2-hydroxy-ethyl-(dimethyl)silyl)-cyclopentadienyl) zirconium dichloride;
ethylidenebis(3-(2-hydroxy-ethyl-(dimethyl)silyl)-cyclopentadienyl) zirconium dichloride;
ethylidene(2-(2-hydroxy-ethyl-(dimethyl)silyl)-cyclopentadienyl)(1-indenyl) zirconium dichloride;
ethylidene(3-(2-hydroxy-ethyl-(dimethyl)silyl)-cyclopentadienyl)(1-indenyl) zirconium dichloride;
ethylidene(2-(2-hydroxy-ethyl-(dimethyl)silyl)-cyclopentadienyl)(1-(2-methyl-indenyl)) zirconium dichloride;
ethylidene(3-(2-hydroxy-ethyl-(dimethyl)silyl)-cyclopentadienyl)(1-(2-methyl-indenyl)) zirconium dichloride;
ethylidene(2-(2-hydroxy-ethyl-(dimethyl)silyl)-cyclopentadienyl)(9-fluorenyl) zirconium dichloride;
ethylidene(3-(2-hydroxy-ethyl-(dimethyl)silyl)-cyclopentadienyl)(9-fluorenyl) zirconium dichloride;
ethylidene(2-(2-hydroxy-ethyl-(dimethyl)silyl)-cyclopentadienyl)(9-(2-methyl-fluorenyl)) zirconium dichloride;
ethylidene(3-(2-hydroxy-ethyl-(dimethyl)silyl)-cyclopentadienyl)(9-(2-methyl-fluorenyl)) zirconium dichloride;
dimethylsilandiylbis(1-(2-(2-hydroxyethyl)-indenyl)) zirconium dichloride;
dimethylsilandiylbis(1-(3-(2-hydroxyethyl)-indenyl)) zirconium dichloride;
dimethylsilandiyl(1-(2-(2-hydroxyethyl)-indenyl))(1-indenyl) zirconium dichloride;
dimethylsilandiyl(1-(3-(2-hydroxyethyl)-indenyl))(1-indenyl) zirconium dichloride;
dimethylsilandiyl(1-(2-(2-hydroxyethyl)-indenyl))(1-(2-methyl-indenyl)) zirconium dichloride;
dimethylsilandiyl(1-(3-(2-hydroxyethyl)-indenyl))(1-(2-methyl-indenyl)) zirconium dichloride;
dimethylsilandiyl(1-(2-(2-hydroxyethyl)-indenyl))(9-fluorenyl) zirconium dichloride;
dimethylsilandiyl(1-(3-(2-hydroxyethyl)-indenyl))(9-fluorenyl) zirconium dichloride;
dimethylsilandiyl(1-(2-(2-hydroxyethyl)-indenyl))(9-(2-methyl-fluorenyl)) zirconium dichloride;
dimethylsilandiyl(1-(3-(2-hydroxyethyl)-indenyl))(9-(2-methyl-fluorenyl)) zirconium dichloride;
dimethylsilandiylbis(1-(2-(3-hydroxypropyl)-indenyl)) zirconium dichloride;
dimethylsilandiylbis(1-(3-(3-hydroxyropyl)-indenyl)) zirconium dichloride;
dimethylsilandiyl(1-(2-(3-hydroxypropyl)-indenyl))(1-indenyl) zirconium dichloride;
dimethylsilandiyl(1-(3-(3-hydroxyropyl)-indenyl))(1-indenyl) zirconium dichloride;
dimethylsilandiyl(1-(2-(3-hydroxypropyl)-indenyl))(I-(2-methyl-indenyl)) zirconium dichloride;
dimethylsilandiyl(1-(3-(3-hydroxyropyl)-indenyl))(1-(2-methyl-indenyl)) zirconium dichloride;
dimethylsilandiyl(1-(2-(3-hydroxypropyl)-indenyl))(9-fluorenyl) zirconium dichloride;
dimethylsilandiyl(1-(3-(3-hydroxyropyl)-indenyl))(9-fluorenyl) zirconium dichloride;
dimethylsilandiyl(1-(2-(3-hydroxypropyl)-indenyl))(9-(2-methyl-fluorenyl)) zirconium dichloride;
dimethylsilandiyl(1-(3-(3-hydroxyropyl)-indenyl))(9-(2-methyl-fluorenyl)) zirconium dichloride;

dimethylsilandiylbis(1-(2-(2-hydroxy-ethoxy-indenyl)) zirconium dichloride;
dimethylsilandiylbis(,1-(3-(2-hydroxy-ethoxy-indenyl)) zirconium dichloride;
dimethylsilandiyl(1-(2-(2-hydroxy-ethoxy-indenyl))(1-indenyl) zirconium dichloride;
dimethylsilandiyl(1-(3-(2-hydroxy-ethoxy-indenyl))(1-indenyl) zirconium dichloride;
dimethylsilandiyl(1-(2-(2-hydroxy-ethoxy-indenyl))(1-(2-methyl-indenyl)) zirconium dichloride;
dimethylsilandiyl(1-(3-(2-hydroxy-ethoxy-indenyl))(1-(2-methyl-indenyl)) zirconium dichloride;
dimethylsilandiyl(1-(2-(2-hydroxy-ethoxy-indenyl))(9-fluorenyl) zirconium dichloride;
dimethylsilandiyl(1-(3-(2-hydroxy-ethoxy-indenyl))(9-fluorenyl) zirconium dichloride;
dimethylsilandiyl(1-(2-(2-hydroxy-ethoxy-indenyl))(9-(2-methyl-fluorenyl)) zirconium dichloride;
dimethylsilandiyl(1-(3-(2-hydroxy-ethoxy-indenyl))(9-(2-methyl-fluorenyl)) zirconium dichloride;
dimethylsilandiylbis(1-(2-(2-hydroxy-ethyl-(dimethyl)silyl-indenyl)) zirconium dichloride;
dimethylsilandiylbis(1-(3-(2-hydroxy-ethyl-(dimethyl)silyl-indenyl)) zirconium dichloride;
dimethylsilandiyl(1-(2-(2-hydroxy-ethyl-(dimethyl)silyl-indenyl))(1-indenyl) zirconium dichloride;
dimethylsilandiyl(1-(3-(2-hydroxy-ethyl-(dimethyl)silyl-indenyl))(1-indenyl) zirconium dichloride;
dimethylsilandiyl(1-(2-(2-hydroxy-ethyl-(dimethyl)silyl-indenyl))(1-(2-methyl-indenyl)) zirconium dichloride;
dimethylsilandiyl(1-(3-(2-hydroxy-ethyl-(dimethyl)silyl-indenyl))(1-(2-methyl-indenyl)) zirconium dichloride;
dimethylsilandiyl(1-(2-(2-hydroxy-ethyl-(dimethyl)silyl-indenyl))(9-fluorenyl) zirconium dichloride;
dimethylsilandiyl(1-(3-(2-hydroxy-ethyl-(dimethyl)silyl-indenyl))(9-fluorenyl) zirconium dichloride;
dimethylsilandiyl(1-(2-(2-hydroxy-ethyl-(dimethyl)silyl-indenyl))(9-(2-methyl-fluorenyl)) zirconium dichloride;
dimethylsilandiyl(1-(3-(2-hydroxy-ethyl-(dimethyl)silyl-indenyl))(9-(2-methyl-fluorenyl)) zirconium dichloride;
isopropylidenebis(1-(2-(2-hydroxyethyl)-indenyl)) zirconium dichloride;
isopropylidenebis(1-(3-(2-hydroxyethyl)-indenyl)) zirconium dichloride;
isopropylidene(1-(2-(2-hydroxyethyl)-indenyl))(1-indenyl) zirconium dichloride;
isopropylidene(1-(3-(2-hydroxyethyl)-indenyl))(1-indenyl) zirconium dichloride;
isopropylidene(1-(2-(2-hydroxyethyl)-indenyl))(1-(2-methyl-indenyl)) zirconium dichloride;
isopropylidene(1-(3-(2-hydroxyethyl)-indenyl))(1-(2-methyl-indenyl)) zirconium dichloride;
isopropylidene(1-(2-(2-hydroxyethyl)-indenyl))(9-fluorenyl) zirconium dichloride;
isopropylidene(1-(3-(2-hydroxyethyl)-indenyl))(9-fluorenyl) zirconium dichloride;
isopropylidene(1-(2-(2-hydroxyethyl)-indenyl))(9-(2-methyl-fluorenyl)) zirconium dichloride;
isopropylidene(1-(3-(2-hydroxyethyl)-indenyl))(9-(2-methyl-fluorenyl)) zirconium dichloride;
isopropylidenebis(1-(2-(3-hydroxypropyl)-indenyl)) zirconium dichloride;
isopropylidenebis(1-(3-3-hydroxyropyl-indenyl)) zirconium dichloride;
isopropylidene(1-(2-(3-hydroxypropyl)-indenyl))(1-indenyl) zirconium dichloride;
isopropylidene(1-(3-3-hydroxyropyl-indenyl))(1-indenyl) zirconium dichloride;
isopropylidene(1-(2-(3-hydroxypropyl)-indenyl))(1-(2-methyl-indenyl)) zirconium dichloride;
isopropylidene(1-(3-3-hydroxyropyl-indenyl))(1-(2-methyl-indenyl)) zirconium dichloride;
isopropylidene(1-(2-(3-hydroxypropyl)-indenyl))(9-fluorenyl) zirconium dichloride;
isopropylidene(1-(3-3-hydroxyropyl-indenyl))(9-fluorenyl) zirconium dichloride;
isopropylidene(1-(2-(3-hydroxypropyl)-indenyl))(9-(2-methyl-fluorenyl)) zirconium dichloride;
isopropylidene(1-(3-3-hydroxyropyl-indenyl))(9-(2-methyl-fluorenyl)) zirconium dichloride;
isopropylidenebis(1-(2-(2-hydroxy-ethoxy-indenyl)) zirconium dichloride;
isopropylidenebis(1-(3-(2-hydroxy-ethoxy-indenyl)) zirconium dichloride;
isopropylidene(1-(2-(2-hydroxy-ethoxy-indenyl))(1-indenyl) zirconium dichloride;
isopropylidene(1-(3-(2-hydroxy-ethoxy-indenyl))(1-indenyl) zirconium dichloride;
isopropylidene(1-(2-(2-hydroxy-ethoxy-indenyl))(1-(2-methyl-indenyl)) zirconium dichloride;
isopropylidene(1-(3-(2-hydroxy-ethoxy-indenyl))(1-(2-methyl-indenyl)) zirconium dichloride;
isopropylidene(1-(2-(2-hydroxy-ethoxy-indenyl))(9-fluorenyl) zirconium dichloride;
isopropylidene(1-(3-(2-hydroxy-ethoxy-indenyl))(9-fluorenyl) zirconium dichloride;
isopropylidene(1-(2-(2-hydroxy-ethoxy-indenyl))(9-(2-methyl-fluorenyl)) zirconium dichloride;
isopropylidene(1-(3-(2-hydroxy-ethoxy-indenyl))(9-(2-methyl-fluorenyl)) zirconium dichloride;
isopropylidenebis(1-(2-(2-hydroxy-ethyl-(dimethyl)silyl-indenyl)) zirconium dichloride;
isopropylidenebis(1-(3-(2-hydroxy-ethyl-(dimethyl)silyl-indenyl)) zirconium dichloride;
isopropylidene(1-(2-(2-hydroxy-ethyl-(dimethyl)silyl-indenyl))(1-indenyl) zirconium dichloride;
isopropylidene(1-(3-(2-hydroxy-ethyl-(dimethyl)silyl-indenyl))(1-indenyl) zirconium dichloride;
isopropylidene(1-(2-(2-hydroxy-ethyl-(dimethyl)silyl-indenyl))(1-(2-methyl-indenyl)) zirconium dichloride;
isopropylidene(1-(3-(2-hydroxy-ethyl-(dimethyl)silyl-indenyl))(1-(2-methyl-indenyl)) zirconium dichloride;
isopropylidene(1-(2-(2-hydroxy-ethyl-(dimethyl)silyl-indenyl))(9-fluorenyl) zirconium dichloride;
isopropylidene(1-(3-(2-hydroxy-ethyl-(dimethyl)silyl-indenyl))(9-fluorenyl) zirconium dichloride;
isopropylidene(1-(2-(2-hydroxy-ethyl-(dimethyl)silyl-indenyl))(9-(2-methyl-fluorenyl)) zirconium dichloride;
isopropylidene(1-(3-(2-hydroxy-ethyl-(dimethyl)silyl-indenyl))(9-(2-methyl-fluorenyl)) zirconium dichloride;
ethylidenebis(1-(2-(2-hydroxyethyl)-indenyl)) zirconium dichloride;
ethylidenebis(1-(3-(2-hydroxyethyl)-indenyl)) zirconium dichloride;
ethylidene(1-(2-(2-hydroxyethyl)-indenyl))(1-indenyl) zirconium dichloride;
ethylidene(1-(3-(2-hydroxyethyl)-indenyl))(1-indenyl) zirconium dichloride;
ethylidene(1-(2-(2-hydroxyethyl)-indenyl))(1-(2-methyl-indenyl)) zirconium dichloride;
ethylidene(1-(3-(2-hydroxyethyl)-indenyl))(1-(2-methyl-indenyl)) zirconium dichloride;
ethylidene(1-(2-(2-hydroxyethyl)-indenyl))(9-fluorenyl) zirconium dichloride;
ethylidene(1-(3-(2-hydroxyethyl)-indenyl))(9-fluorenyl) zirconium dichloride;

ethylidene(1-(2-(2-hydroxyethyl)-indenyl))(9-(2-methyl-fluorenyl)) zirconium dichloride;
ethylidene(1-(3-(2-hydroxyethyl)-indenyl))(9-(2-methyl-fluorenyl)) zirconium dichloride;
ethylidenebis(1-(2-(3-hydroxypropyl)-indenyl)) zirconium dichloride;
ethylidenebis(1-(3-3-hydroxyropyl-indenyl)) zirconium dichloride;
ethylidene(1-(2-(3-hydroxypropyl)-indenyl))(1 -indenyl) zirconium dichloride;
ethylidene(1-(3-3-hydroxyropyl-indenyl))(1-indenyl) zirconium dichloride;
ethylidene(1-(2-(3-hydroxypropyl)-indenyl))(1-(2-methyl-indenyl)) zirconium dichloride;
ethylidene(1-(3-3-hydroxyropyl-indenyl))(1-(2-methyl-indenyl)) zirconium dichloride;
ethylidene(1-(2-(3-hydroxypropyl)-indenyl))(9-fluorenyl) zirconium dichloride;
ethylidene(1-(3-3-hydroxyropyl-indenyl))(9-fluorenyl) zirconium dichloride;
ethylidenebis(1-(2-(2-hydroxy-ethoxy-indenyl)) zirconium dichloride;
ethylidenebis(1-(3-(2-hydroxy-ethoxy-indenyl)) zirconium dichloride;
ethylidene(1-(2-(2-hydroxy-ethoxy-indenyl))(1-indenyl) zirconium dichloride;
ethylidene(1-(3-(2-hydroxy-ethoxy-indenyl))(1-indenyl) zirconium dichloride;
ethylidene(1-(2-(2-hydroxy-ethoxy-indenyl))(1-(2-methyl-indenyl)) zirconium dichloride;
ethylidene(1-(3-(2-hydroxy-ethoxy-indenyl))(1-(2-methyl-indenyl)) zirconium dichloride;
ethylidene(1-(2-(2-hydroxy-ethoxy-indenyl))(9-fluorenyl) zirconium dichloride;
ethylidene(1-(3-(2-hydroxy-ethoxy-indenyl))(9-fluorenyl) zirconium dichloride;
ethylidene(1-(2-(2-hydroxy-ethoxy-indenyl))(9-(2-methyl-fluorenyl)) zirconium dichloride;
ethylidene(1-(3-(2-hydroxy-ethoxy-indenyl))(9-(2-methyl-fluorenyl)) zirconium dichloride;
ethylidenebis(1-(2-(2-hydroxy-ethyl-(dimethyl)silyl-indenyl)) zirconium dichloride;
ethylidenebis(1-(3-(2-hydroxy-ethyl-(dimethyl)silyl-indenyl)) zirconium dichloride;
ethylidene(1-(2-(2-hydroxy-ethyl-(dimethyl)silyl-indenyl))(1-indenyl) zirconium dichloride;
ethylidene(1-(3-(2-hydroxy-ethyl-(dimethyl)silyl-indenyl))(1-indenyl) zirconium dichloride;
ethylidene(1-(2-(2-hydroxy-ethyl-(dimethyl)silyl-indenyl))(1-(2-methyl-indenyl)) zirconium dichloride;
ethylidene(1-(3-(2-hydroxy-ethyl-(dimethyl)silyl-indenyl))(1-(2-methyl-indenyl)) zirconium dichloride;
ethylidene(1-(2-(2-hydroxy-ethyl-(dimethyl)silyl-indenyl))(9-fluorenyl) zirconium dichloride;
ethylidene(1-(3-(2-hydroxy-ethyl-(dimethyl)silyl-indenyl))(9-fluorenyl) zirconium dichloride;
ethylidene(1 -(2-(2-hydroxy-ethyl-(dimethyl)silyl-indenyl))(9-(2-methyl-fluorenyl)) zirconium dichloride;
ethylidene(1-(3-(2-hydroxy-ethyl-(dimethyl)silyl-indenyl))(9-(2-methyl-fluorenyl)) zirconium dichloride;
dimethylsilylenebis(9-(1-(2-hydroxyethyl)-fluorenyl)) zirconium dichloride;
dimethylsilylene(9-(1-(2-hydroxyethyl)-fluorenyl))(cyclopentadienyl) zirconium dichloride;
dimethylsilylene(9-(1-(2-hydroxyethyl)-fluorenyl))(1-(2-methyl-indenyl)) zirconium dichloride;
dimethylsilylene(9-(1-(2-hydroxyethyl)-fluorenyl))(1-indenyl) zirconium dichloride;
dimethylsilylene(9-(1-(2-hydroxyethyl)-fluorenyl))(9-(2-methyl-fluorenyl)) zirconium dichloride;
dimethylsilylenebis(9-(1-(3-hydroxyropyl)- fluorenyl)) zirconium dichloride;
dimethylsilylene(9-(1-(3-hydroxyropyl)-fluorenyl))(9-fluorenyl) zirconium dichloride;
dimethylsilylene(9-(1-(3-hydroxyropyl)-fluorenyl))(1-(2-methyl-indenyl)) zirconium dichloride;
dimethylsilylene(9-(1-(3-hydroxyropyl)-fluorenyl))(1-indenyl) zirconium dichloride;
dimethylsilylene(9-(1-(3-hydroxyropyl)-fluorenyl))(9-(2-methyl-fluorenyl)) zirconium dichloride;
dimethylsilylenebis(9-(1-(2-hydroxy-ethoxy)-fluorenyl)) zirconium dichloride;
dimethylsilylene(9-(1-(2-hydroxy-ethoxy)-fluorenyl))(9-fluorenyl) zirconium dichloride;
dimethylsilylene(9-(1-(2-hydroxy-ethoxy)-fluorenyl))(9-(2-methyl-indenyl)) zirconium dichloride;
dimethylsilylene(9-(1-(2-hydroxy-ethoxy)-fluorenyl))(1-indenyl) zirconium dichloride;
dimethylsilylene(9-(1-(2-hydroxy-ethoxy)-fluorenyl))(9-(2-methyl-fluorenyl)) zirconium dichloride;
dimethylsilylenebis(9-(1-(2-hydroxy-ethyl-(dimethyl)silyl-fluorenyl)) zirconium dichloride;
dimethylsilylene(9-(1-(2-hydroxy-ethyl-(dimethyl)silyl-fluorenyl))(9-fluorenyl) zirconium dichloride;
dimethylsilylene(9-(1-(2-hydroxy-ethyl-(dimethyl)silyl-fluorenyl))(1-(2-methyl-indenyl)) zirconium dichloride;
dimethylsilylene(9-(1-(2-hydroxy-ethyl-(dimethyl)silyl-fluorenyl))(1-indenyl) zirconium dichloride;
dimethylsilylene(9-(1-(2-hydroxy-ethyl-(dimethyl)silyl-fluorenyl))(9-(2-methyl-fluorenyl)) zirconium dichloride;
isopropylidenebis(9-(1-(2-hydroxyethyl)-fluorenyl)) zirconium dichloride;
isopropylidene(9-(1-(2-hydroxyethyl)-fluorenyl))(9-fluorenyl) zirconium dichloride;
isopropylidene(9-(1-(2-hydroxyethyl)-fluorenyl))(1-(2-methyl-indenyl)) zirconium dichloride;
isopropylidene(9-(1-(2-hydroxyethyl)-fluorenyl))(1-indenyl) zirconium dichloride;
isopropylidene(9-(1-(2-hydroxyethyl)-fluorenyl))(9-(2-methyl-fluorenyl)) zirconium dichloride;
isopropylidenebis(9-(1-(3-hydroxyropyl)-fluorenyl)) zirconium dichloride;
isopropylidene(9-(1-(3-hydroxyropyl)-fluorenyl))(9-fluorenyl) zirconium dichloride;
isopropylidene(9-(1-(3-hydroxyropyl)-fluorenyl))(1-(2-methyl-indenyl)) zirconium dichloride;
isopropylidene(9-(1-(3-hydroxyropyl)-fluorenyl))(1-indenyl) zirconium dichloride;
isopropylidene(9-(1-(3-hydroxyropyl)-fluorenyl))(9-(2-methyl-fluorenyl)) zirconium dichloride;
isopropylidenebis(9-(1-(2-hydroxy-ethoxy)-fluorenyl)) zirconium dichloride;
isopropylidene(9-(1-(2-hydroxy-ethoxy)-fluorenyl))(9-fluorenyl) zirconium dichloride;
isopropylidene(9-(1-(2-hydroxy-ethoxy)-fluorenyl))(1-(2-methyl-indenyl)) zirconium dichloride;
isopropylidene(9-(1-(2-hydroxy-ethoxy)-fluorenyl))(1-indenyl) zirconium dichloride;
isopropylidene(9-(1 -(2-hydroxy-ethoxy)-fluorenyl))(9-(2-methyl-fluorenyl)) zirconium dichloride;
isopropylidenebis(9-(1-(2-hydroxy-ethyl-(dimethyl)silyl-fluorenyl)) zirconium dichloride;
isopropylidene(9-(1-(2-hydroxy-ethyl-(dimethyl)silyl-fluorenyl))(9-fluorenyl) zirconium dichloride;
isopropylidene(9-(1-(2-hydroxy-ethyl-(dimethyl)silyl-fluorenyl))(1-(2-methyl-indenyl)) zirconium dichloride;

isopropylidene(9-(1-2-hydroxy-ethyl-(dimethyl)silyl-fluorenyl))(1-indenyl) zirconium dichloride;
isopropylidene(9-(1-2-hydroxy-ethyl-(dimethyl)silyl-fluorenyl))(9-(2-methyl-fluorenyl)) zirconium dichloride;
ethylidenebis(9-(1-(2-hydroxyethyl-fluorenyl)) zirconium dichloride;
ethylidene(9-(1-(2-hydroxyethyl-fluorenyl))(9-fluorenyl) zirconium dichloride;
ethylidene(9-(1-(2-hydroxyethyl-fluorenyl))(1-(2-methyl-indenyl)) zirconium dichloride;
ethylidene(9-(1-(2-hydroxyethyl-fluorenyl))(1-indenyl) zirconium dichloride;
ethylidene(9-(1-(2-hydroxyethyl-fluorenyl))(9-(2-methyl-fluorenyl)) zirconium dichloride;
ethylidenebis(9-(1-(3-hydroxyropyl-fluorenyl)) zirconium dichloride;
ethylidene(9-(1-(3-hydroxyropyl-fluorenyl))(9-fluorenyl) zirconium dichloride;
ethylidene(9-(1-(3-hydroxyropyl-fluorenyl))(1-(2-methyl-indenyl)) zirconium dichloride;
ethylidene(9-(1-(3-hydroxyropyl-fluorenyl))(1-indenyl) zirconium dichloride;
ethylidene(9-(1 -(3-hydroxyropyl-fluorenyl))(9-(2-methyl-fluorenyl)) zirconium dichloride;
ethylidenebis(9-(1-(2-hydroxy-ethoxy-fluorenyl)) zirconium dichloride;
ethylidene(9-(1-(2-hydroxy-ethoxy-fluorenyl))(9-fluorenyl) zirconium dichloride;
ethylidene(9-(1-(2-hydroxy-ethoxy-fluorenyl))(1-(2-methyl-indenyl)) zirconium dichloride;
ethylidene(9-(1-(2-hydroxy-ethoxy-fluorenyl))(1-indenyl) zirconium dichloride;
ethylidene(9-(1-(2-hydroxy-ethoxy-fluorenyl))(9-(2-methyl-fluorenyl)) zirconium dichloride;
ethylidenebis(9-(1-(2-hydroxy-ethyl-(dimethyl)silyl-fluorenyl)) zirconium dichloride;
ethylidene(9-(1-(2-hydroxy-ethyl-(dimethyl)silyl-fluorenyl))(9-fluorenyl) zirconium dichloride;
ethylidene(9-(1-(2-hydroxy-ethyl-(dimethyl)silyl-fluorenyl))(1-(2-methyl-indenyl)) zirconium dichloride;
ethylidene(9-(1-(2-hydroxy-ethyl-(dimethyl)silyl-fluorenyl))(1-indenyl) zirconium dichloride;
ethylidene(9-(1-(2-hydroxy-ethyl-(dimethyl)silyl-fluorenyl))(9-(2-methyl-fluorenyl)) zirconium dichloride;
2-hydroxyethyl(methyl)silandiylbis(cyclopentadienyl) zirconium dichloride;
2-hydroxyethyl(methyl)silandiylbis(9-fluorenyl) zirconium dichloride;
2-hydroxyethyl(methyl)silandiyl(cyclopentadienyl)(1-indenyl) zirconium dichloride;
2-hydroxyethyl(methyl)silandiyl(cyclopentadienyl)(1-(2-methyl-indenyl)) zirconium dichloride;
2-hydroxyethyl(methyl)silandiyl(cyclopentadienyl)(9-fluorenyl) zirconium dichloride;
2-hydroxyethyl(methyl)silndiyl(cyclopentadienyl)(9-(2-methyl-fluorenyl)) zirconium dichloride;
2-hydroxyethyl(methyl)silandiylbis(1-indenyl) zirconium dichloride;
2-hydroxyethyl(methyl)silandiyl(cyclopentadienyl)(1-(2-methylbenzoindenyl)) zirconium dichloride;
2-hydroxyethyl(methyl)silandiylbis(1-(2-methylbenzoindenyl)) zirconium dichloride;
3-hydroxyropyl(methyl)silandiylbis(cyclopentadienyl) zirconium dichloride;
3-hydroxyropyl(methyl)silandiylbis(9-fluorenyl) zirconium dichloride;
3-hydroxyropyl(methyl)silandiyl(cyclopentadienyl)(1-indenyl) zirconium dichloride;
3-hydroxyropyl(methyl)silandiyl(cyclopentadienyl)(1-(2-methyl-indenyl)) zirconium dichloride;
3-hydroxyropyl(methyl)silandiyl(cyclopentadienyl)(9-fluorenyl) zirconium dichloride;
3-hydroxyropyl(methyl)silandiyl(cyclopentadienyl)(9-(2-methyl-fluorenyl)) zirconium dichloride;
3-hydroxyropyl(methyl)silandiylbis(1-indenyl) zirconium dichloride;
3-hydroxyropyl(methyl)silandiyl(cyclopentadienyl)(1-(2-methylbenzoindenyl)) zirconium dichloride;
2-hydroxy-ethoxy(methyl)silandiylbis(cyclopentadienyl) zirconium dichloride;
2-hydroxy-ethoxy(methyl)silandiyl(cyclopentadienyl)(1-indenyl) zirconium dichloride;
2-hydroxy-ethoxy(methyl)silandiyl(cyclopentadienyl)(1-(2-methyl-indenyl)) zirconium dichloride;
2-hydroxy-ethoxy(methyl)silandiyl(cyclopentadienyl)(9-fluorenyl) zirconium dichloride;
2-hydroxy-ethoxy(methyl)silandiyl(cyclopentadienyl)(9-(2-methyl-fluorenyl)) zirconium dichloride;
2-hydroxy-ethyl-(dimethyl)silyl-(methyl)silandiylbis(cyclopentadienyl) zirconium dichloride;
2-hydroxy-ethyl-(dimethyl)silyl-(methyl)silandiyl(cyclopentadienyl)(1-indenyl) zirconium dichloride;
2-hydroxy-ethyl-(dimethyl)silyl-(methyl)silandiyl(cyclopentadienyl)(1-(2-methyl-indenyl)) zirconium dichloride;
2-hydroxy-ethyl-(dimethyl)silyl-(methyl)silandiyl(cyclopentadienyl)(9-fluorenyl) zirconium dichloride;
2-hydroxy-ethyl-(dimethyl)silyl-( methyl)silandiyl(cyclopentadienyl)(9-(2-methyl-fluorenyl)) zirconium dichloride;
2-hydroxyethyl-(methyl)methylidenebis(cyclopentadienyl) zirconium dichloride;
2-hydroxyethyl-(methyl)methylidene(cyclopentadienyl)(1-indenyl) zirconium dichloride;
2-hydroxyethyl-(methyl)methylidene(cyclopentadienyl)(1-(2-methyl-indenyl)) zirconium dichloride;
2-hydroxyethyl-(methyl)methylidene(cyclopentadienyl)(9-fluorenyl) zirconium dichloride;
2-hydroxyethyl-(methyl)methylidene(cyclopentadienyl)(9-(2-methyl-fluorenyl)) zirconium dichloride;
2-hydroxyethyl-(methyl)methylidenebis(1-indenyl) zirconium dichloride;
2-hydroxyethyl-(methyl)methylidene(cyclopentadienyl)(1-(2-methylbenzoindenyl)) zirconium dichloride;
3-hydroxyropyl-(methyl)methylidenebis(cyclopentadienyl) zirconium dichloride;
3-hydroxyropyl-(methyl)methylidene(cyclopentadienyl)(1-indenyl) zirconium dichloride;
3-hydroxyropyl-(methyl)methylidene(cyclopentadienyl)(1-(2-methyl-indenyl)) zirconium dichloride;
3-hydroxyropyl-(methyl)methylidene(cyclopentadienyl)(9-fluorenyl) zirconium dichloride;
3-hydroxyropyl-(methyl)methylidene(cyclopentadienyl)(9-(2-methyl-fluorenyl)) zirconium dichloride;
3-hydroxyropyl-(methyl)methylidenebis(1-indenyl) zirconium dichloride;
3-hydroxyropyl-(methyl)methylidene(cyclopentadienyl)(1-(2-methylbenzoindenyl)) zirconium dichloride;
2-hydroxy-ethoxy-(methyl)methylidenebis(cyclopentadienyl) zirconium dichloride;
2-hydroxy-ethoxy-(methyl)methylidene(cyclopentadienyl)(1-indenyl) zirconium dichloride;
2-hydroxy-ethoxy-(methyl)methylidene(cyclopentadienyl)(1-(2-methyl-indenyl)) zirconium dichloride;
2-hydroxy-ethoxy-(methyl)methylidene(cyclopentadienyl)(9-fluorenyl) zirconium dichloride;

2-hydroxy-ethoxy-(methyl)methylidene(cyclopentadienyl) (9-(2-methyl-fluorenyl)) zirconium dichloride;
2-hydroxy-ethyl-(dimethyl)silyl-(methyl)methylidenebis (cyclopentadienyl) zirconium dichloride;
2-hydroxy-ethyl-(dimethyl)silyl-(methyl)methylidene (cyclopentadienyl)(1-indenyl) zirconium dichloride;
2-hydroxy-ethyl-(dimethyl)silyl-(methyl)methylidene (cyclopentadienyl)(1-(2-methyl-indenyl)) zirconium dichloride;
2-hydroxy-ethyl-(dimethyl)silyl-(methyl)methylidene (cyclopentadienyl)(9-fluorenyl) zirconium dichloride;
2-hydroxy-ethyl-(dimethyl)silyl-(methyl)methylidene (cyclopentadienyl)(9-(2-methyl-fluorenyl)) zirconium dichloride;
2-hydroxy-ethyl-(dimethyl)silyl-(methyl)methylidenebis(1-indenyl) zirconium dichloride;
1-(2-hydroxyethyl)-ethylidenebis(cyclopentadienyl) zirconium dichloride;
1-(2-hydroxyethyl)-ethylidene-1-(cyclopentadienyl)-2-(1-indenyl) zirconium dichloride;
1-(2-hydroxyethyl)-ethylidene-1-(cyclopentadienyl)-2-(1-(2-methyl-indenyl)) zirconium dichloride;
1-(2-hydroxyethyl)-ethylidene-1-(cyclopentadienyl)-2-(9-fluorenyl) zirconium dichloride;
1-(2-hydroxyethyl)-ethylidene-1-(cyclopentadienyl)-2-(9-(2-methyl-fluorenyl)) zirconium dichloride;
1-(2-hydroxyethyl)-ethylidenebis(1-indenyl) zirconium dichloride;
1-(3-hydroxypropyl)-ethylidenebis(cyclopentadienyl) zirconium dichloride;
1-(3-hydroxypropyl)-ethylidene-1-(cyclopentadienyl)-2-(1-indenyl) zirconium dichloride;
1-(3-hydroxypropyl)-ethylidene-1-(cyclopentadienyl)-2-(1-(2-methyl-indenyl)) zirconium dichloride;
1-(3-hydroxypropyl)-ethylidene-1-(cyclopentadienyl)-2-(9-fluorenyl) zirconium dichloride;
1-(3-hydroxypropyl)-ethylidene-1-(cyclopentadienyl)-2-(9-(2-methyl-fluorenyl)) zirconium dichloride;
1-(3-hydroxypropyl)-ethylidenebis(1-indenyl) zirconium dichloride;
1-(2-hydroxyethoxy)-ethylidenebis(cyclopentadienyl) zirconium dichloride;
1-(2-hydroxyethoxy)-ethylidene-1-(cyclopentadienyl)-2-(1-indenyl) zirconium dichloride;
1-(2-hydroxyethoxy)-ethylidene-1-(cyclopentadienyl)-2-(1-(2-methyl-indenyl)) zirconium dichloride;
1-(2-hydroxyethoxy)-ethylidene-1-(cyclopentadienyl)-2-(9-fluorenyl) zirconium dichloride;
1-(2-hydroxyethoxy)-ethylidene-1-(cyclopentadienyl)-2-(9-(2-methyl-fluorenyl)) zirconium dichloride;
1-(2-hydroxyethyl)-(dimethyl)silyl ethylidenebis (cyclopentadienyl) zirconium dichloride;
1-(2-hydroxyethyl)-(dimethyl)silyl ethylidene1-(cyclopentadienyl)-2-(1-indenyl) zirconium dichloride;
1-(2-hydroxyethyl)-(dimethyl)silyl ethylidene-1-(cyclopentadienyl)-2-(1-(2-methyl-indenyl)) zirconium dichloride;
1-(2-hydroxyethyl)-(dimethyl)silyl ethylidene-1-(cyclopentadienyl)-2-(9-fluorenyl) zirconium dichloride;
1-(2-hydroxyethyl)-(dimethyl)silyl ethylidene-1-(cyclopentadienyl)-2-(9-(2-methyl-fluorenyl)) zirconium dichloride;
(2-hydroxyethyl)(methyl)silandiyl-(tertbutylamido) (cylopentadienyl) zirconium dichloride;
(2-hydroxyethyl)(methyl)silandiyl-(tertbutylamido) (tetramethylcylopentadienyl) zirconium dichloride;
(2-hydroxyethyl)(methyl)silandiyl-(tertbutylamido)(1-indenyl) zirconium dichloride;
(2-hydroxyethyl)(methyl)silandiyl-(tertbutylamido)(1-(2-methyl-indenyl)) zirconium dichloride;
(2-hydroxyethyl)(methyl)silandiyl-(tertbutylamido)(9-fluorenyl) zirconium dichloride;
(2-hydroxyethyl)(methyl)silandiyl-(tertbutylamido)(9-(2-methyl-fluorenyl)) zirconium dichloride;
(2-hydroxyethyl)(methyl)silandiyl-(tertbutylamido)(1-(2-metthylbenzoindenyl) zirconium dichloride;
(dimethyl)silandiyl-(tertbutylamido)(3-((2-hydroxyethyl) cyclopentadienyl) zirconium dichloride;
(dimethyl)silandiyl-(tertbutylamido)(1-(3-(2-hydroxyethyl) indenyl) zirconium dichloride;
(dimethyl)silandiyl-(2-(2-hydroxyethyl)amido) (cylopentadienyl) zirconium dichloride;
(dimethyl)silandiyl-(2-(2-hydroxyethyl)amido) (tetramethylcylopentadienyl) zirconium dichloride;
(dimethyl)silandiyl-(2-(2-hydroxyethyl)amido)(1-indenyl) zirconium dichloride;
(dimethyl)silandiyl-(2-(2-hydroxyethyl)amido)(9-fluorenyl) zirconium dichloride;
(dimethyl)silandiyl-(2-(2-hydroxyethyl)amido)(1-(2-methylbenzoindenyl) zirconium dichloride;
(3-hydroxypropyl)(methyl)silandiyl(tertbutylamido)-(cylopentadienyl) zirconium dichloride;
(3-hydroxypropyl)(methyl)silandiyl-(tertbutylamido) (tetramethylcyclopentadienyl) zirconium dichloride;
(3-hydroxypropyl)(methyl)silandiyl-(tertbutylamido)(1-indenyl) zirconium dichloride;
(3-hydroxypropyl)(methyl)silandiyl-(tertbutylamido)(1-(2-methyl-indenyl)) zirconium dichloride;
(3-hydroxypropyl)(methyl)silandiyl-(tertbutylamido)(9-fluorenyl) zirconium dichloride;
(3-hydroxypropyl)(methyl)silandiyl-(tertbutylamido)(9-(2-methyl-fluorenyl)) zirconium dichloride;
(3-hydroxypropyl)(methyl)silandiyl(tertbutylamido)-(1-(2-methylbenzoindenyl) zirconium dichloride;
(dimethyl)silandiyl-(tertbutylamido)(3-((3-hydroxypropyl) cylopentadienyl) zirconium dichloride;
(dimethyl)silandiyl-(tertbutylamido)(1-(3-(3-hydroxypropyl)indenyl) zirconium dichloride;
(dimethyl)silandiyl-(3-(3-hydroxypropyl)amido) (cylopentadienyl) zirconium dichloride;
(dimethyl)silandiyl-(3-(3-hydroxypropyl)amido) (tetramethylcylopentadienyl) zirconium dichloride;
(dimethyl)silandiyl-(3-(3-hydroxypropyl)amido)(1-indenyl) zirconium dichloride;
(dimethyl)silandiyl-(3-(3-hydroxypropyl)amido)(9-fluorenyl) zirconium dichloride;
(dimethyl)silandiyl-(3-(3-hydroxypropyl)amido)(1-(2-methylbenzoindenyl) zirconium dichloride;
2-hydroxyethyl-methoxy (methyl)silandiyl-(tertbutylamido) (cylopentadienyl) zirconium dichloride;
2-hydroxyethyl-methoxy(methyl)silandiyl-(tertbutylamido) (tetramethylcylopentadienyl) zirconium dichloride;
2-hydroxyethyl-methoxy(methyl)silandiyl-(tertbutylamido) (1-indenyl) zirconium dichloride;
2-hydroxyethyl-methoxy(methyl)silandiyl-(tertbutylamido) (1-(2-methyl-indenyl)) zirconium dichloride;
2-hydroxyethyl-methoxy(methyl)silandiyl-(tertbutylamido) (9-fluorenyl) zirconium dichloride;
2-hydroxyethyl-methoxy(methyl)silandiyl-(tertbutylamido) (9-(2-methyl-fluorenyl)) zirconium dichloride;
(2-hydroxyethoxy)(methyl)silandiyl-(tertbutylamido) (cylopentadienyl) zirconium dichloride;
(2-hydroxyethoxy)(methyl)silandiyl-(tertbutylamido) (tetramethylcylopentadienyl) zirconium dichloride;
(2-hydroxyethoxy)(methyl)silandiyl-(tertbutylamido)(1-indenyl) zirconium dichloride;

(2-hydroxyethoxy)(methyl)silandiyl-(tertbutylamido)(1-(2-methyl-indenyl)) zirconium dichloride;
(2-hydroxyethoxy)(methyl)silandiyl-(tertbutylamido)(9-fluorenyl) zirconium dichloride;
(2-hydroxyethoxy)(methyl)silandiyl-(tertbutylamido)(9-(2-methyl-fluorenyl)) zirconium dichloride;
(2-hydroxyethyl)-(dimethyl)silyl-(methyl)silandiyl (tertbutylamido)-(cylopentadienyl) zirconium dichloride;
(2-hydroxyethyl)-(dimethyl)silyl-(methyl) silandiyl-(tertbutylamido)(tetramethylcyclopentadienyl) zirconium dichloride;
(2-hydroxyethyl)-(dimethyl)silyl-(methyl)silandiyl-(tertbutylamido)(1-indenyl) zirconium dichloride;
(2-hydroxyethyl)-(dimethyl)silyl-(methyl)silandiyl-(tertbutylamido)(1-(2-methyl-indenyl)) zirconium dichloride;
(2-hydroxyethyl)-(dimethyl)silyl-(methyl)silandiyl-(tertbutylamido)(9-fluorenyl) zirconium dichloride;
(2-hydroxyethyl)-(dimethyl)silyl-(methyl)silandiyl-(tertbutylamido)(9-(2-methyl-fluorenyl)) zirconium dichloride;
(2-hydroxyethyl)-(methyl)methylene(tertbutylamido)(cylopentadienyl) zirconium dichloride;
(2-hydroxyethyl)-(methyl)methylene(tertbutylamido)(tetramethylcyclopentadienyl) zirconium dichloride;
(2-hydroxyethyl)-(methyl)methylene(tertbutylamido)(1-indenyl) zirconium dichloride;
(2-hydroxyethyl)-(methyl)methylene(tertbutylamido)(1-(2-methyl-indenyl)) zirconium dichloride;
(2-hydroxyethyl)-(methyl)methylene(tertbutylamido)(9-fluorenyl) zirconium dichloride;
(2-hydroxyethyl)-(methyl)methylene(tertbutylamido)(9-(2-methyl-fluorenyl)) zirconium dichloride;
(3-hydroxypropyl)-(methyl)methylene(tertbutylamido)(cylopentadienyl) zirconium dichloride;
(3-hydroxypropyl)-(methyl)methylene(tertbutylamido)(tetramethylcyclopentadienyl) zirconium dichloride;
(3-hydroxypropyl)-(methyl)methylene(tertbutylamido)(indenyl) zirconium dichloride;
(3-hydroxypropyl)-(methyl)methylene(tertbutylamido)(2-methyl-indenyl) zirconium dichloride;
(3-hydroxypropyl)-(methyl)methylene(tertbutylamido)(9-fluorenyl) zirconium dichloride;
(3-hydroxypropyl)-(methyl)methylene(tertbutylamido)(2-methyl-fluorenyl) zirconium dichloride;
2-hydroxyethyl-methoxy(methyl)methylene (tertbutylamido)(cylopentadienyl) zirconium dichloride;
2-hydroxyethyl-methoxy(methyl)methylene (tertbutylamido)(tetramethylcyclopentadienyl) zirconium dichloride;
2-hydroxyethyl-methoxy(methyl)methylen(tertbutylamido)(1-indenyl) zirconium dichloride;
2-hydroxyethyl-methoxy(methyl)methylen(-tertbutylamido)(1-(2-methyl-indenyl)) zirconium dichloride;
2-hydroxyethyl-methoxy(methyl)methylen(-tertbutylamido)(9-fluorenyl) zirconium dichloride;
2-hydroxyethyl-methoxy(methyl)methylen(-tertbutylamido)(9-(2-methyl-fluorenyl)) zirconium dichloride;
(2-hydroxyethoxy)-(methyl)methylene(tertbutylamido)(cylopentadienyl) zirconium dichloride;
(2-hydroxyethoxy)-(methyl)methylene(tertbutylamido)(tetramethylcyclopentadienyl) zirconium dichloride;
(2-hydroxyethoxy)-(methyl)methylen(tertbutylamido)(1-indenyl) zirconium dichloride;
(2-hydroxyethoxy)-(methyl)methylen(tertbutylamido)(1-(2-methyl-indenyl)) zirconium dichloride;
(2-hydroxyethoxy)-(methyl)methylen(tertbutylamido)(9-fluorenyl) zirconium dichloride;
(2-hydroxyethoxy)-(methyl)methylen(tertbutylamido)(9-(2-methyl-fluorenyl)) zirconium dichloride;
(2-hydroxyethyl)-(dimethyl)silyl-(methyl)methylene (tertbutylamido)(cylopentadienyl) zirconium dichloride;
(2-hydroxyethyl)-(dimethyl)silyl (methyl) methylene (tertbutylamido) (tetramethylcyclopentadienyl) zirconium dichloride;
(2-hydroxyethyl)-(dimethyl)silyl-(methyl)methilene (tertbutyl amido)(1-indenyl) zirconium dichloride;
(2-hydroxyethyl)-(dimethyl)silyl-(methyl)methilene (tertbutylamido)(1-(2-methyl-indenyl)) zirconium dichloride;
(2-hydroxyethyl)-(dimethyl)silyl-(methyl)methilene (tertbutylamido)(9-fluorenyl) zirconium dichloride;
(2-hydroxyethyl)-(dimethyl)silyl-(methyl)methilene (tertbutylamido)(9-(2-methyl-fluorenyl)) zirconium dichloride;
(2-hydroxyethyl)(methyl) silandiyl-oxo(cylopentadienyl) zirconium dichloride;
(2-hydroxyethyl)(methyl) silandiyl-oxo-(tetramethylcyclopentadienyl) zirconium dichloride;
(2-hydroxyethyl)(methyl) silandiyl-oxo(1-indenyl) zirconium dichloride;
(2-hydroxyethyl)(methyl) silandiyl-oxo(1-(2-methyl-indenyl)) zirconium dichloride;
(2-hydroxyethyl)(methyl) silandiyl-oxo(9-fluorenyl) zirconium dichloride;
(2-hydroxyethyl)(methyl) silandiyl-oxo(9-(2-methyl-fluorenyl)) zirconium dichloride;
(3-hydroxypropyl)(methyl) silandiyl-oxo(cylopentadienyl) zirconium dichloride;
(3-hydroxypropyl)(methyl) silandiyl-oxo (tetramethylcyclopentadienyl) zirconium dichloride;
(3-hydroxypropyl)(methyl) silandiyl-oxo(1-indenyl) zirconium dichloride;
(3-hydroxypropyl)(methyl) silandiyl-oxo(1-(2-methyl-indenyl)) zirconium dichloride;
(3-hydroxypropyl)(methyl) silandiyl-oxo(9-fluorenyl) zirconium dichloride;
(3-hydroxypropyl)(methyl) silandiyl-oxo(9-(2-methyl-fluorenyl)) zirconium dichloride;
2-hydroxyethyl-methoxy(methyl) silandiyl- oxo (cylopentadienyl) zirconium dichloride;
2-hydroxyethyl-methoxy(methyl) silandiyl-oxo (tetramethylcyclopentadienyl) zirconium dichloride;
2-hydroxyethyl-methoxy(methyl) silandiyl-oxo(1-indenyl) zirconium dichloride;
2-hydroxyethyl-methoxy(methyl) silandiyl-oxo(1-(2-methyl-indenyl)) zirconium dichloride;
2-hydroxyethyl-methoxy(methyl) silandiyl-oxo(9-fluorenyl) zirconium dichloride;
2-hydroxyethyl-methoxy(methyl) silandiyl-oxo(9-(2-methyl-fluorenyl)) zirconium dichloride;
(2-hydroxyethoxy)(methyl) silandiyl-oxo(cylopentadienyl) zirconium dichloride;
(2-hydroxyethoxy)(methyl) silandiyl-oxo (tetramethylcyclopentadienyl) zirconium dichloride;
(2-hydroxyethoxy)(methyl) silandiyl-oxo(1-indenyl) zirconium dichloride;
(2-hydroxyethoxy)(methyl) silandiyl-oxo(1-(2-methyl-indenyl)) zirconium dichloride;
(2-hydroxyethoxy)(methyl) silandiyl-oxo(9-fluorenyl) zirconium dichloride;
(2-hydroxyethoxy)(methyl) silandiyl-oxo(9-(2-methyl-fluorenyl)) zirconium dichloride;

(2-hydroxyethyl)-(dimethyl)silyl-(methyl) silandiyl-oxo (cylopentadienyl) zirconium dichloride;
(2-hydroxyethyl)-(dimethyl)silyl-(methyl) silandiyl-oxo (tetramethylcyclopentadienyl) zirconium dichloride;
(2-hydroxyethyl)-(dimethyl)silyl-(methyl) silandiyl-oxo(1-indenyl) zirconium dichloride;
(2-hydroxyethyl)-(dimethyl)silyl-(methyl) silandiyl-oxo(1-(2-methyl-indenyl)) zirconium dichloride;
(2-hydroxyethyl)-(dimethyl)silyl-(methyl) silandiyl-oxo (fluorenyl) zirconium dichloride;
(2-hydroxyethyl)-(dimethyl)silyl-(methyl) silandiyl-oxo(9-methylfluorenyl) zirconium dichloride
ethylidene(1-(3-(3-hydroxypropyl)-indenyl)) (cyclopentadienyl) zirconium dichloride;
ethylidene(1-(3-(2-hydroxyethyl)-indenyl)) (cyclopentadienyl) zirconium dichloride;
dimethylsilandiyl(1-(3-(2-hydroxyethyl)-indenyl)) (cyclopentadienyl) zirconium dichloride;
dimethylsilandiyl(1-(3-(3-hydroxypropyl)-indenyl)) (cyclopentadienil) zirconium dichloride;
isopropylidene(1-(3-(2-hydroxyethyl)-indenyl)) (cyclopentadienyl) zirconium dichloride; and
isopropylidene(1-(3-(3-hydroxypropyl)-indenyl (cyclopentadienyl) zirconium dichloride.

26. A metallocene compound selected from the group consisting of:
(2-hydroxyethyl)(methyl)silandiyl-(tertbutylamido) (cylopentadienyl) titanium dichloride;
(2-hydroxyethyl)(methyl)silandiyl-(tertbutylamido) (tetramethylcylopentadienyl) titanium dichloride;
(2-hydroxyethyl)(methyl)silandiyl-(tertbutylamido)(1-indenyl) titanium dichloride;
(2-hydroxyethyl)(methyl)silandiyl-(tertbutylamido)(1-(2-methyl-indenyl)) titanium dichloride;
(2-hydroxyethyl)(methyl)silandiyl-(tertbutylamido)(9-fluorenyl) titanium dichloride;
(2-hydroxyethyl)(methyl)silandiyl-(tertbutylamido)(9-(2-methyl-fluorenyl)) titanium dichloride;
(2-hydroxyethyl)(methyl)silandiyl-(tertbutylamido)(1-(2-metthylbenzoindenyl) titanium dichloride;
(dimethyl)silandiyl-(tertbutylamido)(3-((2-hydroxyethyl) cylopentadienyl) titanium dichloride;
(dimethyl)silandiyl-(tertbutylamido)(1-(3-(2-hydroxyethyl) indenyl) titanium dichloride;
(dimethyl)silandiyl-(2-(2-hydroxyethyl)amido) (cylopentadienyl) titanium dichloride;
(dimethyl)silandiyl-(2-(2-hydroxyethyl)amido) (tetramethylcylopentadienyl) titanium dichloride;
(dimethyl)silandiyl-(2-(2-hydroxyethyl)amido)(1-indenyl) titanium dichloride;
(dimethyl)silandiyl-(2-(2-hydroxyethyl)amido)(9-fluorenyl) titanium dichloride;
(dimethyl)silandiyl-(2-(2-hydroxyethyl)amido)(1-(2-methylbenzoindenyl) titanium dichloride;
(3-hydroxypropyl)(methyl)silandiyl(tertbutylamido)-(cylopentadienyl) titanium dichloride;
(3-hydroxypropyl)(methyl)silandiyl-(tertbutylamido) (tetramethylcylopentadienyl) titanium dichloride;
(3-hydroxypropyl)(methyl)silandiyl-(tertbutylamido)(1-indenyl) titanium dichloride;
(3-hydroxypropyl)(methyl)silandiyl-(tertbutylamido)(1-(2-methyl-indenyl)) titanium dichloride;
(3-hydroxypropyl)(methyl)silandiyl-(tertbutylamido)(9-fluorenyl) titanium dichloride;
(3-hydroxypropyl)(methyl)silandiyl-(tertbutylamido)(9-(2-methyl-fluorenyl)) titanium dichloride;
(3-hydroxypropyl)(methyl)silandiyl(tertbutylamido)-(1-(2-methylbenzoindenyl) titanium dichloride;
(dimethyl)silandiyl-(tertbutylamido)(3-((3-hydroxypropyl) cylopentadienyl) titanium dichloride;
(dimethyl)silandiyl-(tertbutylamido)(1-(3-(3-hydroxypropyl)indenyl) titanium dichloride;
(dimethyl)silandiyl-(3-(3-hydroxypropyl)amido) (cylopentadienyl) titanium dichloride;
(dimethyl)silandiyl-(3-(3-hydroxypropyl)amido) (tetramethylcylopentadienyl) titanium dichloride;
(dimethyl)silandiyl-(3-(3-hydroxypropyl)amido)(1-indenyl) titanium dichloride;
(dimethyl)silandiyl-(3-(3-hydroxypropyl)amido)(9-fluorenyl) titanium dichloride;
(dimethyl)silandiyl-(3-(3-hydroxypropyl)amido)(1-(2-methylbenzoindenyl) titanium dichloride;
2-hydroxyethyl-methoxy (methyl)silandiyl-(tertbutylamido) (cylopentadienyl) titanium dichloride;
2-hydroxyethyl-methoxy(methyl)silandiyl-(tertbutylamido) (tetramethylcyclopentadienyl) titanium dichloride;
2-hydroxyethyl-methoxy(methyl)silandiyl-(tertbutylamido) (1-indenyl) titanium dichloride;
2-hydroxyethyl-methoxy(methyl)silandiyl-(tertbutylamido) (1-(2-methyl-indenyl)) titanium dichloride;
2-hydroxyethyl-methoxy(methyl)silandiyl-(tertbutylamido) (9-fluorenyl) titanium dichloride;
2-hydroxyethyl-methoxy(methyl)silandiyl-(tertbutylamido) (9-(2-methyl-fluorenyl)) titanium dichloride;
(2-hydroxyethoxy)(methyl)silandiyl-(tertbutylamido) (cylopentadienyl) titanium dichloride;
(2-hydroxyethoxy)(methyl)silandiyl-(tertbutylamido) (tetramethylcyclopentadienyl) titanium dichloride;
(2-hydroxyethoxy)(methyl)silandiyl-(tertbutylamido)(1-indenyl) titanium dichloride;
(2-hydroxyethoxy)(methyl)silandiyl-(tertbutylamido)(1-(2-methyl-indenyl)) titanium dichloride;
(2-hydroxyethoxy)(methyl)silandiyl-(tertbutylamido)(9-fluorenyl) titanium dichloride;
(2-hydroxyethoxy)(methyl)silandiyl-(tertbutylamido)(9-(2-methyl-fluorenyl)) titanium dichloride;
(2-hydroxyethyl)-(dimethyl)silyl-(methyl)silandiyl (tertbutylamido)-(cylopentadienyl) titanium dichloride;
(2-hydroxyethyl)-(dimethyl)silyl-(methyl) silandiyl-(tertbutylamido)(tetramethylcyclopentadienyl) titanium dichloride;
(2-hydroxyethyl)-(dimethyl)silyl-(methyl)silandiyl-(tertbutylamido)(1-indenyl) titanium dichloride;
(2-hydroxyethyl)-(dimethyl)silyl-(methyl)silandiyl-(tertbutylamido)(1-(2-methyl-indenyl)) titanium dichloride;
(2-hydroxyethyl)-(dimethyl)silyl-(methyl)silandiyl-(tertbutylamido)(9-fluorenyl) titanium dichloride;
(2-hydroxyethyl)-(dimethyl)silyl-(methyl)silandiyl-(tertbutylamido)(9-(2-methyl-fluorenyl)) titanium dichloride;
(2-hydroxyethyl)-(methyl)methylene(tertbutylamido) (cylopentadienyl) titanium dichloride;
(2-hydroxyethyl)-(methyl)methylene(tertbutylamido) (tetramethylcyclopentadienyl) titanium dichloride;
(2-hydroxyethyl)-(methyl)methylene(tertbutylamido)(1-indenyl) titanium dichloride;
(2-hydroxyethyl)-(methyl)methylene(tertbutylamido)(1-(2-methyl-indenyl)) titanium dichloride;
(2-hydroxyethyl)-(methyl)methylene(tertbutylamido)(9-fluorenyl) titanium dichloride;
(2-hydroxyethyl)-(methyl)methylene(tertbutylamido)(9-(2-methyl-fluorenyl)) titanium dichloride;
(3-hydroxypropyl)-(methyl)methylene(tertbutylamido) (cylopentadienyl) titanium dichloride;

(3-hydroxypropyl)-(methyl)methylene(tertbutylamido)(tetramethylcyclopentadienyl) titanium dichloride;
(3-hydroxypropyl)-(methyl)methylene(tertbutylamido)(indenyl) titanium dichloride;
(3-hydroxypropyl)-(methyl)methylene(tertbutylamido)(2-methyl-indenyl) titanium dichloride;
(3-hydroxypropyl)-(methyl)methylene(tertbutylamido)(9-fluorenyl) titanium dichloride;
(3-hydroxypropyl)-(methyl)methylene(tertbutylamido)(2-methyl-fluorenyl) titanium dichloride;
2-hydroxyethyl-methoxy(methyl)methylene(tertbutylamido)(cylopentadienyl) titanium dichloride;
2-hydroxyethyl-methoxy(methyl)methylene(tertbutylamido)(tetramethylcyclopentadienyl) titanium dichloride;
2-hydroxyethyl-methoxy(methyl)methylen(tertbutylamido)(1-indenyl) titanium dichloride;
2-hydroxyethyl-methoxy(methyl)methylen(-tertbutylamido)(1-(2-methyl-indenyl)) titanium dichloride;
2-hydroxyethyl-methoxy(methyl)methylen(-tertbutylamido)(9-fluorenyl) titanium dichloride;
2-hydroxyethyl-methoxy(methyl)methylen(-tertbutylamido)(9-(2-methyl-fluorenyl)) titanium dichloride;
(2-hydroxyethoxy)-(methyl)methylene(tertbutylamido)(cylopentadienyl) titanium dichloride;
(2-hydroxyethoxy)-(methyl)methylene(tertbutylamido)(tetramethylcyclopentadienyl) titanium dichloride;
(2-hydroxyethoxy)-(methyl)methylen(tertbutylamido)(1-indenyl) titanium dichloride;
(2-hydroxyethoxy)-(methyl)methylen(tertbutylamido)(1-(2-methyl-indenyl)) titanium dichloride;
(2-hydroxyethoxy)-(methyl)methylen(tertbutylamido)(9-fluorenyl) titanium dichloride;
(2-hydroxyethoxy)-(methyl)methylen(tertbutylamido)(9-(2-methyl-fluorenyl)) titanium dichloride;
(2-hydroxyethyl)-(dimethyl)silyl-(methyl)methylene(tertbutylamido)(cylopentadienyl) titanium dichloride;
(2-hydroxyethyl)-(dimethyl)silyl (methyl) methylene (tertbutylamido) (tetramethylcyclopentadienyl) titanium dichloride;
(2-hydroxyethyl)-(dimethyl)silyl-(methyl)methylene(tertbutylamido)(1-indenyl) titanium dichloride;
(2-hydroxyethyl)-(dimethyl)silyl-(methyl)methylene(tertbutylamido)(1-(2-methyl-indenyl)) titanium dichloride;
(2-hydroxyethyl)-(dimethyl)silyl-(methyl)methylene(tertbutylamido)(9-fluorenyl) titanium dichloride;
(2-hydroxyethyl)-(dimethyl)silyl-(methyl)methylene(tertbutylamido)(9-(2-methyl-fluorenyl)) titanium dichloride;
(2-hydroxyethyl)(methyl) silandiyl-oxo(cylopentadienyl) titanium dichloride;
(2-hydroxyethyl)(methyl) silandiyl-oxo-(tetramethylcyclopentadienyl) titanium dichloride;
(2-hydroxyethyl)(methyl) silandiyl-oxo(1-indenyl) titanium dichloride;
(2-hydroxyethyl)(methyl) silandiyl-oxo(1-(2-methyl-indenyl)) titanium dichloride;
(2-hydroxyethyl)(methyl) silandiyl-oxo(9-fluorenyl) titanium dichloride;
(2-hydroxyethyl)(methyl) silandiyl-oxo(9-(2-methyl-fluorenyl)) titanium dichloride;
(3-hydroxypropyl)(methyl) silandiyl-oxo(cylopentadienyl) titanium dichloride;
(3-hydroxypropyl)(methyl) silandiyl-oxo(tetramethylcyclopentadienyl) titanium dichloride;
(3-hydroxypropyl)(methyl) silandiyl-oxo(1-indenyl) titanium dichloride;
(3-hydroxypropyl)(methyl) silandiyl-oxo(1-(2-methyl-indenyl)) titanium dichloride;
(3-hydroxypropyl)(methyl) silandiyl-oxo(9-fluorenyl) titanium dichloride;
(3-hydroxypropyl)(methyl) silandiyl-oxo(9-(2-methyl-fluorenyl)) titanium dichloride;
2-hydroxyethyl-methoxy(methyl) silandiyl-oxo(cylopentadienyl) titanium dichloride;
2-hydroxyethyl-methoxy(methyl) silandiyl-oxo(tetramethylcyclopentadienyl) titanium dichloride;
2-hydroxyethyl-methoxy(methyl) silandiyl-oxo(1-indenyl) titanium dichloride;
2-hydroxyethyl-methoxy(methyl) silandiyl-oxo(1-(2-methyl-indenyl)) titanium dichloride;
2-hydroxyethyl-methoxy(methyl) silandiyl-oxo(9-fluorenyl) titanium dichioride;
2-hydroxyethyl-methoxy(methyl) silandiyl-oxo(9-(2-methyl-fluorenyl)) titanium dichloride;
(2-hydroxyethoxy)(methyl) silandiyl-oxo(cylopentadienyl) titanium dichloride;
(2-hydroxyethoxy)(methyl) silandiyl-oxo(tetramethylcyclopentadienyl) titanium dichloride;
(2-hydroxyethoxy)(methyl) silandiyl-oxo(1-indenyl) titanium dichloride;
(2-hydroxyethoxy)(methyl) silandiyl-oxo(1-(2-methyl-indenyl)) titanium dichloride;
(2-hydroxyethoxy)(methyl) silandiyl-oxo(9-fluorenyl) titanium dichloride;
(2-hydroxyethoxy)(methyl) silandiyl-oxo(9-(2-methyl-fluorenyl)) titanium dichloride;
(2-hydroxyethyl)-(dimethyl)silyl-(methyl) silandiyl-oxo(cylopentadienyl) titanium dichloride;
(2-hydroxyethyl)-(dimethyl)silyl-(methyl) silandiyl-oxo(tetramethylcyclopentadienyl) titanium dichloride;
(2-hydroxyethyl)-(dimethyl)silyl-(methyl) silandiyl-oxo(1-indenyl) titanium dichloride;
(2-hydroxyethyl)-(dimethyl)silyl-(methyl) silandiyl-oxo(1-(2-methyl-indenyl)) titanium dichloride;
(2-hydroxyethyl)-(dimethyl)silyl-(methyl) silandiyl-oxo(fluorenyl) titanium dichloride; and
(2-hydroxyethyl)-(dimethyl)silyl-(methyl) silandiyl-oxo(9-methylfluorenyl) titanium dichloride.

* * * * *